US010155742B2

(12) United States Patent
Whitman et al.

(10) Patent No.: US 10,155,742 B2
(45) Date of Patent: Dec. 18, 2018

(54) HALOFUGINOL DERIVATIVES AND THEIR USE IN COSMETIC AND PHARMACEUTICAL COMPOSITIONS

(71) Applicants: President and Fellows of Harvard College, Cambridge, MA (US); The General Hospital Corporation, Boston, MA (US)

(72) Inventors: Malcolm Whitman, Jamaica Plain, MA (US); Tracy Keller, Jamaica Plain, MA (US); Ralph Mazitschek, Belmont, MA (US)

(73) Assignees: President and Fellows of Harvard College, Cambridge, MA (US); The General Hospital Corporation, Boston, MA (US)

( * ) Notice: Subject to any disclaimer, the term of this patent is extended or adjusted under 35 U.S.C. 154(b) by 99 days.

(21) Appl. No.: 14/371,934

(22) PCT Filed: Jan. 11, 2013

(86) PCT No.: PCT/US2013/021223
§ 371 (c)(1),
(2) Date: Jul. 11, 2014

(87) PCT Pub. No.: WO2013/106702
PCT Pub. Date: Jul. 18, 2013

(65) Prior Publication Data
US 2015/0057297 A1 Feb. 26, 2015

Related U.S. Application Data
(60) Provisional application No. 61/586,271, filed on Jan. 13, 2012.

(51) Int. Cl.
C07D 401/06 (2006.01)
A61K 8/49 (2006.01)
A61Q 19/06 (2006.01)
A61K 45/06 (2006.01)
A61K 31/517 (2006.01)
A61Q 19/00 (2006.01)

(52) U.S. Cl.
CPC .......... *C07D 401/06* (2013.01); *A61K 8/4953* (2013.01); *A61K 31/517* (2013.01); *A61K 45/06* (2013.01); *A61Q 19/00* (2013.01); *A61Q 19/06* (2013.01); *Y02A 50/411* (2018.01)

(58) Field of Classification Search
CPC ..... C07D 401/06; A61K 8/4953; A61Q 19/06
USPC ...................... 514/266.22; 544/287
See application file for complete search history.

(56) References Cited

U.S. PATENT DOCUMENTS

| | | |
|---|---|---|
| 2,694,711 A | 11/1954 | Baker et al. |
| 3,320,124 A | 5/1967 | Waletzky et al. |
| 3,748,327 A | 7/1973 | Beyerle et al. |
| 4,254,105 A | 3/1981 | Fukuda |
| 4,340,596 A | 7/1982 | Schein |
| 4,725,599 A | 2/1988 | Glazer et al. |
| 4,762,838 A | 8/1988 | Glazer |
| 4,800,197 A | 1/1989 | Kowcz et al. |
| 4,891,227 A | 1/1990 | Thaman et al. |
| 4,891,228 A | 1/1990 | Thaman et al. |

(Continued)

FOREIGN PATENT DOCUMENTS

| | | |
|---|---|---|
| CN | 1583729 A | 2/2005 |
| JP | 2002-201192 A | 7/2002 |

(Continued)

OTHER PUBLICATIONS

Wang et al., Concise asymmetric synthesis of antimalarial alkaloid (+)-febrifugine Synlett (2009), (14), 2301-2304 CODEN: SYNLES; ISSN: 0936-5214; English.*

(Continued)

*Primary Examiner* — Paul V Ward
(74) *Attorney, Agent, or Firm* — Wolf, Greenfield & Sacks, P.C.

(57) ABSTRACT

The present invention provides halofuginol, and derivatives and salts thereof, including diasteromerically enriched compositions thereof. The invention also provides pharmaceutical and cosmetic compositions thereof as well as methods for using halofuginol and derivatives thereof in treating chronic inflammatory diseases, autoimmune diseases, dry eye syndrome, fibrosis, scar formation, angiogenesis, viral infections, malaria, ischemic damage, transplant rejection, neurodegenerative diseases, T-cell neoplasms, and cosmetic conditions.

formula (I):

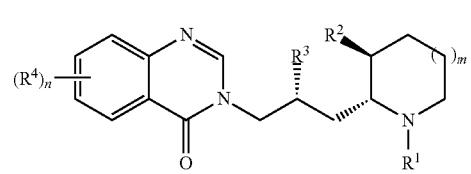

formula (III):

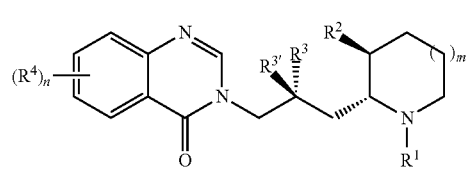

15 Claims, 27 Drawing Sheets
Specification includes a Sequence Listing.

(56) References Cited

U.S. PATENT DOCUMENTS

| | | | |
|---|---|---|---|
| 4,919,934 | A | 4/1990 | Deckner et al. |
| 4,937,370 | A | 6/1990 | Sabatelli |
| 4,960,764 | A | 10/1990 | Figueroa, Jr. et al. |
| 4,999,186 | A | 3/1991 | Sabatelli et al. |
| 5,073,371 | A | 12/1991 | Turner et al. |
| 5,073,372 | A | 12/1991 | Turner et al. |
| 5,087,445 | A | 2/1992 | Haffey et al. |
| 5,223,409 | A | 6/1993 | Ladner et al. |
| 5,449,678 | A | 9/1995 | Pines et al. |
| 5,759,833 | A | 6/1998 | Shiba et al. |
| 6,028,075 | A | 2/2000 | Pines et al. |
| 6,358,539 | B1 | 3/2002 | Murad |
| 6,446,032 | B1 | 9/2002 | Schimmel |
| 9,284,297 | B2 | 3/2016 | Keller et al. |
| 2002/0025316 | A1 | 2/2002 | Ferguson et al. |
| 2005/0227935 | A1 | 10/2005 | McSwiggen et al. |
| 2008/0025917 | A1 | 1/2008 | Whitman et al. |
| 2008/0188498 | A1 | 8/2008 | Zhu |
| 2009/0123389 | A1 | 5/2009 | Whitman et al. |
| 2011/0212100 | A1 | 9/2011 | Keller et al. |
| 2011/0263532 | A1 | 10/2011 | Keller et al. |
| 2011/0311519 | A1 | 12/2011 | Teitelbaum et al. |
| 2012/0058133 | A1 | 3/2012 | Whitman et al. |
| 2016/0317498 | A1 | 11/2016 | Keller et al. |

FOREIGN PATENT DOCUMENTS

| | | |
|---|---|---|
| JP | 2008-531547 A | 8/2008 |
| JP | 2011-530596 A | 12/2011 |
| WO | WO 1998/36061 A2 | 8/1998 |
| WO | WO 1998/43642 A1 | 10/1998 |
| WO | WO 00/09070 A2 | 2/2000 |
| WO | WO 01/17498 A1 | 3/2001 |
| WO | WO 03/016860 A2 | 2/2003 |
| WO | WO 2004/069793 A2 | 8/2004 |
| WO | WO 2007/058990 A2 | 5/2007 |
| WO | WO 2007/109192 A2 | 9/2007 |
| WO | WO 2007/118276 A1 | 10/2007 |
| WO | WO 2007/147217 A1 | 12/2007 |
| WO | WO 2008/094909 A2 | 8/2008 |
| WO | WO 2008/157791 A2 | 12/2008 |
| WO | WO 2009/023267 A2 | 2/2009 |
| WO | WO 2010/019210 A2 | 2/2010 |
| WO | WO 2010/096170 A2 | 8/2010 |
| WO | WO 2013/106702 A1 | 7/2013 |

OTHER PUBLICATIONS

Widjeven et al., Complementary chemoenzymatic routes to both enantiomers of febrifugine Organic & Biomolecular Chemistry (2009), 7(14), 2976-2980 CODEN: OBCRAK; ISSN: 1477-0520; English.*

Zhu et al., Synthesis and biological evaluation of febrifugine analogues as potential antimalarial agents Bioorganic & Medicinal Chemistry (2009), 17(13), 4496-4502 CODEN: BMECEP; ISSN: 0968-0896; English.*

Ashoorzadeh et al., Tetrahedron ( 2009), 65(24), 4671-4680.*

International Search Report and Written Opinion for PCT/US2008/009774, mailed Jan. 22, 2009.

International Preliminary Report on Patentability for PCT/US2008/009774, mailed Feb. 25, 2010.

International Search Report and Written Opinion for PCT/US2010/000460, mailed Nov. 9, 2010.

International Preliminary Report on Patentability for PCT/US2010/000460, mailed Sep. 1, 2011.

Extended European Search Report for EP 09806950.3, mailed Nov. 30, 2012.

International Search Report and Written Opinion for PCT/US2009/004581, mailed Mar. 29, 2010.

International Preliminary Report on Patentability for PCT/US2009/004581, mailed Feb. 24, 2011.

International Search Report and Written Opinion for PCT/US2013/021223, mailed Jun. 19, 2013.

International Preliminary Report on Patentability for PCT/US2013/021223, mailed Jul. 24, 2014.

International Search Report and Written Opinion for PCT/US2007/008752, mailed Oct. 9, 2007.

International Preliminary Report on Patentability for PCT/US2007/008752, mailed Oct. 23, 2008.

[No Author Listed] "A new lead for autoimmune disease." EurekAlert. Public release date Jun. 4, 2009. Available at http://www.eurekalert.org/pub_releases/2009-06/chb-anl060109.php. Last accessed Apr. 28, 2010. 3 pages.

[No Author Listed] "Sun Products Formulary." Cosmetics &Toiletries. Dec. 1990;105:122-39.

[No Author Listed] "Sun Products Formulary." Cosmetics &Toiletries. Mar. 1987;102:117-36.

[No Author Listed] Department of Health, Education, and Welfare. Federal Register. 1978;43(166):38206-69.

[No Author Listed] Goodman and Gilman's The Pharmacological Basis of Therapeutics. 7th ed. 1985:36.

Acosta-Rodriguez et al., Interleukins 1beta and 6 but not transforming growth factor-beta are essential for the differentiation of interleukin 17-producing human T helper cells. Nat Immunol. Sep. 2007;8(9):942-9. Epub Aug. 5, 2007.

Afzali et al., The role of T helper 17 (Th17) and regulatory T cells (Treg) in human organ transplantation and autoimmune disease. Clin Exp Immunol. Apr. 2007;148(1):32-46.

Al-Shaar et al., The Synthesis of Heterocycles via Addition-Elimination Reactions of 4- and 5-Aminoimidazoles. J Chem Soc Perkin 1. 1992;21:2789-811.

Anderson et al., Metabolic reprogramming, caloric restriction and aging. Trends Endocrinol Metab. Mar. 2010;21(3):134-41. doi: 10.1016/j.tem.2009.11.005. Epub Dec. 7, 2009.

Ashoorzadeh et al., Synthetic evaluation of an enantiopure tetrahydropyridine N—oxide. Synthesis of (+)-febrifugine. Tetrahedron. 2009;65(24):4671-80.

Avram, Cellulite: a review of its physiology and treatment. J Cosmet Laser Ther. Dec. 2004;6(4):181-5.

Baker et al., An Antimalarial Alkaloid From Hydrangea. Iv. Functional Derivatives of 3-Alkyl-4-Quinazolones. J Org Chem. 1952;17(1):35-51.

Baker et al., An Antimalarial Alkaloid from Hydrangea. XI. Synthesis of 3-[β-Keto-γ-(3- and 4-Hydroxymethyl-2-Pyrrolidyl)Propyl]-4-Quinazolones. J Org Chem. 1952;17(1):116-131.

Baker et al., An Antimalarial Alkaloid from Hydrangea. XIV. Synthesis of 5-, 6-, 7-, and 8-Monosubstituted Derivatives. J Org Chem. 1952;17(1):141-148.

Banwell et al., Analogues of SB-203207 as inhibitors of tRNA synthetases. Bioorg Med Chem Lett. Oct. 16, 2000;10(20):2263-6.

Barabino et al., The controlled-environment chamber: a new mouse model of dry eye. Invest Ophthalmol Vis Sci. Aug. 2005;46(8):2766-71.

Baumgart et al., Inflammatory bowel disease: cause and immunobiology. Lancet. May 12, 2007;369(9573):1627-40.

Berge et al., Phamaceutical Salts. J Pharma Sciences. 1977;66:1-19.

Berlanga et al., Antiviral effect of the mammalian translation initiation factor 2alpha kinase GCN2 against RNA viruses. EMBO J. Apr. 19, 2006;25(8):1730-40. Epub Apr. 6, 2006.

Bettelli et al., Induction and effector functions of T(H)17 cells. Nature. Jun. 19, 2008;453(7198):1051-7.

Bettelli et al., Reciprocal developmental pathways for the generation of pathogenic effector TH17 and regulatory T cells. Nature. May 11, 2006;441(7090):235-8. Epub Apr. 30, 2006.

Border et al., Transforming growth factor beta in tissue fibrosis. N Engl J Med. Nov. 10, 1994;331(19):1286-92. 9 pages.

Boye et al., S100A4 and metastasis: a small actor playing many roles. Am J Pathol. Feb. 2010;176(2):528-35. Epub Dec. 17, 2009.

Branton et al., TGF-β and fibrosis. Microbes Infect. 1999;1:1349-65.

Bromberg et al., Stat3 as an oncogene. Cell. Aug. 6, 1999;98(3):295-303.

Bronte et al., Regulation of immune responses by L-arginine metabolism. Nat Rev Immunol. Aug. 2005;5(8):641-54.

Brunsing et al., B- and T-cell development both involve activity of the unfolded protein response pathway. J Biol Chem. Jun. 27, 2008;283(26):17954-61. Epub Mar. 28, 2008.

Burgess et al., PPARgamma agonists inhibit TGF-beta induced pulmonary myofibroblast differentiation and collagen production: implications for therapy of lung fibrosis. Am J Physiol Lung Cell Mol Physiol. Jun. 2005;288(6):L1146-53. Epub Feb. 25, 2005.

Cahn et al., [Spezifikation der molekularen Chiralität] Specification of Molecular Chirality. Angew Chem. 1966;78:413-47. German. Translated in Angew Chem Int Ed. 1966;5:385-415.

Cahn et al., Specification of Configuration about Quadricovalent Asymmetric Atoms J Chem Soc. 1951:612-22.

Cahn et al., The Specification of Asymmetric Configuration in Organic Chemistry. Experientia. 1956;12:81-94.

Cahn, An Introduction to the Sequence Rule. J Chem, Educ. 1964;41:116-125.

Campbell et al., A multi-station culture force monitor system to study cellular contractility. J Biomech. Jan. 2003;36(1):137-40.

Carell et al., A Solution-Phase Screening Procedure for the Isolation of Active Compounds from a Library of Molecules. Angew Chem Intl Ed Engl. 1994;33(20):2061-64.

Carlson et al., The Th17-ELR+ CXC chemokine pathway is essential for the development of central nervous system autoimmune disease. J Exp Med. Apr. 14, 2008;205(4):811-23. Epub Mar. 17, 2008.

Caro et al., Effect of 40% restriction of dietary amino acids (except methionine) on mitochondrial oxidative stress and biogenesis, AIF and SIRT1 in rat liver. Biogerontology. Oct. 2009;10(5):579-92. doi: 10.1007/s10522-008-9200-4. Epub Nov. 28, 2008.

Carrell et al., A Novel Procedure for the Synthesis of Libraries Containing Small Organic Molecules. Angew Chem Int Ed Engl. 1994;33:2059-61.

Chang et al., Coactivator TIF1beta interacts with transcription factor C/EBPbeta and glucocorticoid receptor to induce alpha1-acid glycoprotein gene expression. Mol Cell Biol. Oct. 1998;18(10):5880-7.

Chauhan et al., Autoimmunity in dry eye is due to resistance of Th17 to Treg suppression. J Immunol. Feb. 1, 2009;182(3):1247-52.

Cho et al., An unnatural biopolymer. Science. Sep. 3, 1993;261(5126):1303-5.

Coatney et al., Studies in human malaria. XXV. Trial of febrifugine, an alkaloid obtained from Dichroa febrifuga lour., against the Chesson strain of Plasmodium vivax. J Natl Malar Soc. Jun. 1950;9(2):183-6.

Cobbold et al., Infectious tolerance via the consumption of essential amino acids and mTOR signaling. Proc Natl Acad Sci U S A. Jul. 21, 2009;106(29):12055-60. doi: 10.1073/pnas.0903919106. Epub Jun. 30, 2009.

Corry et al., Primarily vascularized allografts of hearts in mice. The role of H-2D, H-2K, and non-H-2 antigens in rejection. Transplantation. Oct. 1973;16(4):343-50.

Critchley et al., Antibacterial activity of REP8839, a new antibiotic for topical use. Antimicrob Agents Chemother. Oct. 2005;49(10):4247-52.

Cull et al., Screening for receptor ligands using large libraries of peptides linked to the C terminus of the lac repressor. Proc Natl Acad Sci U S A. Mar. 1, 1992;89(5):1865-9.

Cwirla et al., Peptides on phage: a vast library of peptides for identifying ligands. Proc Natl Acad Sci U S A. Aug. 1990;87(16):6378-82.

De Jonge et al., Phase I and pharmacokinetic study of halofuginone, an oral quinazolinone derivative in patients with advanced solid tumours. Eur J Cancer. Aug. 2006;42(12):1768-74. Epub Jul. 3, 2006.

Desmoulière et al., Tissue repair, contraction, and the myofibroblast. Wound Repair Regen. Jan.-Feb. 2005;13(1):7-12.

Deval et al., Amino acid limitation regulates the expression of genes involved in several specific biological processes through GCN2-dependent and GCN2-independent pathways. FEBS J. Feb. 2009;276(3):707-18. doi: 10.1111/j.1742-4658.2008.06818.x. Epub Dec. 19, 2008.

Devlin et al., Random peptide libraries: a source of specific protein binding molecules. Science. Jul. 27, 1990;249(4967):404-6.

Dewitt et al., "Diversomers": an approach to nonpeptide, nonoligomeric chemical diversity. Proc Natl Acad Sci U S A. Aug. 1, 1993;90(15):6909-13.

Djuretic et al., Transcription factors T-bet and Runx3 cooperate to activate Ifng and silence Il4 in T helper type 1 cells. Nat Immunol. Feb. 2007;8(2):145-53. Epub Dec. 31, 2006.

Dong et al., Uncharged tRNA activates GCN2 by displacing the protein kinase moiety from a bipartite tRNA-binding domain. Mol Cell. Aug. 2000;6(2):269-79.

Dong, TH17 cells in development: an updated view of their molecular identity and genetic programming. Nat Rev Immunol. 2008;8:337-48.

Eastwood et al., Quantitative analysis of collagen gel contractile forces generated by dermal fibroblasts and the relationship to cell morphology. J Cell Physiol. Jan. 1996;166(1):33-42.

Elkin et al., Inhibition of bladder carcinoma angiogenesis, stromal support, and tumor growth by halofuginone. Cancer Res. Aug. 15, 1999;59(16):4111-8.

Elliot et al, Inflammatory Bowel Disease and Celiac Disease. In: The Autoimmune Diseases, 3rd ed., Rose et al., eds., Academic Press, San Diego, CA. 1998:477-509.

Elson et al., Experimental models of inflammatory bowel disease. Gastroenterology. Oct. 1995;109(4):1344-67.

Emamaullee et al., Caspase inhibitor therapy enhances marginal mass islet graft survival and preserves long-term function in islet transplantation. Diabetes. May 2007;56(5):1289-98. Epub Feb. 15, 2007.

Emmanuvel et al., A concise enantioselective synthesis of (+)-febrifugine. Tetrahedron: Asymmetry. 2009;20(1):84-88.

Erb et al., Recursive deconvolution of combinatorial chemical libraries. Proc Natl Acad Sci U S A. Nov. 22, 1994;91(24):11422-6.

Esposito et al., Rapamycin inhibits relapsing experimental autoimmune encephalomyelitis by both effector and regulatory T cells modulation. J Neuroimmunol. Mar. 30, 2010;220(1-2):52-63. doi: 10.1016/j.jneuroim.2010.01.001. Epub Feb. 11, 2010.

Fafournoux et al., Amino acid regulation of gene expression. Biochem J. Oct. 1, 2000;351(Pt 1):1-12.

Farhanullah et al., Design and synthesis of quinolinones as methionyl-tRNA synthetase inhibitors. Bioorg Med Chem. Nov. 1, 2006;14(21):7154-9. Epub Jul. 18, 2006.

Felici et al., Selection of antibody ligands from a large library of oligopeptides expressed on a multivalent exposition vector. J Mol Biol. Nov. 20, 1991;222(2):301-10.

Fingar et al., Target of rapamycin (TOR): an integrator of nutrient and growth factor signals and coordinator of cell growth and cell cycle progression. Oncogene. Apr. 19, 2004;23(18):3151-71.

Finlay et al., Metabolism, migration and memory in cytotoxic T cells. Nat Rev Immunol. Feb. 2011;11(2):109-17. doi: 10.1038/nri2888. Epub Jan. 14, 2011.

Finn et al., Discovery of a potent and selective series of pyrazole bacterial methionyl-tRNA synthetase inhibitors. Bioorg Med Chem Lett. Jul. 7, 2003;13(13):2231-4.

Flanders, Smad3 as a mediator of the fibrotic response. Int J Exp Pathol. Apr. 2004;85(2):47-64.

Fodor et al., Multiplexed biochemical assays with biological chips. Nature. Aug. 5, 1993;364(6437):555-6.

Fontana et al., Extending healthy life span—from yeast to humans. Science. Apr. 16, 2010;328(5976):321-6. doi: 10.1126/science.1172539.

Gallop et al., Applications of combinatorial technologies to drug discovery. 1. Background and peptide combinatorial libraries. J Med Chem. Apr. 29, 1994;37(9):1233-51.

Gavin et al., Foxp3-dependent programme of regulatory T-cell differentiation. Nature. Feb. 15, 2007;445(7129):771-5. Epub Jan. 14, 2007.

Glimcher et al., Recent developments in the transcriptional regulation of cytolytic effector cells. Nat Rev Immunol. Nov. 2004;4(11):900-11.

Gnainsky et al., Gene expression during chemically induced liver fibrosis: effect of halofuginone on TGF-beta signaling. Cell Tissue Res. Apr. 2007;328(1):153-66. Epub Dec. 19, 2006.

Grohmann et al., Control of immune response by amino acid metabolism. Immunol Rev. Jul. 2010;236:243-64. doi: 10.1111/j.1600-065X.2010.00915.x.

Gutcher et al., APC-derived cytokines and T cell polarization in autoimmune inflammation. J Clin Invest. May 2007;117(5):1119-27.

Haigis et al., The aging stress response. Mol Cell. Oct. 22, 2010;40(2):333-44. doi: 10.1016/j.molcel.2010.10.002.

Hanami et al., Synthesis of 8-(2'-deoxy-β-D-ribofuranosyl)-imidazo[1,2,a]-s-triazin-4-one. Tetrahedron Lett. 2007;48(22):3801-03.

Hansen et al., Reversible inhibition by histidinol of protein synthesis in human cells at the activation of histidine. J Biol Chem. Jun. 25, 1972;247(12):3854-7.

Harding et al., An integrated stress response regulates amino acid metabolism and resistance to oxidative stress. Mol Cell. Mar. 2003;11(3):619-33.

Harding et al., Regulated translation initiation controls stress-induced gene expression in mammalian cells. Mol Cell. Nov. 2000;6(5):1099-108.

Heacock et al., Synthesis and Aminoacyl-tRNA Synthetase Inhibitory Activity of Prolyl Adenylate Analogs. Bioorganic Chemistry. 1996;24(3):273-89.

Heim-Riether et al., A novel method for the synthesis of imidazo[5,1-f][1,2,4]triazin-4(3H)-ones. J Org Chem. Sep. 2, 2005;70(18):7331-7.

Hinz et al., Cell-matrix and cell-cell contacts of myofibroblasts: role in connective tissue remodeling. Thromb Haemost. Dec. 2003;90(6):993-1002.

Hinz et al., Mechanisms of force generation and transmission by myofibroblasts. Curr Opin Biotechnol. Oct. 2003;14(5):538-46.

Hotamisligil et al., Nutrient sensing and inflammation in metabolic diseases. Nat Rev Immunol. Dec. 2008;8(12):923-34. doi: 10.1038/nri2449.

Houghten et al., The use of synthetic peptide combinatorial libraries for the identification of bioactive peptides. Biotechniques. Sep. 1992;13(3):412-21.

Howitz et al., Xenohormesis: sensing the chemical cues of other species. Cell. May 2, 2008;133(3):387-91. doi: 10.1016/j.cell.2008.04.019.

Hsu et al., TRIP-BR: a novel family of PHD zinc finger- and bromodomain-interacting proteins that regulate the transcriptional activity of E2F-1/DP-1. EMBO J. May 1, 2001;20(9):2273-85.

Huang et al., Dendritic cells, indoleamine 2,3 dioxygenase and acquired immune privilege. Int Rev Immunol. Apr. 2010;29(2):133-55. doi: 10.3109/08830180903349669.

Huebner et al., Functional resolution of fibrosis in mdx mouse dystrophic heart and skeletal muscle by halofuginone. Am J Physiol Heart Circ Physiol. Apr. 2008;294(4):H1550-61. Epub Feb. 8, 2008.

Hurdle et al., Prospects for aminoacyl-tRNA synthetase inhibitors as new antimicrobial agents. Antimicrob Agents Chemother. Dec. 2005;49(12):4821-33.

Hutchings et al., An Antimalarial Alkaloid From Hydrangea. III. Degradation. J Org Chem. 1952;17(1):19-34.

Ibba et al., Aminoacyl-tRNA synthesis. Annu Rev Biochem. 2000;69:617-50.

Inman et al., SB-431542 is a potent and specific inhibitor of transforming growth factor-beta superfamily type I activin receptor-like kinase (ALK) receptors ALK4, ALK5, and ALK7. Mol Pharmacol. Jul. 2002;62(1):65-74.

Ivanov et al., The orphan nuclear receptor RORgammat directs the differentiation program of proinflammatory IL-17+ T helper cells. Cell. Sep. 22, 2006;126(6):1121-33.

Jahn et al., Mono Q chromatography permits recycling of DNA template and purification of RNA transcripts after T7 RNA polymerase reaction. Nucleic Acids Res. May 25, 1991;19(10):2786.

Jarman-Smith et al., Human fibroblast culture on a crosslinked dermal porcine collagen matrix. Biochem Eng J. 2004;20(2-3):217-22.

Jarvest et al., Conformational restriction of methionyl tRNA synthetase inhibitors leading to analogues with potent inhibition and excellent gram-positive antibacterial activity. Bioorg Med Chem Lett. Apr. 7, 2003;13(7):1265-8.

Jarvest et al., Definition of the heterocyclic pharmacophore of bacterial methionyl tRNA synthetase inhibitors: potent antibacterially active non-quinolone analogues. Bioorg Med Chem Lett. Aug. 2, 2004;14(15):3937-41.

Jarvest et al., Discovery and optimisation of potent, selective, ethanolamine inhibitors of bacterial phenylalanyl tRNA synthetase. Bioorg Med Chem Lett. May 2, 2005;15(9):2305-9.

Jarvest et al., Inhibitors of bacterial tyrosyl tRNA synthetase: synthesis of carbocyclic analogues of the natural product SB-219383. Bioorg Med Chem Lett. Sep. 17, 2001;11(18):2499-502.

Jiang et al., Antimalarial activities and therapeutic properties of febrifugine analogs. Antimicrob Agents Chemother. Mar. 2005;49(3):1169-76.

Kanamaru et al., In vitro and in vivo antibacterial activities of TAK-083, an agent for treatment of Helicobacter pylori infection. Antimicrob Agents Chemother. Sep. 2001;45(9):2455-9.

Kanemaki et al., TIP49b, a new RuvB-like DNA helicase, is included in a complex together with another RuvB-like DNA helicase, TIP49a. J Biol Chem. Aug. 6, 1999;274(32):22437-44.

Kanitakis, Anatomy, histology and immunohistochemistry of normal human skin. Eur J Dermatol. Jul.-Aug. 2002;12(4):390-9; quiz 400-1.

Kastelein et al., Discovery and biology of IL-23 and IL-27: related but functionally distinct regulators of inflammation. Annu Rev Immunol. 2007;25:221-42.

Kawamura et al., Anti-angiogenesis effects of borrelidin are mediated through distinct pathways: threonyl-tRNA synthetase and caspases are independently involved in suppression of proliferation and induction of apoptosis in endothelial cells. J Antibiot (Tokyo). Aug. 2003;56(8):709-15.

Keller et al., Halofuginone and other febrifugine derivatives inhibit prolyl-tRNA synthetase. Nat Chem Biol. Feb. 12, 2012;8(3):311-7. doi: 10.1038/nchembio.790.

Kikuchi et al., Exploration of a new type of antimalarial compounds based on febrifugine. J Med Chem. Jul. 27, 2006;49(15):4698-706.

Kikuchi et al., Potent antimalarial febrifugine analogues against the plasmodium malaria parasite. J Med Chem. Jun. 6, 2002;45(12):2563-70.

Kilberg et al., Nutritional control of gene expression: how mammalian cells respond to amino acid limitation. Annu Rev Nutr. 2005;25:59-85.

Kim et al., Aminoacyl-tRNA synthetases and their inhibitors as a novel family of antibiotics. Appl Microbiol Biotechnol. May 2003;61(4):278-88. Epub Mar 1, 2003.

Kim et al., Deoxyribosyl analogues of methionyl and isoleucyl sulfamate adenylates as inhibitors of methionyl-tRNA and isoleucyl-tRNA synthetases. Bioorg Med Chem Lett. Jul. 15, 2005;15(14):3389-93.

Klarmann, Chapter 8. Suntan Prepartions. In: Cosmetics Science and Technology. Sagarin et al., eds. Interscience Publishers, Inc., New York. 1957:189-212.

Kobayashi et al., Catalytic Asymmetric Synthesis of Antimalarial Alkaloids Febrifugine and Isofebrifugine and Their Biological Activity. J Org Chem. Sep. 3, 1999;64(18):6833-6841.

Koepfli et al., Alkaloids of Dichroa febrifuga; isolation and degradative studies. J Am Chem Soc. Mar. 1949;71(3):1048-54.

Kolls et al., Interleukin-17 family members and inflammation. Immunity. Oct. 2004;21(4):467-76.

Koon et al., Phase II AIDS Malignancy Consortium Trial of Topical Halofuginone in AIDS-Related Kaposi Sarcoma. J Acquir Immune Defic Syndr. 2011;56:64-68.

Laan et al., Neutrophil recruitment by human IL-17 via C-X-C chemokine release in the airways. J Immunol. Feb. 15, 1999;162(4):2347-52.

Lam et al., A new type of synthetic peptide library for identifying ligand-binding activity. Nature. Nov. 7, 1991;354(6348):82-4.

Lam, Application of combinatorial library methods in cancer research and drug discovery. Anticancer Drug Des. Apr. 1997;12(3):145-67.

Le Douarin et al., TIF1alpha: a possible link between KRAB zinc finger proteins and nuclear receptors. J Steroid Biochem Mol Biol. Apr. 1998;65(1-6):43-50.

Lee et al., N-Alkoxysulfamide, N-hydroxysulfamide, and sulfamate analogues of methionyl and isoleucyl adenylates as inhibitors of methionyl-tRNA and isoleucyl-tRNA synthetases. Bioorg Med Chem Lett. Mar. 24, 2003;13(6):1087-92.

Lee et al., XBP-1 regulates a subset of endoplasmic reticulum resident chaperone genes in the unfolded protein response. Mol Cell Biol. Nov. 2003;23(21):7448-59.

Leiba et al., Halofuginone inhibits NF-kappaB and p38 MAPK in activated T cells. J Leukoc Biol. Aug. 2006;80(2):399-406. Epub Jun. 12, 2006.

Li et al., Inhibitory effect of pravastatin on transforming growth factor beta1-inducible gene h3 expression in a rat model of chronic cyclosporine nephropathy. Am J Nephrol. Nov.-Dec. 2005;25(6):611-20. Epub Nov. 22, 2005.

Li et al., Matrix metalloproteinase-2 and tissue inhibitor of metalloproteinase-2 in colorectal carcinoma invasion and metastasis. World J Gastroenterol. May 28, 2005;11(20):3046-50.

Li et al., Transforming growth factor-beta regulation of immune responses. Annu Rev Immunol. 2006;24:99-146.

Lin et al., IRE1 signaling affects cell fate during the unfolded protein response. Science. Nov. 9, 2007;318(5852):944-9.

Lin et al., The integrated stress response prevents demyelination by protecting oligodendrocytes against immune-mediated damage. J Clin Invest. Feb. 2007;117(2):448-56.

Lohr et al., Role of IL-17 and regulatory T lymphocytes in a systemic autoimmune disease. J Exp Med. Dec. 25, 2006;203(13):2785-91. Epub Nov. 27, 2006.

Ludviksson et al., Dysregulated intrathymic development in the IL-2-deficient mouse leads to colitis-inducing thymocytes. J Immunol. Jan. 1, 1997;158(1):104-11.

Manel et al., The differentiation of human T(H)-17 cells requires transforming growth factor-beta and induction of the nuclear receptor RORγt. Nat Immunol. Jun. 2008;9(6):641-9. Epub May 4, 2008.

McGaha et al., Effect of halofuginone on the development of tight skin (TSK) syndrome. Autoimmunity. Jul. 2002;35(4):277-82.

McGaha et al., Halofuginone, an inhibitor of type-I collagen synthesis and skin sclerosis, blocks transforming-growth-factor-beta-mediated Smad3 activation in fibroblasts. J Invest Dermatol. Mar. 2002;118(3):461-70.

McGeachy et al., TGF-beta and IL-6 drive the production of IL-17 and IL-10 by T cells and restrain T(H)-17 cell-mediated pathology. Nat Immunol. Dec. 2007;8(12):1390-7. Epub Nov. 11, 2007.

Mesaros et al., Activation of Stat3 signaling in AgRP neurons promotes locomotor activity. Cell Metab. Mar. 2008;7(3):236-48.

Mirrashed et al., Pilot study of dermal and subcutaneous fat structures by MRI in individuals who differ in gender, BMI, and cellulite grading. Skin Res Technol. Aug. 2004;10(3):161-8.

Miyamoto et al., Identification of *Saccharomyces cerevisiae* isoleucyl-tRNA synthetase as a target of the G1-specific inhibitor Reveromycin A. J Biol Chem. Aug. 9, 2002;277(32):28810-4. Epub Jun. 5, 2002.

Mombaerts et al., Spontaneous development of inflammatory bowel disease in T cell receptor mutant mice. Cell. Oct. 22, 1993;75(2):274-82.

Mucida et al., Reciprocal TH17 and regulatory T cell differentiation mediated by retinoic acid. Science. Jul. 13, 2007;317(5835):256-60. Epub Jun. 14, 2007.

Mukhopadhyay et al., The GAIT system: a gatekeeper of inflammatory gene expression. Trends Biochem Sci. Jul. 2009;34(7):324-31. doi: 10.1016/j.tibs.2009.03.004. Epub Jun. 15, 2009.

Munn et al., GCN2 kinase in T cells mediates proliferative arrest and anergy induction in response to indoleamine 2,3-dioxygenase. Immunity. May 2005;22(5):633-42.

Nagler et al., Inhibition of collagen synthesis, smooth muscle cell proliferation, and injury-induced intimal hyperplasia by halofuginone. Arterioscler Thromb Vasc Biol. Jan. 1997;17(1):194-202.

Nagler et al., Reduction in pulmonary fibrosis in vivo by halofuginone. Am J Respir Crit Care Med. Oct. 1996;154(4 Pt 1):1082-6.

Nagler et al., Suppression of hepatocellular carcinoma growth in mice by the alkaloid coccidiostat halofuginone. Eur J Cancer. Jun. 2004;40(9):1397-403.

Nagler et al., Topical Treatment of Cutaneous Chronic Graft Versus Host Disease with Halofuginone: A Novel Inhibitor of Collagen Type 1 Synthesis. Transplantation. 1999;68(11):1806-09.

Nath et al., Metformin attenuated the autoimmune disease of the central nervous system in animal models of multiple sclerosis. J Immunol. Jun. 15, 2009;182(12):8005-14. doi: 10.4049/jimmunol.0803563.

Nomura et al., Oncogenic activation of c-Myb correlates with a loss of negative regulation by TIF1beta and Ski. J Biol Chem. Apr. 16, 2004;279(16):16715-26. Epub Feb. 3, 2004.

Nurieva et al., Essential autocrine regulation by IL-21 in the generation of inflammatory T cells. Nature. Jul. 26, 2007;448(7152):480-3. Epub Jun. 20, 2007.

Nürnberger et al., So-called cellulite: an invented disease. J Dermatol Surg Oncol. Mar. 1978;4(3):221-9.

Ono et al., Improved technique of heart transplantation in rats. J Thorac Cardiovasc Surg. Feb. 1969;57(2):225-9.

Ooi et al., A concise enantioselective synthesis of antimalarial febrifugine alkaloids. Org Lett. Mar. 22, 2001;3(6):953-5.

Oslejskova et al., Metastasis-inducing S100A4 protein is associated with the disease activity of rheumatoid arthritis. Rheumatology (Oxford). Dec. 2009;48(12):1590-4. Epub Oct. 14, 2009.

Oslejskova et al., The metastasis associated protein S100A4: a potential novel link to inflammation and consequent aggressive behaviour of rheumatoid arthritis synovial fibroblasts. Ann Rheum Dis. Nov. 2008;67(11):1499-504. Epub Dec. 4, 2007.

Ozcelik et al., The effect of halofuginone, a specific inhibitor of collagen type 1 synthesis, in the prevention of esophageal strictures related to caustic injury. Am J Surg. Feb. 2004;187(2):257-60.

Paley et al., Tryptophanyl-tRNA synthetase in cell lines resistant to tryptophan analogs. Exp Cell Res. Jul. 1991;195(1):66-78.

Palii et al., Specificity of amino acid regulated gene expression: analysis of genes subjected to either complete or single amino acid deprivation. Amino Acids. May 2009;37(1):79-88. doi: 10.1007/s00726-008-0199-2. Epub Nov. 14, 2008.

Park et al., A distinct lineage of CD4 T cells regulates tissue inflammation by producing interleukin 17. Nat Immunol. Nov. 2005;6(11):1133-41. Epub Oct. 2, 2005.

Park et al., Indoleamine 2,3-dioxygenase-expressing dendritic cells are involved in the generation of CD4+CD25+ regulatory T cells in Peyer's patches in an orally tolerized, collagen-induced arthritis mouse model. Arthritis Res Ther. 2008;10(1):R11. Epub Jan. 25, 2008.

Patani et al., Bioisosterism: A Rational Approach in Drug Design. Chem Rev. Dec. 19, 1996;96(8):3147-3176.

Patil et al., Synthesis of Pyrrolo[2,1-f][1,2,4]triazine Congeners of Nucleic Acid Purines via the N-Amination of 2-Substituted Pyrroles [1]. J Heterocycl Chem. 1994;31(4):781-86.

Peitz et al., Ability of the hydrophobic FGF and basic TAT peptides to promote cellular uptake of recombinant Cre recombinase: a tool for efficient genetic engineering of mammalian genomes. Proc Natl Acad Sci U S A. Apr. 2, 2002;99(7):4489-94. Epub Mar. 19, 2002.

Peng et al., Preparation of a 7-arylthieno[3,2-d]pyrimidin-4-amine library. J Comb Chem. May-Jun. 2007;9(3):431-6. Epub Mar. 8, 2007.

Peng et al., The immunosuppressant rapamycin mimics a starvation-like signal distinct from amino acid and glucose deprivation. Mol Cell Biol. Aug. 2002;22(15):5575-84.

Petraitiene et al., Efficacy, plasma pharmacokinetics, and safety of icofungipen, an inhibitor of Candida isoleucyl-tRNA synthetase, in treatment of experimental disseminated candidiasis in persistently neutropenic rabbits. Antimicrob Agents Chemother. May 2005;49(5):2084-92.

Petraitis et al., Efficacy of PLD-118, a novel inhibitor of candida isoleucyl-tRNA synthetase, against experimental oropharyngeal and esophageal candidiasis caused by fluconazole-resistant C. albicans. Antimicrob Agents Chemother. Oct. 2004;48(10):3959-67.

Piérard et al., Cellulite: from standing fat herniation to hypodermal stretch marks. Am J Dermatopathol. Feb. 2000;22(1):34-7.

Pines et al., Halofuginone to treat fibrosis in chronic graft-versus-host disease and scleroderma. Biol Blood Marrow Transplant. Jul. 2003;9(7):417-25.

Pines et al., Halofuginone: a novel antifibrotic therapy. Gen Pharmacol. Apr. 1998;30(4):445-50.

Pines et al., Reduction in dermal fibrosis in the tight-skin (Tsk) mouse after local application of halofuginone. Biochem Pharmacol. Nov. 1, 2001;62(9):1221-7.

Pleiss et al., Rapid, transcript-specific changes in splicing in response to environmental stress. Mol Cell. Sep. 21, 2007;27(6):928-37.

Plouffe et al., In silico activity profiling reveals the mechanism of action of antimalarials discovered in a high-throughput screen. Proc Natl Acad Sci U S A. Jul. 1, 2008;105(26):9059-64. doi: 10.1073/pnas.0802982105. Epub Jun. 25, 2008.

Pohlmann et al., New aminoacyl-tRNA synthetase inhibitors as antibacterial agents. Curr Drug Targets Infect Disord. Dec. 2004;4(4):261-72.

Powell et al., The mammalian target of rapamycin: linking T cell differentiation, function, and metabolism. Immunity. Sep. 24, 2010;33(3):301-11. doi: 10.1016/j.immuni.2010.09.002.

Puccetti et al., IDO and regulatory T cells: a role for reverse signalling and non-canonical NF-kappaB activation. Nat Rev Immunol. Oct. 2007;7(10):817-23.

Qiu et al., Crystal structure of *Staphylococcus aureus* tyrosyl-tRNA synthetase in complex with a class of potent and specific inhibitors. Protein Sci. Oct. 2001;10(10):2008-16.

Querleux et al., Anatomy and physiology of subcutaneous adipose tissue by in vivo magnetic resonance imaging and spectroscopy: relationships with sex and presence of cellulite. Skin Res Technol. May 2002;8(2):118-24.

Rashid et al., Topical omega-3 and omega-6 fatty acids for treatment of dry eye. Arch Ophthalmol. Feb. 2008;126(2):219-25.

Rathmell et al., Activated Akt promotes increased resting T cell size, CD28-independent T cell growth, and development of autoimmunity and lymphoma. Eur J Immunol. Aug. 2003;33(8):2223-32.

Reich et al., GenePattern 2.0. Nat Genet. May 2006;38(5):500-1.

Reigan et al., Synthesis and enzymatic evaluation of xanthine oxidase-activated prodrugs based on inhibitors of thymidine phosphorylase. Bioorg Med Chem Lett. Nov. 1, 2004;14(21):5247-50.

Reiner, Development in motion: helper T cells at work. Cell. Apr. 6, 2007;129(1):33-6.

Rocchi et al., A unique PPARgamma ligand with potent insulin-sensitizing yet weak adipogenic activity. Mol Cell. Oct. 2001;8(4):737-47.

Romani et al., IL-17 and therapeutic kynurenines in pathogenic inflammation to fungi. J Immunol. Apr. 15, 2008;180(8):5157-62.

Ron et al., Signal integration in the endoplasmic reticulum unfolded protein response. Nat Rev Mol Cell Biol. Jul. 2007;8(7):519-29.

Rosenbaum et al., An exploratory investigation of the morphology and biochemistry of cellulite. Plast Reconstr Surg. Jun. 1998;101(7):1934-9.

Ruan et al., A unique hydrophobic cluster near the active site contributes to differences in borrelidin inhibition among threonyl-tRNA synthetases. J Biol Chem. Jan. 7, 2005;280(1):571-7. Epub Oct. 26, 2004.

Sancak et al., The Rag GTPases bind raptor and mediate amino acid signaling to mTORC1. Science. Jun. 13, 2008;320(5882):1496-501. doi: 10.1126/science.1157535. Epub May 22, 2008.

Sato et al., Halofuginone prevents extracellular matrix deposition in diabetic nephropathy. Biochem Biophys Res Commun Feb. 6, 2009;379(2):411-6. Epub Dec. 27, 2008.

Scheuner et al., The unfolded protein response: a pathway that links insulin demand with beta-cell failure and diabetes. Endocr Rev. May 2008;29(3):317-33. Epub Apr. 24, 2008.

Schimmel et al., Aminoacyl tRNA synthetases as targets for new anti-infectives. FASEB J. Dec. 1998;12(15):1599-609.

Schneider et al., S100A4: a common mediator of epithelial-mesenchymal transition, fibrosis and regeneration in diseases? J Mol Med. May 2008;86(5):507-22. Epub Mar. 6, 2008.

Scott et al., Searching for peptide ligands with an epitope library. Science. Jul. 27, 1990;249(4967):386-90.

Smalls et al., Quantitative model of cellulite: three-dimensional skin surface topography, biophysical characterization, and relationship to human perception. J Cosmet Sci. Mar.-Apr. 2005;56(2):105-20.

Song, A facile synthesis of new 4-(phenylamino)thieno[3,2,d]pyrimidines using 3-aminothiophene-2-carboxamide. Heterocyclic Communications. 2007;13(1):33-34.

Splan et al., Transfer RNA modulates the editing mechanism used by class II prolyl-tRNA synthetase. J Biol Chem. Mar. 14, 2008;283(11):7128-34. doi: 10.1074/jbc.M709902200. Epub Jan. 7, 2008.

Srinivas et al., Cre reporter strains produced by targeted insertion of EYFP and ECFP into the ROSA26 locus. BMC Dev Biol. 2001;1:4. Epub Mar. 27, 2001.

Stefanska et al., A potent seryl tRNA synthetase inhibitor SB-217452 isolated from a *streptomyces* species. J Antibiot (Tokyo). Dec. 2000;53(12):1346-53.

Stefanska et al., SB-203207 and SB-203208, two novel isoleucyl tRNA synthetase inhibitors from a *streptomyces* sp. I. Fermentation, isolation and properties. J Antibiot (Tokyo). Apr. 2000;53(4):357-63.

Steinman et al., How to successfully apply animal studies in experimental allergic encephalomyelitis to research on multiple sclerosis. Ann Neurol. Jul. 2006;60(1):12-21.

Steinman, A brief history of T(H)17, the first major revision in the T(H)1/T(H)2 hypothesis of T cell-mediated tissue damage. Nat Med. Feb. 2007;13(2):139-45. Erratum in: Nat Med. Mar. 2007;13(3):385.

Stockinger et al., Differentiation and function of Th17 T cells. Curr Opin Immunol. Jun. 2007;19(3):281-6. Epub Apr. 12, 2007.

Sukemoto et al., Concise asymmetric synthesis of (+)-febrifugine utilizing trans-selective intramolecular conjugate addition. Synthesis. 2008;19:3081-87.

Sukuru et al., Discovering new classes of Brugia malayi asparaginyl-tRNA synthetase inhibitors and relating specificity to conformational change. J Comput Aided Mol Des. Mar. 2006;20(3):159-78. Epub Apr. 28, 2006.

Sundrud et al., Halofuginone inhibits TH17 cell differentiation by activating the amino acid starvation response. Science. Jun. 5, 2009;324(5932):1334-8.

Sundrud et al., Transcription factor GATA-1 potently represses the expression of the HIV-1 coreceptor CCR5 in human T cells and dendritic cells. Blood. Nov. 15, 2005;106(10):3440-8. Epub Aug. 9, 2005.

Szymanski et al., The new aspects of aminoacyl-tRNA synthetases. Acta Biochim Pol. 2000;47(3):821-34.

Takaya et al., New type of febrifugine analogues, bearing a quinolizidine moiety, show potent antimalarial activity against Plasmodium malaria parasite. J Med Chem. Aug. 12, 1999;42(16):3163-6.

Tandon et al., Potent and selective inhibitors of bacterial methionyl tRNA synthetase derived from an oxazolone-dipeptide scaffold. Bioorg Med Chem Lett. Apr. 19, 2004;14(8):1909-11.

Taniguchi et al., A diastereocontrolled synthesis of (+)-febrifugine: a potent antimalarial piperidine alkaloid. Org Lett. Oct. 5, 2000;2(20):3193-5.

Ting et al., Isolation of prolyl-tRNA synthetase as a free form and as a form associated with glutamyl-tRNA synthetase. J Biol Chem. Sep. 5, 1992;267(25):17701-9.

Toh et al., The role of T cells in rheumatoid arthritis: new subsets and new targets. Curr Opin Rheumatol. May 2007;19(3):284-8.

Tomasek et al., Myofibroblasts and mechano-regulation of connective tissue remodelling. Nat Rev Mol Cell Biol. May 2002;3(5):349-63.

Torchala et al., IA, database of known ligands of aminoacyl-tRNA synthetases. J Comput Aided Mol Des. Sep. 2007;21(9):523-5. Epub Sep. 20, 2007.

Van De Vijver et al., Aminoacyl-tRNA synthetase inhibitors as potent and synergistic immunosuppressants. J Med Chem. May 22, 2008;51(10):3020-9. Epub Apr. 26, 2008.

Van Vlasselaer et al., Transforming growth factor-beta directs IgA switching in human B cells. J Immunol. Apr. 1, 1992;148(7):2062-7.

Veldhoen et al., Signals mediated by transforming growth factor-beta initiate autoimmune encephalomyelitis, but chronic inflammation is needed to sustain disease. Nat Immunol. Nov. 2006;7(11):1151-6. Epub Sep. 24, 2006.

Veldhoen et al., TGFβ in the context of an inflammatory cytokine milieu supports de novo differentiation of IL-17-producing T cells. Immunity. Feb. 2006;24(2):179-89.

Viennet et al., Contractile forces generated by striae distensae fibroblasts embedded in collagen lattices. Arch Dermatol Res. Jul. 2005;297(1):10-7. Epub May 10, 2005.

Vogel et al., Neue Synthesen von Pyrazolo[1,5-a]-s-triazinen. Helvetica Chimica Acta. 1975;58(3):761-71. German.

Von Bubnoff et al., Indoleamine 2,3-dioxygenase-expressing myeloid dendritic cells and macrophages in infectious and noninfectious cutaneous granulomas. J Am Acad Dermatol. Oct. 2011;65(4):819-32. doi: 10.1016/j.jaad.2010.07.050. Epub Apr. 17, 2011.

Waldner et al., Activation of antigen-presenting cells by microbial products breaks self tolerance and induces autoimmune disease. J Clin Invest. Apr. 2004;113(7):990-7.

Wang et al., A synthetic triterpenoid, 2-cyano-3,12-dioxooleana-1,9-dien-28-oic acid (CDDO), is a ligand for the peroxisome proliferator-activated receptor gamma. Mol Endocrinol. Oct. 2000;14(10):1550-6.

Wang et al., Concise asymmetric synthesis of antimalarial alkaloid (+)-febrifugine. Synlett. 2009;14:2301-04.

Watson et al., Fibrillin microfibrils are reduced in skin exhibiting striae distensae. Br J Dermatol. Jun. 1998;138(6):931-7.

Weaver et al., IL-17 family cytokines and the expanding diversity of effector T cell lineages. Annu Rev Immunol. 2007;25:821-52.

Weber et al., Statins in the treatment of central nervous system autoimmune disease. J Neuroimmunol. Sep. 2006;178(1-2):140-8. Epub Jul. 24, 2006.

Wee et al., Asymmetric synthesis of (+)-isofebrifugine and (−)-sedacryptine from a common chiral nonracemic building block. Org Lett. Sep. 4, 2008;10(17):3869-72. Epub Aug. 2, 2008.

Wei et al., IL-21 is produced by Th17 cells and drives IL-17 production in a STAT3-dependent manner. J Biol Chem. Nov. 30, 2007;282(48):34605-10. Epub Sep. 20, 2007.

Wijdeven et al., Complementary chemoenzymatic routes to both enantiomers of febrifugine. Org Biomol Chem. Jul. 21, 2009;7(14):2976-80. Epub Jun. 4, 2009.

Wilen et al., Strategies in Optical Resolutions. Tetrahedron. 1977;33:2725-36.

Wilson et al., Development, cytokine profile and function of human interleukin 17-producing helper T cells. Nat Immunol. Sep. 2007;8(9):950-7. Epub Aug. 5, 2007.

Winum et al., Sulfamates and their therapeutic potential. Med Res Rev. Mar. 2005;25(2):186-228.

Wu et al., FOXP3 controls regulatory T cell function through cooperation with NFAT. Cell. Jul. 28, 2006;126(2):375-87.

Xavier et al., Amelioration of radiation-induced fibrosis: inhibition of transforming growth factor-beta signaling by halofuginone. J Biol Chem. Apr. 9, 2004;279(15):15167-76. Epub Jan. 19, 2004.

Xiao et al., Leucine deprivation increases hepatic insulin sensitivity via GCN2/mTOR/S6K1 and AMPK pathways. Diabetes. Mar. 2011;60(3):746-56. doi: 10.2337/db10-1246. Epub Jan. 31, 2011.

Yang et al., STAT3 regulates cytokine-mediated generation of inflammatory helper T cells. J Biol Chem. Mar. 30, 2007;282(13):9358-63. Epub Feb. 3, 2007.

Yang et al., T helper 17 lineage differentiation is programmed by orphan nuclear receptors ROR alpha and ROR gamma Immunity. Jan. 2008;28(1):29-39. Epub Dec. 27, 2007.

Yaremchuk et al., A succession of substrate induced conformational changes ensures the amino acid specificity of Thermus thermophiles prolyl-tRNA synthetase: comparison with histidyl-tRNA synthetase. J Mol Biol. Jun. 15, 2001;309(4):989-1002.

Yasumi et al., Interleukin-17 as a new marker of severity of acute hepatic injury. Hepatol Res. Apr. 2007;37(4):248-54.

Yu et al., A series of heterocyclic inhibitors of phenylalanyl-tRNA synthetases with antibacterial activity. Bioorg Med Chem Lett. Mar. 8, 2004;14(5):1343-6.

Yu et al., A series of quinoline analogues as potent inhibitors of C. albicans prolyl tRNA synthetase. Bioorg Med Chem Lett. Feb. 26, 2001;11(4):541-4.

Zelante et al., IL-23 and the Th17 pathway promote inflammation and impair antifungal immune resistance. Eur J Immunol. Oct. 2007;37(10):2695-706.

Zhou et al., IL-6 programs T(H)-17 cell differentiation by promoting sequential engagement of the IL-21 and IL-23 pathways. Nat Immunol. Sep. 2007;8(9):967-74. Epub Jun. 20, 2007.

Zhu et al., Synthesis and biological evaluation of febrifugine analogues as potential antimalarial agents. Bioorg Med Chem. Jul. 1, 2009;17(13):4496-502. doi: 10.1016/j.bmc.2009.05.011. Epub May 9, 2009.

Zhu et al., Synthesis and evaluation of 4-quinazolinone compounds as potential antimalarial agents. Eur J Med Chem. Sep. 2010;45(9):3864-9. doi: 10.1016/j.ejmech.2010.05.040. Epub May 24, 2010.

Zhu et al., Synthesis and evaluation of febrifugine analogues as potential antimalarial agents. Bioorg Med Chem Lett. Apr. 1, 2006;16(7):1854-8. Epub Jan. 24, 2006.

Ziolkowska et al., High levels of IL-17 in rheumatoid arthritis patients: IL-15 triggers in vitro IL-17 production via cyclosporin A-sensitive mechanism. J Immunol. Mar. 1, 2000;164(5):2832-8.

Zoncu et al., mTOR: from growth signal integration to cancer, diabetes and ageing. Nat Rev Mol Cell Biol. Jan. 2011;12(1):21-35. doi: 10.1038/nrm3025. Epub Dec. 15, 2010.

Zuckermann et al., Discovery of nanomolar ligands for 7-transmembrane G-protein-coupled receptors from a diverse N-(substituted)glycine peptoid library. J Med Chem. Aug. 19, 1994;37(17):2678-85.

Adams et al., Symptomatic treatment of Huntington disease. Neurotherapeutics. Apr. 2008;5(2):181-97. doi: 10.1016/j.nurt.2008.01.008.

Leaf et al., Why We're Losing the War on Cancer—and How to Win It. Fortune. Time Inc. Published on Mar. 9, 2004. 26 pages.

Posakony et al., Inhibitors of Sir2: evaluation of splitomicin analogues. J Med Chem. May 6, 2004;47(10):2635-44.

Salloway et al., Disease-modifying therapies in Alzheimer's disease. Alzheimers Dement. Mar. 2008;4(2):65-79. doi: 10.1016/j.jalz.2007.10.001. Epub Feb. 20, 2008.

Van Laar et al., Tweaking Microtubules to Treat Scleroderma. PLoS Medicine, 2005;2(12):1230-1. DOI: 10.1371/journal.pmed.0020415.

* cited by examiner

| | Halofuginone | Amodiaquine |
|---|---|---|
| RPMI | 1 (0.7nM) | 1 (30 nM) |
| +5x L-Pro | 7 | 0.8 |
| +25x L-Pro | 21.8 | 1 |
| +25x D-Pro | 1.1 | 1 |
| +25x L-Met | 1 | 1 |
| +25x L-Ile | 1.3 | 0.9 |
| +25x L-Orn | 1.2 | 0.9 |

MAZ1907

MAZ1908

HALOFUGINOL DERIVATIVES AND THEIR USE IN COSMETIC AND PHARMACEUTICAL COMPOSITIONS

RELATED APPLICATION

The present application is a national stage filing under 35 U.S.C. §371 of international PCT application, PCT/US2013/021223, filed Jan. 11, 2013, which claims priority under 35 U.S.C. §119(e) to U.S. provisional patent application, U.S. Ser. No. 61/586,271, filed Jan. 13, 2012, each of which is incorporated herein by reference.

GOVERNMENT SUPPORT

This invention was made with U.S. Government support under GM089885 awarded by National Institutes of Health. The U.S. Government has certain rights in the invention.

BACKGROUND OF THE INVENTION

Halofuginone is a halogenated derivative of febrifugine, a natural product extracted from the roots of the hydrangea *Dichroa febrifuga*. *Dichroa febrifuga* is one of the "fifty fundamental herbs" of traditional Chinese medicine, originally used as an anti-malarial remedy (Jiang et al., *Antimicrob. Agents Chemother.* (2005) 49:1169-1176). Halofuginone, otherwise known as 7-bromo-6-chloro-3-[3-(3-hydroxy-2-piperidinyl)-2-oxopropyl]-4(3H)-quinazolinone, and halofuginone derivatives were first described in U.S. Pat. No. 2,694,711, incorporated herein by reference. Febrifugine has been shown to be the active ingredient in *Dichroa febrifuga* extracts; halofuginone was originally synthesized in search of less toxic anti-malarial derivatives of febrifugine. In addition to its anti-malarial properties, however, halofuginone has striking anti-fibrotic properties in vivo (Pines, et al., *Biol. Blood Marrow Transplant* (2003) 9: 417-425; U.S. Pat. No. 6,028,075, incorporated herein by reference). Halofuginone shows some toxicity in humans, such as nausea, vomiting, and fatigue, and possibly bleeding complications (de Jonge et al., *Eur. J. Cancer* (2006) 42: 1768-1774).

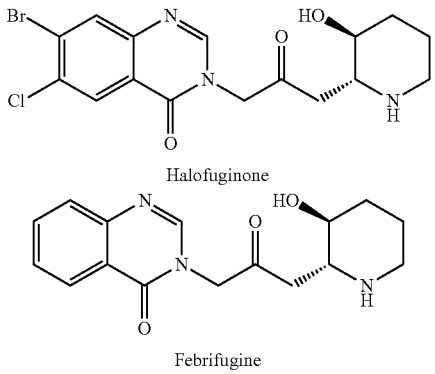

Since halofuginone has shown promising biological activities, there remains a need for identifying further related compounds with useful biological activities, especially those that may have advantages over halofuginone, such as decreased toxicity or increased stability.

SUMMARY OF THE INVENTION

Halofuginol and related compounds have been found to have surprising biological activities. Compounds described herein may have more desirable properties than halofuginone or febrifugine. For example, inventive compounds may be less toxic than halofuginone or febrifugine, and/or the inventive compounds may be more potent than halofuginone or febrifugine. In some embodiments, provided compounds are more stable than halofuginone or febrifugine. In other embodiments, provided compounds display improved physicochemical properties and/or improved DMPK properties when compared with halofuginone or febrifugine. In certain embodiments, provided compounds are more soluble than halofuginone or febrifugine. Halofuginol and other compounds of the present invention are useful in the treatment of chronic inflammatory diseases, autoimmune diseases, dry eye syndrome, fibrosis, scar formation, angiogenesis, viral infections, malaria, ischemic damage, transplant and implant rejection, neurodegenerative diseases, and cosmetic applications. Pharmaceutical and cosmetic compositions of provided compounds as well as methods of using such compounds and compositions are also provided by the present invention.

In one aspect, the inventive compounds are generally of the formula:

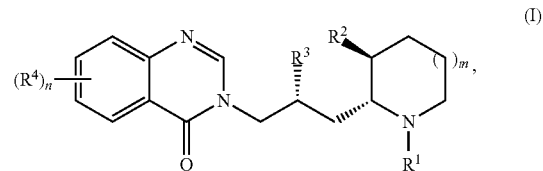

or a pharmaceutically acceptable salt thereof,
wherein
$R^1$ is hydrogen, acyl, optionally substituted $C_{1-6}$ alkyl, or a protecting group;
$R^2$ is halogen, or an optionally substituted group selected from alkyl, alkenyl, alkynyl, $-OR^A$, $-N(R^C)_2$, $-SR^{A1}$, $-C(=O)R^{A1}$, $-C(=O)OR^{A1}$, $-C(=O)N(R^{A2})_2$, $-SOR^{A1}$, $-SO_2R^{A1}$, $-CN$, and $-CF_3$;
$R^3$ is halogen, or an optionally substituted group selected from alkyl, alkenyl, alkynyl, $-OR^B$, $-N(R^D)_2$, $-SR^{A1}$, $-C(=O)R^{A1}$, $-C(=O)OR^{A1}$, $-C(=O)N(R^{A2})_2$, $-SOR^{A1}$, $-SO_2R^{A1}$, $-CN$, and $-CF_3$;
each $R^4$ is independently hydrogen, halogen, or an optionally substituted group selected from alkyl, alkenyl, alkynyl, carbocyclyl, heterocyclyl, aryl, heteroaryl, $-OR^{A1}$, $-N(R^{A2})_2$, $-SR^{A1}$, $-C(=O)R^{A1}$, $-C(=O)OR^{A1}$, $-C(=O)N(R^{A2})_2$, $-OC(=O)R^{A1}$, $-NR^{A2}C(=O)R^{A2}$, $-NR^{A2}C(=O)OR^{A1}$, $-NR^{A2}C(=O)N(R^{A2})_2$, $-C(=NR^{A2})N(R^{A2})_2$, $-NR^{A2}C(=NR^{A2})R^{A2}$, $-NR^{A2}C(=NR^{A2})N(R^{A2})_2$, $-SOR^{A1}$, $-SO_2R^{A1}$, $-NR^{A2}SO_2R^{A1}$, $-SO_2N(R^{A2})_2$, $-CN$, $-SCN$, and $-NO_2$;
each $R^{A1}$ is independently hydrogen, an amino protecting group, or an optionally substituted group selected from alkyl, alkenyl, alkynyl, carbocyclyl, heterocyclyl, aryl, and heteroaryl;
each $R^{A2}$ is independently hydrogen or an optionally substituted group selected from alkyl, alkenyl, alkynyl, carbocyclyl, heterocyclyl, aryl, and heteroaryl, or two $R^{A2}$ groups are taken together with their intervening atoms to form an optionally substituted heterocycle;
$R^A$ and $R^B$ are independently hydrogen, a hydroxyl protecting group, acyl, or optionally substituted alkyl;
$R^C$ is hydrogen, an amino protecting group, acyl, or optionally substituted alkyl; or two $R^C$ are taken together with their intervening atoms to form an optionally substituted heterocycle;

R$^D$ is hydrogen, an amino protecting group, acyl, or alkyl; or two R$^D$ are taken together with their intervening atoms to form an optionally substituted heterocycle;

n is 0, 1, 2, 3, or 4; and m is 0 or 1.

In another aspect, the inventive compounds are generally of the formula:

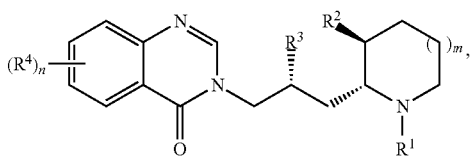

(II)

or a pharmaceutically acceptable salt thereof, wherein

R$^1$ is hydrogen, acyl, optionally substituted C$_{1-6}$ alkyl, or a protecting group;

R$^2$ is —OR$^A$ or —N(R$^C$)$_2$;

R$^3$ is —OR$^B$ or —N(R$^D$)$_2$;

each R$^4$ is independently hydrogen, halogen, or an optionally substituted group selected from alkyl, alkenyl, alkynyl, carbocyclyl, heterocyclyl, aryl, heteroaryl, —OR$^{A1}$, —N(R$^{A2}$)$_2$, —SR$^{A1}$, —C(=O)R$^{A1}$, —C(=O)OR$^{A1}$, —C(=O)N(R$^{A2}$)$_2$, —OC(=O)R$^{A1}$, —NR$^{A2}$C(=O)R$^{A2}$, —NR$^{A2}$C(=O)OR$^{A1}$, —NR$^{A2}$C(=O)N(R$^{A2}$)$_2$, —C(=NR$^{A2}$)N(R$^{A2}$)$_2$, —NR$^{A2}$C(=NR$^{A2}$)R$^{A2}$, —NR$^{A2}$C(=NR$^{A2}$)N(R$^{A2}$)$_2$, —SOR$^{A1}$, —SO$_2$R$^{A1}$, —NR$^{A2}$SO$_2$R$^{A1}$, —SO$_2$N(R$^{A2}$)$_2$, —CN, —SCN, and —NO$_2$, wherein each R$^{A1}$ is independently hydrogen, an amino protecting group, or an optionally substituted group selected from alkyl, alkenyl, alkynyl, carbocyclyl, heterocyclyl, aryl, and heteroaryl; and each R$^{A2}$ is independently hydrogen or an optionally substituted group selected from alkyl, alkenyl, alkynyl, carbocyclyl, heterocyclyl, aryl, and heteroaryl, or two R$^{A2}$ groups are taken together with their intervening atoms to form an optionally substituted heterocycle;

R$^A$ and R$^B$ are independently hydrogen, a hydroxyl protecting group, acyl, or optionally substituted alkyl;

R$^C$ is hydrogen, an amino protecting group, acyl, or optionally substituted alkyl; or two R$^C$ are taken together with their intervening atoms to form an optionally substituted heterocycle;

R$^D$ is hydrogen, an amino protecting group, acyl, or alkyl; or two R$^D$ are taken together with their intervening atoms to form an optionally substituted heterocycle;

n is 0, 1, 2, 3, or 4; and m is 0 or 1.

In another aspect, the compounds are generally of the formula:

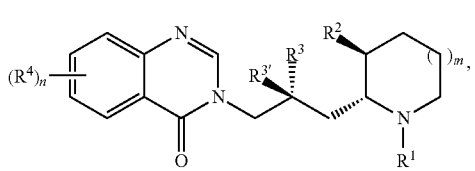

(III)

or a pharmaceutically acceptable salt thereof, wherein

R$^1$ is hydrogen, acyl, optionally substituted C$_{1-6}$ alkyl, or a protecting group;

R$^2$ is halogen, or an optionally substituted group selected from alkyl, alkenyl, alkynyl, —OR$^A$, —N(R$^C$)$_2$, —SR$^{A1}$, —C(=O)R$^{A1}$, —C(=O)OR$^{A1}$, —C(=O)N(R$^{A2}$)$_2$, —SOR$^{A1}$, —SO$_2$R$^{A1}$, —CN, and —CF$_3$;

R$^3$ is —OR$^B$;

R$^{3'}$ is C$_{1-6}$ alkyl, C$_{1-6}$ alkenyl, or C$_{1-6}$ alkynyl;

each R$^4$ is independently hydrogen, halogen, or an optionally substituted group selected from alkyl, alkenyl, alkynyl, carbocyclyl, heterocyclyl, aryl, heteroaryl, —OR$^{A1}$, —N(R$^{A2}$)$_2$, —SR$^{A1}$, —C(=O)R$^{A1}$, —C(=O)OR$^{A1}$, —C(=O)N(R$^{A2}$)$_2$, —OC(=O)R$^{A1}$, —NR$^{A2}$C(=O)R$^{A2}$, —NR$^{A2}$C(=O)OR$^{A1}$, —NR$^{A2}$C(=O)N(R$^{A2}$)$_2$, —C(=NR$^{A2}$)N(R$^{A2}$)$_2$, —NR$^{A2}$C(=NR$^{A2}$)R$^{A2}$—NR$^{A2}$C(=NR$^{A2}$)N(R$^{A2}$)$_2$, —SOR$^{A1}$, —SO$_2$R$^{A1}$, —NR$^{A2}$SO$_2$R$^{A1}$, —SO$_2$N(R$^{A2}$)$_2$, —CN, —SCN, and —NO$_2$;

each R$^{A1}$ is independently hydrogen, an amino protecting group, or an optionally substituted group selected from alkyl, alkenyl, alkynyl, carbocyclyl, heterocyclyl, aryl, and heteroaryl;

each R$^{A2}$ is independently hydrogen or an optionally substituted group selected from alkyl, alkenyl, alkynyl, carbocyclyl, heterocyclyl, aryl, and heteroaryl, or two R$^{A2}$ groups are taken together with their intervening atoms to form an optionally substituted heterocycle;

R$^A$ and R$^B$ are independently hydrogen, a hydroxyl protecting group, acyl, or optionally substituted alkyl;

R$^C$ is hydrogen, an amino protecting group, acyl, or optionally substituted alkyl; or two R$^C$ are taken together with their intervening atoms to form an optionally substituted heterocycle;

R$^D$ is hydrogen, an amino protecting group, acyl, or alkyl; or two R$^D$ are taken together with their intervening atoms to form an optionally substituted heterocycle;

n is 0, 1, 2, 3, or 4; and m is 0 or 1.

Without wishing to be bound by any particular theory, provided compounds are thought to act by binding in the active site of a tRNA synthetase (e.g., EPRS), thereby inhibiting the incorporation of proline into tRNA. The invention also provides methods of preparing the inventive compounds. Provided compounds may be prepared via a total synthesis from commercially available starting materials or may be prepared via a semi-synthetic process starting from a compound such as halofuginone or febrifugine. The present invention also provides methods for synthesizing halofuginol and derivatives thereof.

In another aspect, the present invention provides methods of treatment comprising administering a provided compound to a subject. Without wishing to be bound by a particular theory, the compounds of the present invention are thought to act by inhibiting glutamyl-prolyl tRNA synthetase (EPRS) or prolyl tRNA synthetase. Compounds of the present invention or pharmaceutical compositions thereof may be used to treat any disease including autoimmune diseases, such as multiple sclerosis, rheumatoid arthritis, lupus, psoriasis, scleroderma, or dry eye syndrome, inflammatory diseases, cardiovascular diseases, neurodegenerative diseases, protein aggregation disorders, and disorders involving angiogenesis, such as cancer, restenosis, macular degeneration, and choroidal neovascularization. Provided compounds may also be used to treat malaria. Provided compounds may also be used to treat T-cell neoplasms such as mature T-cell leukemias, nodal peripheral T-cell lymphomas (PTCL), extranodal PTCLs, and cutaneous T-cell lymphomas (CTCL). Compounds of the present invention may also be used to promote wound healing and/or prevent scarring and may be useful cosmetically, such as for the treatment or prevention of cellulite or stretch marks. Therefore, provided compounds may be used in cosmetic as well as pharmaceutical treatments. Compounds of the present invention may be used to treat or prevent disease in humans and other animals including domesticated animals. In certain embodiments, compounds of the present invention may be used to inhibit pro-fibrotic behavior in fibroblasts or inhibit the differentiation of Th17 cells. Therefore, provided compounds may be useful in preventing fibrosis. Provided compounds may also be used as probes of biological pathways. Provided compounds may also be used in studying the differentiation of T cells.

In some embodiments of a provided method, a second agent which inhibits expression or activity of a proinflammatory cytokine is administered to a subject. In some embodiments, a proinflammatory cytokine is selected from one or more of TNFα, IFNγ, GM-CSF, MIP-2, IL-12, IL-1α, IL-1β, and IL-23. In some embodiments of a provided method, a second agent that inhibits expression or activity of IL-6 or IL-21 is administered to the subject. In some embodiments, a second agent that inhibits TNFα is administered to the subject. In some embodiments, the agent that inhibits TNFα is an anti-TNFα antibody. In some embodiments, the agent that inhibits TNFα is a soluble TNF receptor. In other embodiments of a provided method, a second agent which is an immunomodulatory agent (e.g., steroids, non-steroidal anti-inflammatory agent, rapamycin, FK506, cyclosporine, HDAC inhibitors) is administered to the subject.

In another aspect, the present invention provides pharmaceutical and cosmetic compositions comprising provided compounds. Provided compositions may comprise an inventive compound in a therapeutically effective amount to suppress Th17 differentiation and/or treat or prevent autoimmune diseases, inflammatory diseases, cardiovascular diseases, neurodegenerative diseases, protein aggregation disorders, fibrosis, cellulite, stretch marks, malaria, or disorders involving angiogenesis, such as cancer, restenosis, macular degeneration, choroidal neovascularization, and T-cell neoplasms. Provided pharmaceutical compositions may optionally include a pharmaceutically acceptable excipient. Provided cosmetic compositions may optionally include a cosmetically acceptable excipient. In some embodiments, a provided pharmaceutical composition further comprises a second agent that inhibits expression or activity of a proinflammatory cytokine. In some embodiments, the proinflammatory cytokine is selected from one or more of IL-6, I-21, TNFα, IFNγ, GM-CSF, MIP-2, IL-12, IL-1α, IL-1β, and IL-23. Any mode of administration including oral, parenteral, inhalation, and topical administration of an inventive compound, or a pharmaceutical or cosmetic composition thereof, may be used.

References, scientific articles, patent applications, and patents cited in this application are incorporated herein by reference.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics,* 75th Ed., inside cover, and specific functional groups are generally defined as described therein. Additionally, general principles of organic chemistry, as well as specific functional moieties and reactivity, are described in *Organic Chemistry,* Thomas Sorrell, University Science Books, Sausalito, 1999; Smith and March *March's Advanced Organic Chemistry,* 5th Edition, John Wiley & Sons, Inc., New York, 2001; Larock, *Comprehensive Organic Transformations,* VCH Publishers, Inc., New York, 1989; Carruthers, *Some Modern Methods of Organic Synthesis,* 3rd Edition, Cambridge University Press, Cambridge, 1987.

The compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Where an isomer/enantiomer is preferred, it may, in some embodiments, be provided substantially free of the corresponding enantiomer, and may also be referred to as "optically enriched" or "enantiomerically enriched." "Optically enriched" and "enantiomerically enriched," as used herein, means that a provided compound is made up of a significantly greater proportion of one enantiomer. In certain embodiments, a compound of the present invention is made up of at least about 70% by weight of a preferred enantiomer. In certain embodiments, a compound of the present invention is made up of at least about 80% by weight of a preferred enantiomer. In certain embodiments, a compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972).

Unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

The terms "purified," "substantially purified," and "isolated" as used herein refer to a compound of the present invention being free of other, dissimilar compounds with which the compound of the invention is normally associated in its natural state, so that the compound of the present invention comprises at least 0.5%, 1%, 5%, 10%, 20%, 50%, 75%, 80%, 85%, 90%, 95%, 96%, 97%, 98%, 99%, 99.5%, 99.9% of the mass, by weight, of a given sample. In one preferred embodiment, these terms refer to the compound of the invention comprising at least 95% of the mass, by weight, of a given sample.

The term "acyl," as used herein, refers to a group having the general formula —C(=O)$R^{X1}$, —C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, and —C(=S)S($R^{X1}$), —C(=N$R^{X1}$)$R^{X1}$, —C(=N$R^{X1}$)O$R^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula (—OR$^i$), wherein R$^i$ is an optionally substituted acyl group, as defined herein, and the oxygen moiety is directly attached to the parent molecule.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substitutents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "amino," as used herein, refers to a group of the formula (—$NH_2$). A "substituted amino" refers either to a mono-substituted amine (—$NHR^h$) of a disubstituted amine (—$NR^h_2$), wherein the $R^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the $R^h$ substituents of the disubstituted amino group (—$NR^h_2$) form a 5- to 6-membered heterocyclic ring.

The term "alkoxy" refers to a "substituted hydroxyl" of the formula (—$OR^i$), wherein $R^i$ is an optionally substituted alkyl group, as defined herein, and the oxygen moiety is directly attached to the parent molecule.

The term "alkylthioxy" refers to a "substituted thiol" of the formula (—$SR^r$), wherein $R^r$ is an optionally substituted alkyl group, as defined herein, and the sulfur moiety is directly attached to the parent molecule.

The term "alkylamino" refers to a "substituted amino" of the formula (—$NR^h_2$), wherein $R^h$ is, independently, a hydrogen or an optionally substituted alkyl group, as defined herein, and the nitrogen moiety is directly attached to the parent molecule.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "arylalkyl," as used herein, refers to an aryl substituted alkyl group, wherein the terms "aryl" and "alkyl" are defined herein, and wherein the aryl group is attached to the alkyl group, which in turn is attached to the parent molecule. An exemplary arylalkyl group includes benzyl.

The term "aryloxy" refers to a "substituted hydroxyl" of the formula (—$OR^i$), wherein $R^i$ is an optionally substituted aryl group, as defined herein, and the oxygen moiety is directly attached to the parent molecule.

The term "arylamino," refers to a "substituted amino" of the formula (—$NR^h_2$), wherein $R^h$ is, independently, a hydrogen or an optionally substituted aryl group, as defined herein, and the nitrogen moiety is directly attached to the parent molecule.

The term "arylthioxy" refers to a "substituted thiol" of the formula (—$SR^r$), wherein $R^r$ is an optionally substituted aryl group, as defined herein, and the sulfur moiety is directly attached to the parent molecule.

The term "azido," as used herein, refers to a group of the formula (—$N_3$).

The term "cyano," as used herein, refers to a group of the formula (—CN).

The terms "halo" and "halogen" as used herein refer to an atom selected from fluorine (fluoro, —F), chlorine (chloro, —Cl), bromine (bromo, —Br), and iodine (iodo, —I).

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl," as used herein, refers to an alkyl moiety, as defined herein, which contain one or more oxygen, sulfur, nitrogen, phosphorus, or silicon atoms, e.g., in place of carbon atoms.

The term "heteroalkenyl," as used herein, refers to an alkenyl moiety, as defined herein, which contain one or more oxygen, sulfur, nitrogen, phosphorus, or silicon atoms, e.g., in place of carbon atoms.

The term "heteroalkynyl," as used herein, refers to an alkynyl moiety, as defined herein, which contain one or more oxygen, sulfur, nitrogen, phosphorus, or silicon atoms, e.g., in place of carbon atoms.

The term "heteroalkylamino" refers to a "substituted amino" of the formula (—NR$^h{}_2$), wherein R$^h$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula (—OR$^i$), wherein R$^i$ is an optionally substituted heteroalkyl group, as defined herein, and the oxygen moiety is directly attached to the parent molecule.

The term "heteroalkylthioxy" refers to a "substituted thiol" of the formula (—SR$^r$), wherein R$^r$ is an optionally substituted heteroalkyl group, as defined herein, and the sulfur moiety is directly attached to the parent molecule.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 12-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylamino" refers to a "substituted amino" of the (—NR$^h{}_2$), wherein R$^h$ is, independently, a hydrogen or an optionally substituted heteroaryl group, as defined herein, and the nitrogen moiety is directly attached to the parent molecule.

The term "heteroaryloxy" refers to a "substituted hydroxyl" of the formula (—OR$^i$), wherein R$^i$ is an optionally substituted heteroaryl group, as defined herein, and the oxygen moiety is directly attached to the parent molecule.

The term "heteroarylthioxy" refers to a "substituted thiol" of the formula (—SR$^r$), wherein R$^r$ is an optionally substituted heteroaryl group, as defined herein, and the sulfur moiety is directly attached to the parent molecule.

The term "hydroxy," or "hydroxyl," as used herein, refers to a group of the formula (—OH). A "substituted hydroxyl" refers to a group of the formula (—OR$^i$), wherein R$^i$ can be any substitutent which results in a stable moiety (e.g., a suitable hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "imino," as used herein, refers to a group of the formula (=NR$^r$), wherein R$^r$ corresponds to hydrogen or any substituent as described herein, that results in the formation of a stable moiety (for example, a suitable amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted). In certain embodiments, imino refers to =NH wherein R$^r$ is hydrogen.

The term "isocyano," as used herein, refers to a group of the formula (—NC).

The term "nitro," as used herein, refers to a group of the formula (—NO$_2$).

The term "oxo," as used herein, refers to a group of the formula (=O).

The term "stable moiety," as used herein, preferably refers to a moiety which possess stability sufficient to allow manufacture, and which maintains its integrity for a sufficient period of time to be useful for the purposes detailed herein.

A "protecting group," as used herein, is well known in the art and include those described in detail in Greene's Protective Groups in Organic Synthesis, P. G. M. Wuts and T. W. Greene, 4$^{th}$ edition, Wiley-Interscience, 2006, the entirety of which is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl) propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "suitable hydroxyl protecting group" as used herein, is well known in the art and includes those described in detail in Greene (1999). Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxyl)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "subject," as used herein, refers to any animal. In certain embodiments, the subject is a mammal. In certain embodiments, the term "subject", as used herein, refers to a human (e.g., a man, a woman, or a child).

The terms "administer," "administering," or "administration," as used herein refers to implanting, absorbing, ingesting, injecting, or inhaling the inventive compound.

As used herein, the terms "treatment," "treat," and "treating" refer to reversing, alleviating, delaying the onset of, or inhibiting the progress of a disease or disorder, or one or more symptoms thereof, described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to delay or prevent recurrence.

The terms "effective amount" and "therapeutically effective amount," as used herein, refer to the amount or concentration of an inventive compound, that, when administered to a subject, is effective to at least partially treat a condition from which the subject is suffering (e.g., chronic inflammatory disease, autoimmune disease, dry eye syndrome, fibrosis, scar formation, angiogenesis, viral infection, malaria, ischemic damage, transplant and implant rejection, neurodegenerative disease, or a cosmetic indication).

DETAILED DESCRIPTION OF CERTAIN EMBODIMENTS OF THE INVENTION

Figure 1:
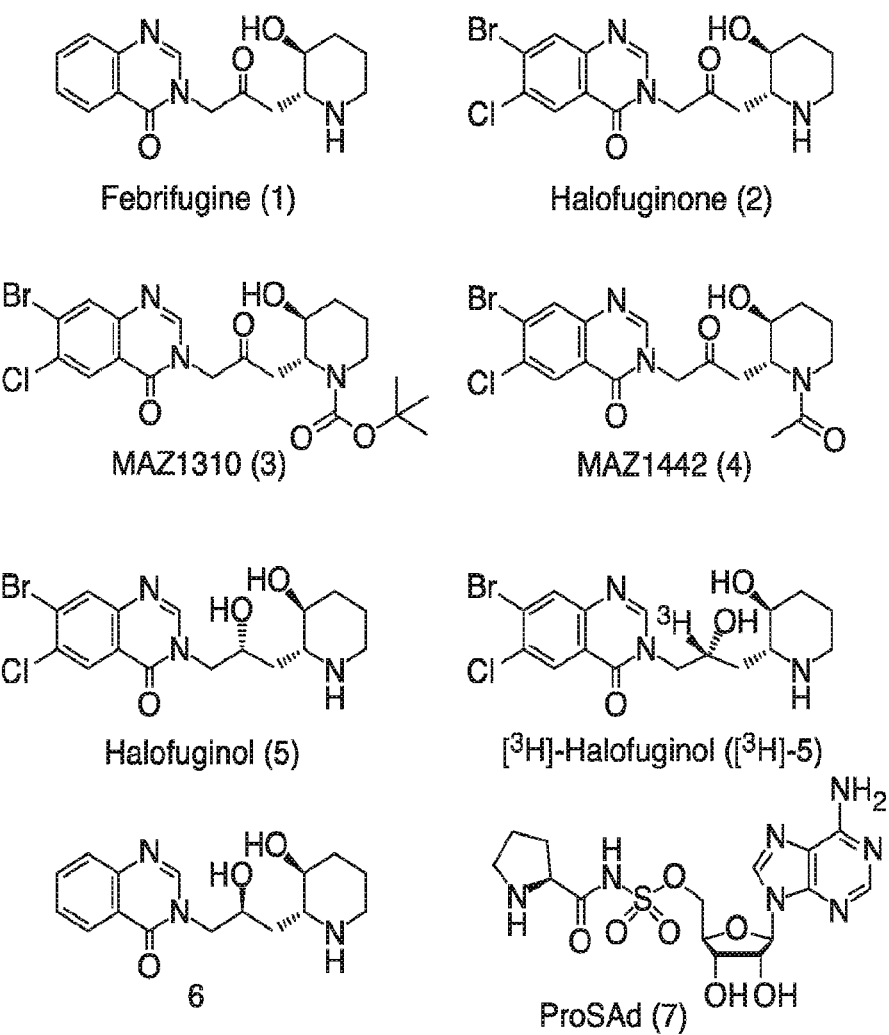
FIG. 1 shows chemical structures of certain exemplary compounds. Except where otherwise specified halofuginone and derivatives were used as racemates.

Plant bioactives are both historically important therapeutics and a valuable source of new drugs (Clardy et al. *Nature* 432:829-37 (2004)). Approximately a third of the top 20 drugs on the market today are derived from natural products (Howitz et al. *Cell* 133:387-91 (2008)), the majority of these being derived from plants. The plant alkaloid febrifugine (1; FIG. 1) is the active ingredient found in the roots of Blue Evergreen Hydrangea, *Dichroa febrifuga* Lour (Coatney et al. *J. Natl. Malar. Soc.* 9:183-6 (1950)). During the roughly 2000 years of its therapeutic usage, the molecular mechanism of febrifugine in animal tissues has remained unknown. Historically recognized for its antiprotozoal activity, this herbal extract was used as an antimalarial remedy in traditional Chinese medicine. Halofuginone (HF) (2; FIG. 1), a racemic halogenated derivative of febrifugine, was synthesized in a search of a less-toxic form of this plant bioactive (Ryley et al. *Adv. Pharmacol. Chemother.* 11:221-93 (1973)). In the last two decades, HF has gained attention, and progressed to phase 2 clinical trials for its potential as a therapeutic in cancer and fibrotic disease (Pines et al. *Gen. Pharmacol.* 30:445-50 (1998); Elkin et al. *Cancer Res.* 59:4111-8 (1999); McGaha et al. *Autoimmunity* 35:277-82 (2002); Pines et al. *Biol. Blood Marrow Transplant* 9:417-25 (2003); Koon et al. *J. Acquir. Immune Defic. Syndr.* 56:64-8 (2010)). HF potently inhibits the differentiation of pro-inflammatory Th17 cells, in vitro and in vivo, through activation of the nutrient-sensing amino acid response (AAR) pathway (Sundrud et al. *Science* 324:1334-8 (2009)).

Figure 7:
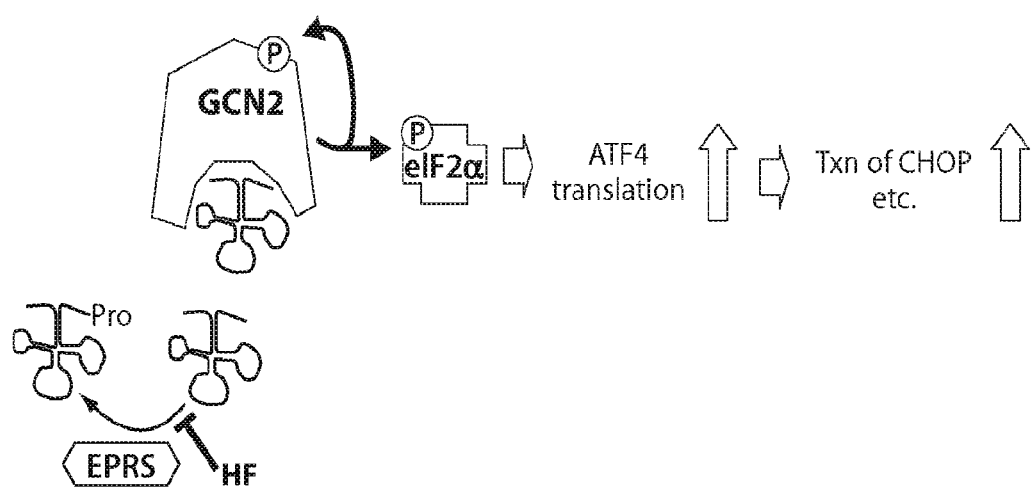
FIG. 7 depicts a model of AAR activation by inhibition of tRNA charging.

An important subset of natural product bioactives regulates highly conserved stress response pathways that are control points in cellular metabolism, such as the AMPK and TOR pathways, to confer therapeutic benefits in mammalian cells (Howitz et al. *Cell* 133:387-91 (2008); Grohmann et al. *Immunol Rev.* 236:243-64 (2010); Cobbold et al. *Proc. Natl. Acad. Sci. USA* 106:12055-60 (2009); Finlay et al. *Nat. Rev. Immunol.* 11:109-17 (2011)). Less studied than the mTOR and AMPK pathways, the AAR pathway is conserved throughout eukaryotes as a cytoprotective response to nutrient limitation (Kilberg et al. *Annu. Rev. Nutr.* 25:59-85 (2005)). Amino acid restriction results in the accumulation of uncharged tRNAs that bind to and activate the protein kinase GCN2 (FIG. 7). GCN2 activation results in its autophosphorylation, as well as phosphorylation of the translational initiation factor eIF2a, a shared component of multiple cellular stress response pathways that are collectively referred to as the integrated stress response (ISR) (Harding et al. *Mol. Cell.* 11:619-33 (2003)). Phosphorylation of eIF2a leads to a transient reduction in the initiation of mRNA cap-dependent translation, with a concomitant increase in cap-independent translation of a subset of mRNAs, including the mRNA encoding the transcription factor ATF4 (Harding et al. *Mol. Cell.* 6:1099-108 (2000)). Increased levels of ATF4 result in the activation of a set of genes that mediate the adaptation of cells to a stress environment, among them is the gene encoding the transcription factor C/EBP homologous protein (CHOP) (Kilberg et al. *Annu. Rev. Nutr.* 25:59-85 (2005)). In eukaryotic cells, the AAR and mTORC1 pathways both play a role in sensing nutrient status and activating cellular programs that mitigate restriction in the supply of environmental amino acids. These metabolic stress pathways are differentially activated, however, eliciting distinct sets of transcriptional responses and biological effects (Peng et al. *Mol. Cell. Biol.* 22:5575-84 (2002); Deval et al. *Febs J.* 276:707-18 (2009); Palii et al. *Amino Acids* (2008)). In contrast to the AAR, the mTORC1 pathway is inhibited by amino acid restriction, and is thought to sense amino acid levels directly (Sancak et al. *Science* 320:1496-501 (2008)). AAR pathway activation, on the other hand, is triggered by the intracellular accumulation of uncharged tRNAs that can result from insufficiency of any amino acid, or from the inhibition of any of the aminoacyl tRNA synthetases (Harding et al. *Mol. Cell.* 11:619-33 (2003)).

Metabolic sensor pathways that respond to changes in environmental levels of energy metabolites and nutrients, such as the AMPK, TOR, and AAR pathways, have become important drug targets in cancer (Zoncu et al. *Nat. Rev. Mol. Cell Biol.* 12:21-35 (2011)), inflammatory diseases (Powell et al. *Immunity* 33:301-11 (2010); Hotamisligil et al. *Nat. Rev. Immunol.* 8:923-34 (2008)), and autoimmune disease (Esposito et al. *J. Neuroimmunol.* 220:52-63; Nath et al. *J. Immunol.* 182:8005-14 (2009)). Our recent work shows that HF inhibits the development of disease in a mouse model of Th17-driven multiple sclerosis by activation of the AAR pathway (Sundrud et al. *Science* 324:1334-8 (2009)). Despite intense interest in the broad therapeutic potential of febrifugine-derived compounds, their development for clinical use has been hindered by the lack of knowledge regarding its molecular mechanism of action. We have shown that febrifugine and its derivatives activate the AAR by directly inhibiting the prolyl tRNA synthetase activity of glutamyl-prolyl tRNA synthetase (EPRS). We show that febrifugine derivatives compete with proline for the prolyl tRNA synthetase (PRS) active site, causing the accumulation of uncharged tRNA$^{pro}$, and mimicking reduced cellular proline availability. We further show that addition of exogenous proline reverses a broad range of HF-induced cellular effects, indicating that EPRS-inhibition underlies the therapeutic activities of febrifugine derivatives.

The present invention provides halofuginol and analogs having a particular stereochemistry. Compounds of the present invention are useful in the treatment of disorders associated with glutamyl-prolyl tRNA synthetase (EPRS) inhibition, Th17 differentiation, and amino acid starvation response (AAR) induction, such as chronic inflammation, fibrosis, autoimmune diseases, scarring, angiogenesis, transplant, implant, or device rejection, ischemic damage, viral infections, and neurodegenerative disorders. The compounds may also be used in treating protozoal infections such as malaria by inhibiting the prolyl tRNA synthetase of the protozoa. The present invention also provides pharmaceutical and cosmetic compositions and methods of using the inventive compounds for the treatment of various diseases and conditions (e.g., chronic inflammation, fibrosis, autoimmune diseases, scarring, angiogenesis, transplant, implant, or device rejection, ischemic damage, viral infections, protozoal infections, and neurodegenerative disorders), as well as methods for synthesizing inventive compounds.

Compounds

Compounds of the present invention include halofuginol and derivatives thereof. Compounds provided herein have been found to have surprising biological activity and/or stability. In some embodiments, compounds of the invention inhibit tRNA synthetase. In particular, compounds of the present invention inhibit glutamyl-prolyl tRNA synthetase (EPRS) (e.g., mammalian EPRS, human EPRS). In certain embodiments, compounds of the present invention inhibit non-metazoan prolyl tRNA synthetase (e.g., protozoal prolyl tRNA synthease). In certain embodiments, provided compounds suppress the differentiation of a subset of effector T-cells (i.e., Th17 cells). In certain embodiments, provided compound suppress IL-17 production. In certain embodiments, provided compounds activate the amino acid starvation response (AAR).

The biological activity of provided compounds makes them useful in the treatment of a variety of diseases and conditions. For example, in certain embodiments, inventive compounds are useful in the treatment of diseases and conditions associated with IL-17 production, such as arthritis, inflammatory bowel disease, psoriasis, multiple sclerosis, lupus, asthma, dry eye syndrome, and other autoimmune and/or inflammatory diseases. In certain other embodiments, compounds of the present invention suppress pro-fibrotic gene expression; therefore, they are useful in treating or preventing fibrosis. In some embodiments, provided compounds are useful in treating or preventing cellulite. In some embodiments, compounds of the present invention inhibit viral gene expression, replication, and maturation. In other embodiments, compounds of the present invention protect organs from stress. In certain embodiments, provided compounds suppress the synthesis of toxic proteins such as polyglutamine-containing proteins that cause neurodegenerative diseases such as Huntington's disease. In some embodiments, provided compounds promote autophagy. In certain embodiments, provided compounds inhibit the synthesis of proline-rich proteins such as collagen. In certain other embodiments, provided compounds inhibit angiogenesis. In certain embodiments, provided compounds are useful for treating protozoal infections.

In certain embodiments, compounds of the present invention have an $IC_{50}$ with respect to inhibition of a tRNA synthetase of less than approximately 10 µM, e.g., less than approximately 1 µM, e.g., less than approximately 0.1 µM, or e.g., less than approximately 0.01 µM. In certain embodiments, the tRNA synthetase is ProRS. In certain embodiments, the tRNA synthetase is EPRS. In certain embodiments, compounds of the present invention have an $IC_{50}$ with respect to activation of AAR of less than approximately 10 µM, e.g., less than approximately 1 µM, e.g., less than approximately 0.1 µM, or e.g., less than approximately 0.01 µM. Provided compounds are useful in the treatment of a variety of diseases. Certain compounds of the present invention are useful in treating inflammatory diseases or autoimmune diseases, such as inflammatory bowel disease, multiple sclerosis, rheumatoid arthritis, lupus, psoriasis, scleroderma, or dry eye syndrome. In certain embodiments, provided compounds are useful in the treatment of cardiovascular diseases, diseases involving angiogenesis, neurodegenerative diseases, or protein aggregation disorders. In certain embodiments, provided compounds are useful in the treatment of T-cell neoplasms such as mature T-cell leukemias, nodal peripheral T-cell lymphomas (PTCL), extranodal PTCLs, and cutaneous T-cell lymphomas (CTCL). Certain compounds of the present invention are also useful as anti-scarring agents. In some embodiments, inventive compounds are useful in treating viral infections. In other embodiments, provided compounds are useful in the treatment or prevention of restenosis.

In certain embodiments, an inventive compound is less toxic than halofuginone, febrifugine, or other related natural products. In certain other embodiments, an inventive compound is more potent with respect to inhibiting a tRNA synthetase than halofuginone, febrifugine, or other related natural products. In some embodiments, the tRNA synthetase is ProRS. In some embodiments, the tRNA synthetase is EPRS. In certain other embodiments, an inventive compound is more potent with respect to activating AAR than halofuginone, febrifugine, or other related natural products. In yet other embodiments, an inventive compound is more stable than halofuginone, febrifugine, or other related natural products. Inventive compounds may have one or more characteristics that make the compound more suitable for use as a pharmaceutical or cosmetic agent. In some embodiments, an inventive compound displays improved physicochemical properties when compared with halofuginone, febrifugine, or other related natural products. In some embodiments, an inventive compound displays improved drug metabolism/pharmacokinetic properties when compared with halofuginone, febrifugine, or other related natural products. In certain embodiments, an inventive compound is more soluble than halofuginone, febrifugine, or other related natural products. In certain embodiments, an inventive compound is more soluble in water than halofuginone, febrifugine, or other related natural products.

Compounds of the present invention include asymmetric centers. In some embodiments, the present invention includes racemates (i.e., equal amounts of the stereochemistry shown in Formula (I) as well as the mirror image). In some embodiments, a provided compound is substantially enriched with one diasteromer. In some embodiments, a provided compound is substantially enriched with one enantiomer. Such isomers can be obtained by purification techniques and/or by stereochemically controlled synthesis.

In some embodiments, an inventive compound is generally of the formula:

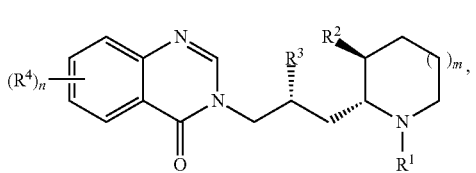

(I)

or a pharmaceutically acceptable salt thereof,
wherein $R^1$ is hydrogen, acyl, optionally substituted $C_{1-6}$ alkyl, or a protecting group;

$R^2$ is halogen, or an optionally substituted group selected from alkyl, alkenyl, alkynyl, —$OR^A$, —$N(R^C)_2$, —$SR^{A1}$, —$C(=O)R^{A1}$, —$C(=O)OR^{A1}$, —$C(=O)N(R^{A2})_2$, —$SOR^{A1}$, —$SO_2R^{A1}$, —CN, and —$CF_3$;

$R^3$ is halogen, or an optionally substituted group selected from alkyl, alkenyl, alkynyl, —$OR^B$, —$N(R^D)_2$, —$SR^{A1}$, —$C(=O)R^{A1}$, —$C(=O)OR^{A1}$, —$C(=O)N(R^{A2})_2$, —$SOR^{A1}$, —$SO_2R^{A1}$, —CN, and —$CF_3$;

each $R^4$ is independently hydrogen, halogen, or an optionally substituted group selected from alkyl, alkenyl, alkynyl, carbocyclyl, heterocyclyl, aryl, heteroaryl, —$OR^{A1}$, —$N(R^{A2})_2$, —$SR^{A1}$, —$C(=O)R^{A1}$, —$C(=O)OR^{A1}$, —$C(=O)N(R^{A2})_2$, —$OC(=O)R^{A1}$, —$NR^{A2}C(=O)R^{A2}$, —$NR^{A2}C(=O)OR^{A1}$, —$NR^{A2}C(=O)N(R^{A2})_2$, —$C(=NR^{A2})N(R^{A2})_2$, —$NR^{A2}C(=NR^{A2})R^{A2}$ —$NR^{A2}C(=NR^{A2})N(R^{A2})_2$, —$SOR^{A1}$, —$SO_2R^{A1}$, —$NR^{A2}SO_2R^{A1}$, —$SO_2N(R^{A2})_2$, —CN, —SCN, and —$NO_2$;

each $R^{A1}$ is independently hydrogen, an amino protecting group, or an optionally substituted group selected from alkyl, alkenyl, alkynyl, carbocyclyl, heterocyclyl, aryl, and heteroaryl;

each $R^{A2}$ is independently hydrogen or an optionally substituted group selected from alkyl, alkenyl, alkynyl, carbocyclyl, heterocyclyl, aryl, and heteroaryl, or two $R^{A2}$ groups are taken together with their intervening atoms to form an optionally substituted heterocycle;

$R^A$ and $R^B$ are independently hydrogen, a hydroxyl protecting group, acyl, or optionally substituted alkyl;

$R^C$ is hydrogen, an amino protecting group, acyl, or optionally substituted alkyl; or two $R^C$ are taken together with their intervening atoms to form an optionally substituted heterocycle;

$R^D$ is hydrogen, an amino protecting group, acyl, or alkyl; or two $R^D$ are taken together with their intervening atoms to form an optionally substituted heterocycle;

n is 0, 1, 2, 3, or 4; and m is 0 or 1.

In certain embodiments, the present invention provides a compound of Formula (II):

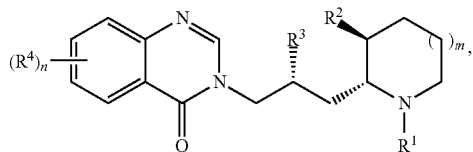

(II)

or a pharmaceutically acceptable salt thereof,
wherein $R^1$ is hydrogen, acyl, optionally substituted $C_{1-6}$ alkyl, or a protecting group;

$R^2$ is —$OR^A$ or —$N(R^C)_2$;

$R^3$ is —$OR^B$ or —$N(R^D)_2$;

each $R^4$ is independently hydrogen, halogen, or an optionally substituted group selected from alkyl, alkenyl, alkynyl, carbocyclyl, heterocyclyl, aryl, heteroaryl, —$OR^{A1}$, —$N(R^{A2})_2$, —$SR^{A1}$, —$C(=O)R^{A1}$, —$C(=O)OR^{A1}$, —$C(=O)N(R^{A2})_2$, —$OC(=O)R^{A1}$, —$NR^{A2}C(=O)R^{A2}$, —$NR^{A2}C(=O)OR^{A1}$, —$NR^{A2}C(=O)N(R^{A2})_2$, —$C(=NR^{A2})N(R^{A2})_2$, —$NR^{A2}C(=NR^{A2})R^{A2}$ —$NR^{A2}C(=NR^{A2})N(R^{A2})_2$, —$SOR^{A1}$, —$SO_2R^{A1}$, —$NR^{A2}SO_2R^{A1}$, —$SO_2N(R^{A2})_2$, —CN, —SCN, and —$NO_2$, wherein each $R^{A1}$ is independently hydrogen, an amino protecting group, or an optionally substituted group selected from alkyl, alkenyl, alkynyl, carbocyclyl, heterocyclyl, aryl, and heteroaryl; and each $R^{A2}$ is independently hydrogen or an optionally substituted group selected from alkyl, alkenyl, alkynyl, carbocyclyl, heterocyclyl, aryl, and heteroaryl, or two $R^{A2}$ groups are taken together with their intervening atoms to form an optionally substituted heterocycle;

$R^A$ and $R^B$ are independently hydrogen, a hydroxyl protecting group, acyl, or optionally substituted alkyl;

$R^C$ is hydrogen, an amino protecting group, acyl, or optionally substituted alkyl; or two $R^C$ are taken together with their intervening atoms to form an optionally substituted heterocycle;

$R^D$ is hydrogen, an amino protecting group, acyl, or alkyl; or two $R^D$ are taken together with their intervening atoms to form an optionally substituted heterocycle;

n is 0, 1, 2, 3, or 4; and m is 0 or 1.

In certain embodiments, a provided compound is of the formula:

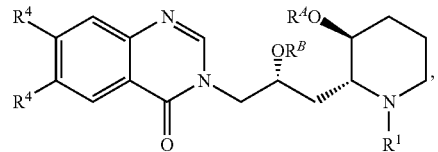

or a pharmaceutically acceptable salt thereof, wherein $R^1$, $R^4$, $R^A$, and $R^B$ are as described herein.

In certain embodiments, a provided compound is of the formula:

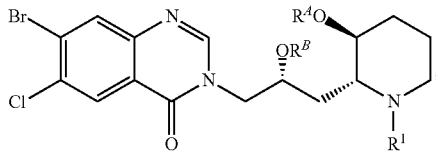

or a pharmaceutically acceptable salt thereof, wherein $R^1$, $R^A$, and $R^B$ are as described herein.

In certain embodiments, a provided compound is of the formula:

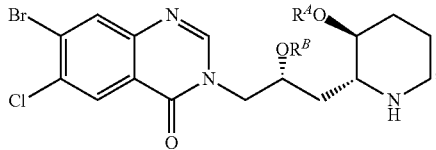

or a pharmaceutically acceptable salt thereof, wherein $R^A$ and $R^B$ are as described herein.

In certain embodiments, a provided compound is of the formula:

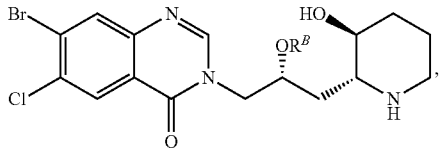

or a pharmaceutically acceptable salt thereof, wherein $R^B$ is as described herein.

In certain embodiments, a provided compound is of the formula:

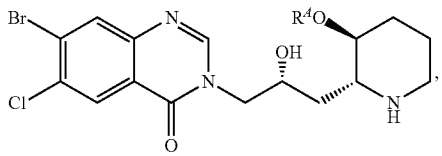

or a pharmaceutically acceptable salt thereof, wherein $R^A$ is as described herein.

In certain embodiments, a provided compound is of the formula:

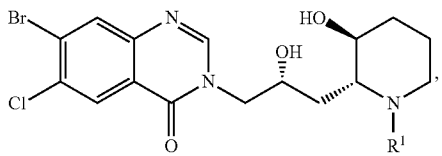

or a pharmaceutically acceptable salt thereof, wherein $R^1$ is as described herein.

In certain embodiments, a provided compound is of the formula:

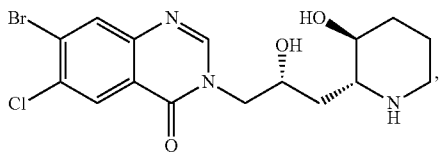 [SMILES: O=c1c2cc(Cl)c(Br)cc2ncn1C[C@H](O)C[C@H]1NCCC[C@@H]1O]

or a pharmaceutically acceptable salt thereof.

In certain embodiments, a provided compound is of the formula:

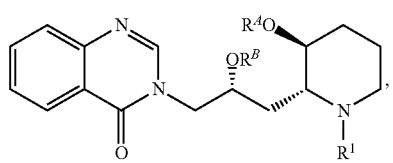

or a pharmaceutically acceptable salt thereof, wherein $R^1$, $R^A$, and $R^B$ are as described herein.

In certain embodiments, a provided compound is of the formula:

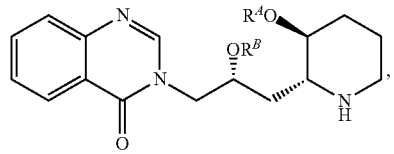

or a pharmaceutically acceptable salt thereof, wherein $R^A$ and $R^B$ are as described herein.

In certain embodiments, a provided compound is of the formula:

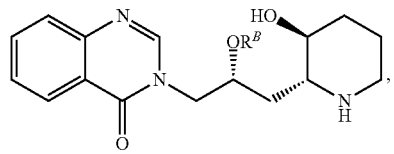

or a pharmaceutically acceptable salt thereof, wherein $R^B$ is as described herein.

In certain embodiments, a provided compound is of the formula:

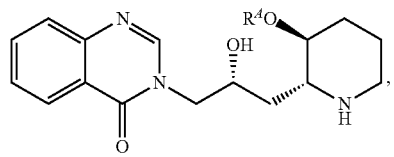

or a pharmaceutically acceptable salt thereof, wherein $R^A$ is as described herein.

In certain embodiments, a provided compound is of the formula:

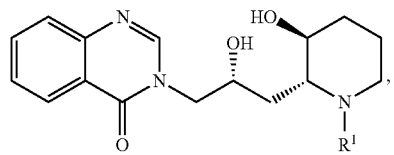

or a pharmaceutically acceptable salt thereof, wherein $R^1$ is as described herein.

In certain embodiments, a provided compound is of the formula:

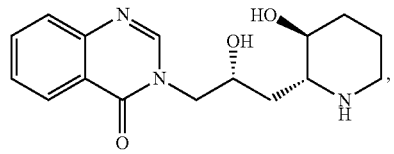 [SMILES: O=c1c2ccccc2ncn1C[C@H](O)C[C@H]1NCCC[C@@H]1O]

or a pharmaceutically acceptable salt thereof.

In certain embodiments, the present invention provides a compound of Formula (III):

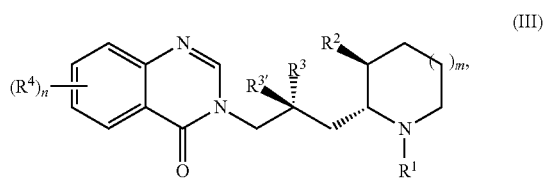

(III)

or a pharmaceutically acceptable salt thereof,
wherein
$R^1$ is hydrogen, acyl, optionally substituted $C_{1-6}$ alkyl, or a protecting group;

$R^2$ is halogen, or an optionally substituted group selected from alkyl, alkenyl, alkynyl, —$OR^A$, —$N(R^C)_2$, —$SR^{A1}$, —$C(=O)R^{A1}$, —$C(=O)OR^{A1}$, —$C(=O)N(R^{A2})_2$, —$SOR^{A1}$, —$SO_2R^{A1}$, —CN, and —$CF_3$;

$R^3$ is —$OR^B$;

$R^{3'}$ is $C_{1-6}$ alkyl, $C_{1-6}$ alkenyl, or $C_{1-6}$ alkynyl;

each $R^4$ is independently hydrogen, halogen, or an optionally substituted group selected from alkyl, alkenyl, alkynyl, carbocyclyl, heterocyclyl, aryl, heteroaryl, —$OR^{A1}$, —$N(R^{A2})_2$, —$SR^{A1}$, —$C(=O)R^{A1}$, —$C(=O)OR^{A1}$, —$C(=O)N(R^{A2})_2$, —$OC(=O)R^{A1}$, —$NR^{A2}C(=O)R^{A2}$, —$NR^{A2}C(=O)OR^{A1}$, —$NR^{A2}C(=O)N(R^{A2})_2$, —$C(=NR^{A2})N(R^{A2})_2$, —$NR^{A2}C(=NR^{A2})R^{A2}$—$NR^{A2}C(=NR^{A2})N(R^{A2})_2$, —$SOR^{A1}$, —$SO_2R^{A1}$, —$NR^{A2}SO_2R^{A1}$, —$SO_2N(R^{A2})_2$, —CN, —SCN, and —$NO_2$;

each $R^{A1}$ is independently hydrogen, an amino protecting group, or an optionally substituted group selected from alkyl, alkenyl, alkynyl, carbocyclyl, heterocyclyl, aryl, and heteroaryl;

each $R^{A2}$ is independently hydrogen or an optionally substituted group selected from alkyl, alkenyl, alkynyl, carbocyclyl, heterocyclyl, aryl, and heteroaryl, or two $R^{A2}$ groups are taken together with their intervening atoms to form an optionally substituted heterocycle;

$R^A$ and $R^B$ are independently hydrogen, a hydroxyl protecting group, acyl, or optionally substituted alkyl;

$R^C$ is hydrogen, an amino protecting group, acyl, or optionally substituted alkyl; or two $R^C$ are taken together with their intervening atoms to form an optionally substituted heterocycle;

n is 0, 1, 2, 3, or 4; and m is 0 or 1.

In some embodiments, a provided compound is a racemic mixture. In certain embodiments, a provided compound contains less than 50%, less than 40%, less than 30%, less than 25%, less than 20%, less than 15%, less than 10%, less than 5%, less than 4%, less than 3%, less than 2%, less than 1%, less than 0.5% of a diastereomer that is not of Formula (I). In other embodiments, a provided compound is enantiomerically enriched. In certain embodiments, a provided compound is at least 50% ee, 60% ee, 70% ee, 80% ee, 85% ee, 90% ee, 95% ee, 96% ee, 97% ee, 98% ee, 99% ee, 99.5% ee, 99.9% ee.

In some embodiments, a provided compound is isolated.

In some embodiments, at least one $R^4$ is not hydrogen.

In some embodiments, a provided compound is febrifuginol. In some embodiments, a provided compound is not febrifuginol. In some embodiments, a provided compound is halofuginol. In some embodiments, a provided compound is not halofuginol.

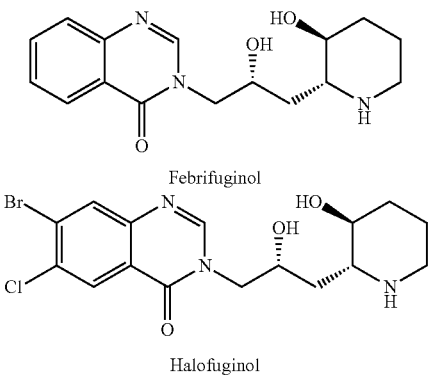

Febrifuginol

Halofuginol

As defined generally above, $R^1$ is hydrogen, acyl, optionally substituted $C_{1-6}$ alkyl, or a protecting group. In some embodiments, $R^1$ is hydrogen. In some embodiments, $R^1$ is a protecting group. In some embodiments, $R^1$ is tert-butoxycarbonyl. In other embodiments, $R^1$ is benzyloxycarbonyl, alkyloxycarbonyl, or allyloxycarbonyl. In certain embodiments, $R^1$ is benzyl. In some embodiments, $R^1$ is acyl. In some embodiments, $R^1$ is $C_{1-6}$ acyl. In some embodiments, $R^1$ is $C_{1-3}$ acyl. In certain embodiments, $R^1$ is acetyl. In other embodiments, $R^1$ is $C_{1-6}$ alkyl. In certain embodiments, $R^1$ is methyl, ethyl, propyl, or butyl. In certain embodiments, $R^1$ is not hydrogen, and the compound is a prodrug wherein the $R^1$ group is cleaved to give an active metabolite in which $R^1$ is hydrogen. Such a prodrug could be useful for minimizing intestinal toxicity.

As defined generally above for formulae (I) and (III), $R^2$ is halogen, or an optionally substituted group selected from alkyl, alkenyl, alkynyl, —$OR^A$, —$N(R^C)_2$, —$SR^{A1}$, —$C(=O)R^{A1}$, —$C(=O)OR^{A1}$, —$C(=O)N(R^{A2})_2$, —$SOR^{A1}$, —$SO_2R^{A1}$, —CN, and —$CF_3$. In certain embodiments, $R^2$ is —$OR^A$ or —$N(R^C)_2$. In certain embodiments, $R^2$ is halogen. In certain embodiments, $R^2$ is alkyl, alkenyl, or alkynyl. In certain embodiments, $R^2$ is —$SR^{A1}$, —$SOR^{A1}$, or —$SO_2R^{A1}$. In certain embodiments, $R^2$ is —CN. In certain embodiments, $R^2$ is —$CF_3$. In certain embodiments, $R^2$ is —$C(=O)R^{A1}$, —$C(=O)OR^{A1}$, or —$C(=O)N(R^{A2})_2$.

As defined generally above for formula (II), $R^2$ is —$OR^A$ or —$N(R^C)_2$. In some embodiments, $R^2$ is —$OR^A$. In certain embodiments, $R^2$ is —OH. In certain embodiments, $R^2$ is —Oacyl. In certain embodiments, $R^2$ is —Oalkyl. In certain other embodiments, $R^2$ is —$OR^A$, wherein $R^A$ is $C_{1-6}$ alkyl or $C_{1-6}$ acyl. In certain embodiments, $R^2$ is —$OCH_3$, —$OCH_2CH_3$, or —OAc. In certain other embodiments, $R^2$ is —$OR^A$, wherein $R^A$ is a hydroxyl protecting group. In some embodiments, $R^2$ is —$N(R^C)_2$. In certain embodiments, $R^2$ is —$NHR^C$. In certain embodiments, $R^2$ is —$NH_2$. In certain other embodiments, $R^2$ is —$N(R^C)_2$, wherein $R^C$ is H, $C_{1-6}$ alkyl, or $C_{1-6}$ acyl. In certain embodiments, $R^2$ is —$NHR^C$, wherein $R^C$ is $C_{1-6}$ alkyl or $C_{1-6}$ acyl. In certain embodiments, $R^2$ is —NHAc, —$NHCH_3$, or —$NHCH_2CH_3$. In certain other embodiments, $R^2$ is —$N(R^C)_2$, wherein $R^C$ is an amino protecting group.

As defined generally above for formula (I), $R^3$ is halogen, or an optionally substituted group selected from alkyl, alkenyl, alkynyl, —$OR^B$, —$N(R^D)_2$, —$SR^{A1}$, —$C(=O)R^{A1}$, —$C(=O)OR^{A1}$, —$C(=O)N(R^{A2})_2$, —$SOR^{A1}$, —$SO_2R^{A1}$, —CN, and —$CF_3$. In certain embodiments, $R^3$ is —$OR^B$ or —$N(R^D)_2$. In certain embodiments, $R^3$ is halogen. In certain embodiments, $R^3$ is alkyl, alkenyl, or alkynyl. In certain embodiments, $R^3$ is —$SR^{A1}$, —$SOR^{A1}$, or —$SO_2R^{A1}$. In certain embodiments, R³ is —CN. In certain embodiments, R³ is —CF₃. In certain embodiments, R³ is —C(=O)R^{A1}, C(=O)OR^{A1}, or —C(=O)N(R^{A2})₂.

As defined generally above for formula (II), R³ is —OR^B or —N(R^D)₂. In some embodiments, R³ is —OR^B. In certain embodiments, R³ is —OH. In certain embodiments, R³ is —Oacyl. In certain embodiments, R³ is —Oalkyl. In certain other embodiments, R³ is —OR^B, wherein R^B is C_{1-6} alkyl or C_{1-6} acyl. In certain embodiments, R³ is —OCH₃, —OCH₂CH₃, or —OAc. In certain other embodiments, R³ is —OR^B, wherein R^B is a hydroxyl protecting group. In some embodiments, R³ is —N(R^D)₂. In certain embodiments, R³ is —NHR^D. In certain embodiments, R³ is —NH₂. In certain other embodiments, R³ is —N(R^D)₂, wherein R^D is H, C_{1-6} alkyl, or C_{1-6} acyl. In certain embodiments, R³ is —NHR^D, wherein R^D is C_{1-6} alkyl or C_{1-6} acyl. In certain embodiments, R³ is —NHAc, —NHCH₃, or —NHCH₂CH₃. In certain other embodiments, R³ is —N(R^D)₂, wherein R^D is an amino protecting group.

As defined generally above for formula (III), R³ is —OR^B. In certain embodiments, R³ is —OH. In certain embodiments, R³ is —Oacyl. In certain embodiments, R³ is —Oalkyl. In certain other embodiments, R³ is —OR^B, wherein R^B is C_{1-6} alkyl or C_{1-6} acyl. In certain embodiments, R³ is —OCH₃, —OCH₂CH₃, or —OAc. In certain other embodiments, R³ is —OR^B, wherein R^B is a hydroxyl protecting group.

As defined generally above for formula (III), R^{3'} is C_{1-6} alkyl, C_{1-6} alkenyl, or C_{1-6} alkynyl. In some embodiments, R^{3'} is C_{1-6} alkyl. In certain embodiments, R^{3'} is C_{1-3} alkyl. In certain embodiments, R^{3'} is methyl, ethyl, propyl, or isopropyl. In some embodiments, R^{3'} is C_{1-6} alkenyl. In certain embodiments, R^{3'} is C_{1-3} alkenyl. In certain embodiments, R^{3'} is allyl. In some embodiments, R^{3'} is C_{1-6} alkynyl. In certain embodiments, R^{3'} is C_{1-3} alkynyl. In certain embodiments, R^{3'} is propargyl.

As defined generally above, each R⁴ is independently hydrogen, halogen, or an optionally substituted group selected from alkyl, alkenyl, alkynyl, carbocyclyl, heterocyclyl, aryl, heteroaryl, —OR^{A1}, —N(R^{A2})₂, —SR^{A1}, —C(=O)R^{A1}, —C(=O)OR^{A1}, —C(=O)N(R^{A2})₂, —OC(=O)R^{A1}, —NR^{A2}C(=O)R^{A2}, —NR^{A2}C(=O)OR^{A1}, —NR^{A2}C(=O)N(R^{A2})₂, —C(=NR^{A2})N(R^{A2})₂, —NR^{A2}C(=NR^{A2})R^{A1}—NR^{A2}C(=NR^{A2})N(R^{A2})₂, —SOR^{A1}, —SO₂R^{A1}, —NR^{A2}SO₂R^{A1}, —SO₂N(R^{A2})₂, —CN, —SCN, and —NO₂, wherein each R^{A1} is independently hydrogen, an amino protecting group, or an optionally substituted group selected from alkyl, alkenyl, alkynyl, carbocyclyl, heterocyclyl, aryl, and heteroaryl; and each R^{A2} is independently hydrogen or an optionally substituted group selected from alkyl, alkenyl, alkynyl, carbocyclyl, heterocyclyl, aryl, and heteroaryl, or two R^{A2} groups are taken together with their intervening atoms to form an optionally substituted heterocycle. In some embodiments, each instance of R⁴ is halogen. In some embodiments, each R⁴ is selected from bromo and chloro. In some embodiments, R⁴ is optionally substituted alkynyl. In some embodiments, R⁴ is ethynyl. In other embodiments, R⁴ is substituted ethynyl. In certain embodiments, R⁴ is trialkylsilyl-ethynyl. In certain embodiments, R⁴ is trimethylsilyl-ethynyl. In certain embodiments, R⁴ is

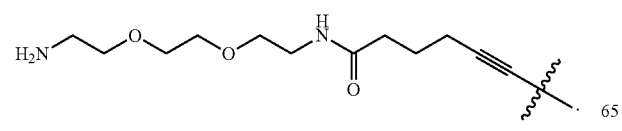

As defined generally above, n is 0, 1, 2, 3, or 4. In some embodiments, n is 0. In some embodiments, n is 1. In some embodiments, n is 2. In some embodiments, n is 3. In some embodiments, n is 4.

In some embodiments, n is 0, or alternatively, n is 1, 2, 3, or 4 and all instances of R⁴ are hydrogen, and the compound is febrifuginol. In other embodiments, n is 2, and one R⁴ is bromo and the other R⁴ is chloro. In certain embodiments, n is 2, and one R⁴ is bromo and the other R⁴ is chloro, and the compound is halofuginol. In certain embodiments, n is 2, and one R⁴ is halogen. In certain embodiments, n is 2, and one R⁴ is chloro. In certain embodiments, n is 2 and one R⁴ is optionally substituted alkynyl. In certain embodiments, n is 2, and one R⁴ is optionally substituted alkynyl and the other R⁴ is halogen. In certain embodiments, n is 2, and one R⁴ is ethynyl and the other R⁴ is chloro.

In certain embodiments, a provided compound is of one of the following formulae wherein R⁴ is not hydrogen and m, R¹, R², and R³ are as described herein:

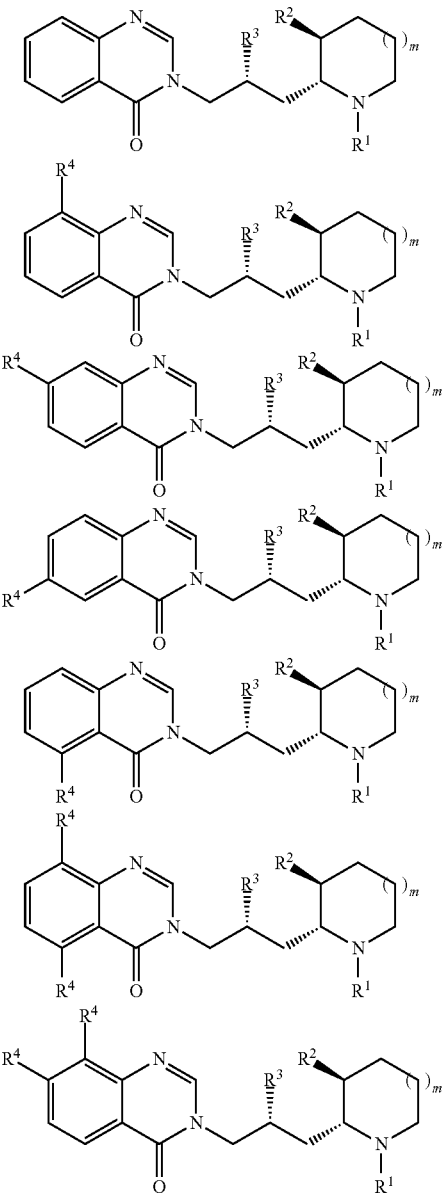

-continued
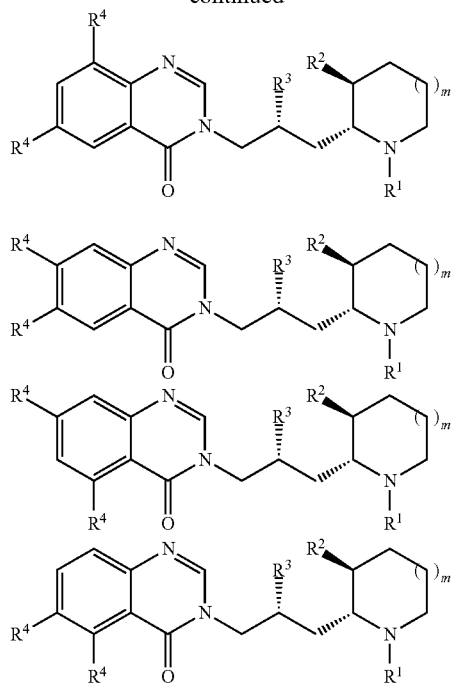
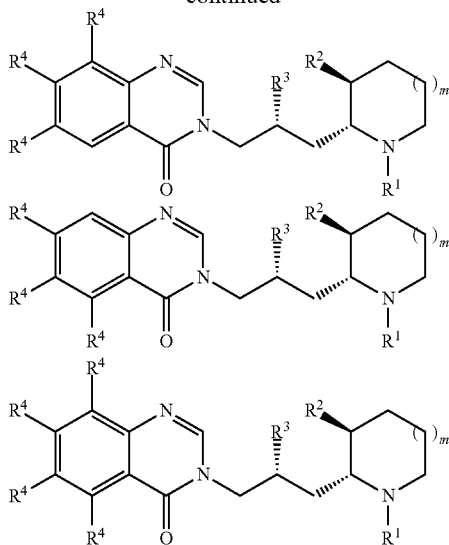
or a pharmaceutically acceptable salt thereof. In some embodiments, m is 1. In some embodiments, m is 0.
In certain embodiments, a provided compound is of formula:
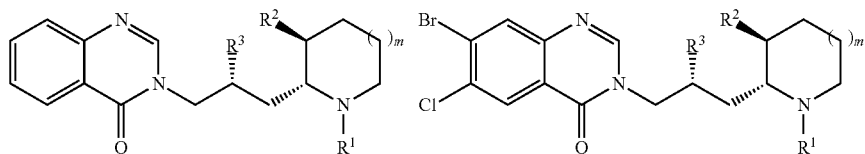
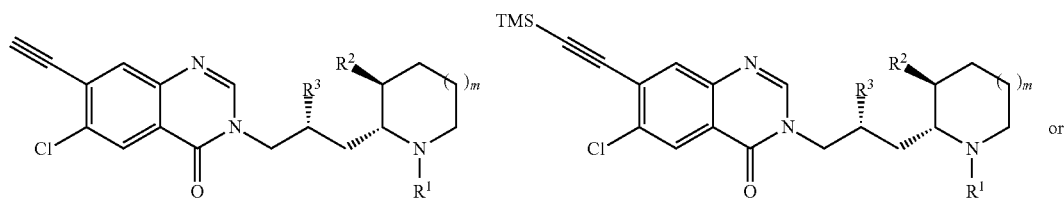
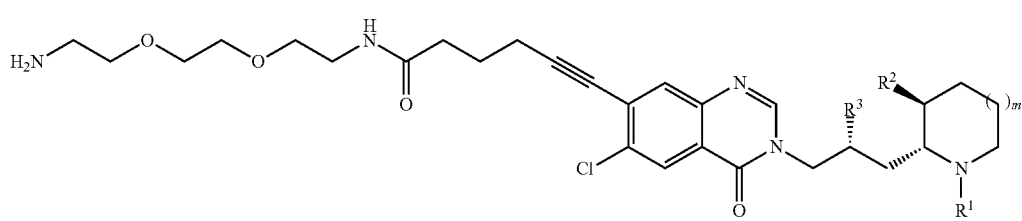

or a pharmaceutically acceptable salt thereof, wherein m, $R^1$, $R^2$, and $R^3$ are as described herein. In some embodiments, m is 1. In some embodiments, m is 0.

As defined generally above, m is 0 or 1. In some embodiments, m is 0. In some embodiments, m is 1.

In certain embodiments, a provided compound is of one of the following formulae wherein $R^4$ is not hydrogen and m, $R^1$, $R^2$, and $R^{3'}$ are as described herein:

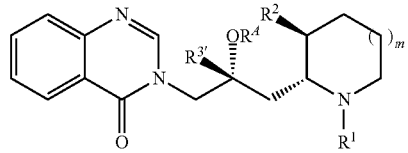

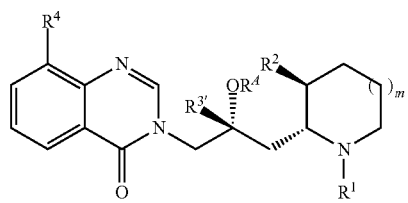

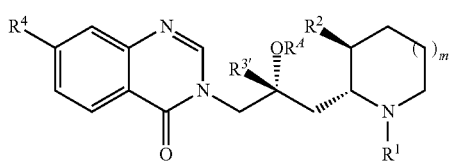

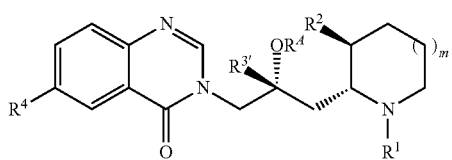

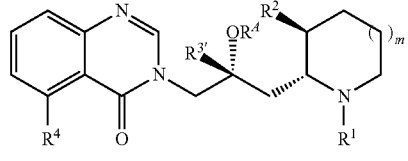

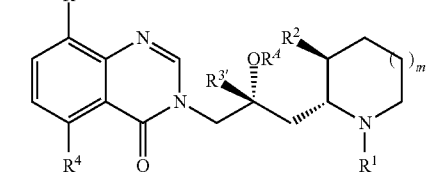

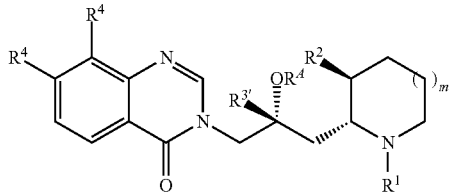

-continued

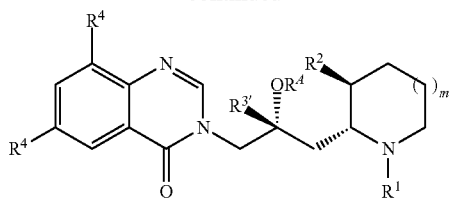

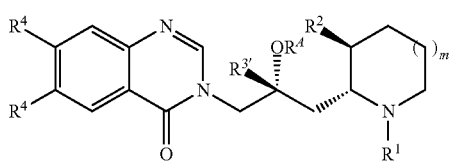

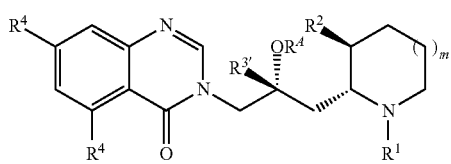

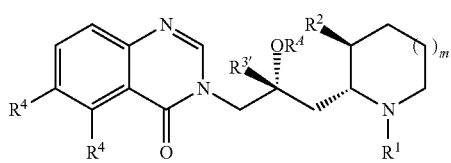

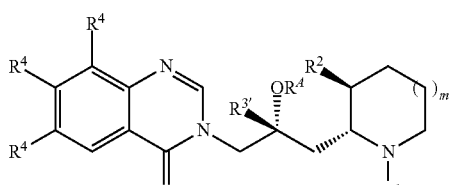

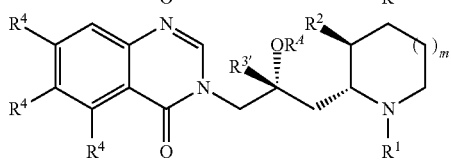

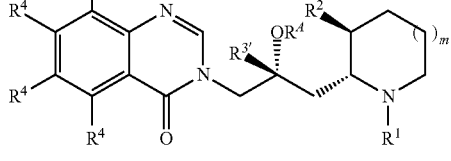

or a pharmaceutically acceptable salt thereof. In some embodiments, m is 1. In some embodiments, m is 0. In some embodiments, $R^A$ is hydrogen. In some embodiments, $R^{3'}$ is methyl. In some embodiments, $R^{3'}$ is allyl. In some embodiments, $R^A$ is hydrogen and $R^{3'}$ is methyl. In some embodiments, $R^A$ is hydrogen and $R^{3'}$ is allyl.

In certain embodiments, a provided compound is of formula:

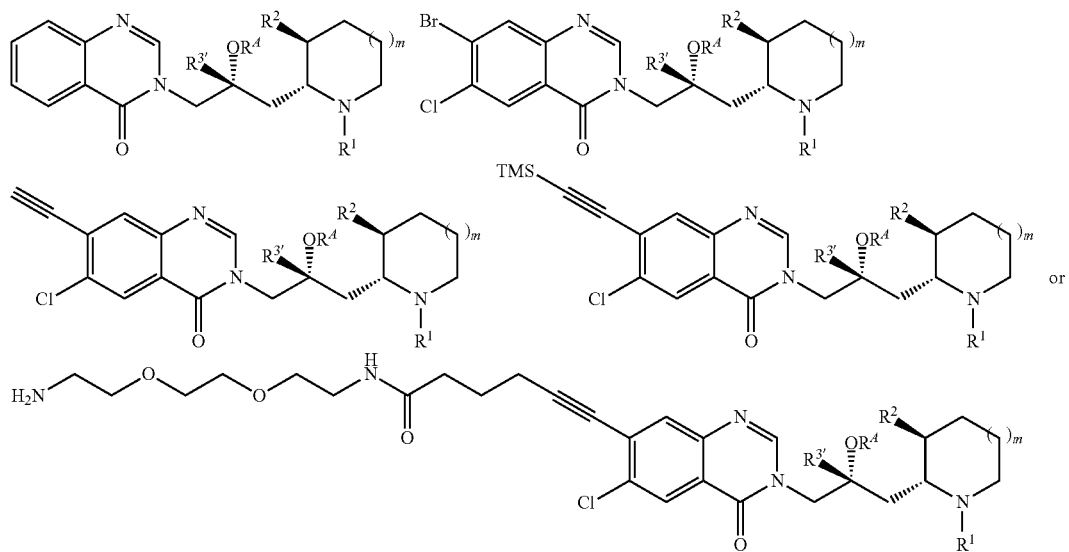

or a pharmaceutically acceptable salt thereof, wherein m, $R^1$, $R^2$, and $R^{3'}$ are as described herein. In some embodiments, m is 1. In some embodiments, m is 0. In some embodiments, $R^A$ is hydrogen. In some embodiments, $R^{3'}$ is methyl. In some embodiments, $R^{3'}$ is allyl. In some embodiments, $R^A$ is hydrogen and $R^{3'}$ is methyl. In some embodiments, $R^A$ is hydrogen and $R^{3'}$ is allyl.

In certain embodiments, a provided compound is one of the following:

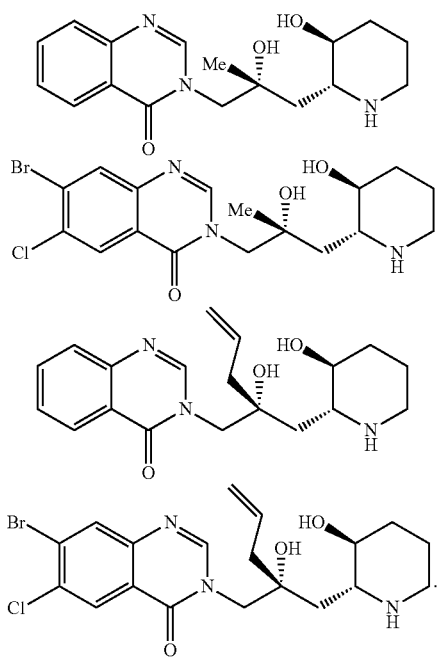

Figure 24:
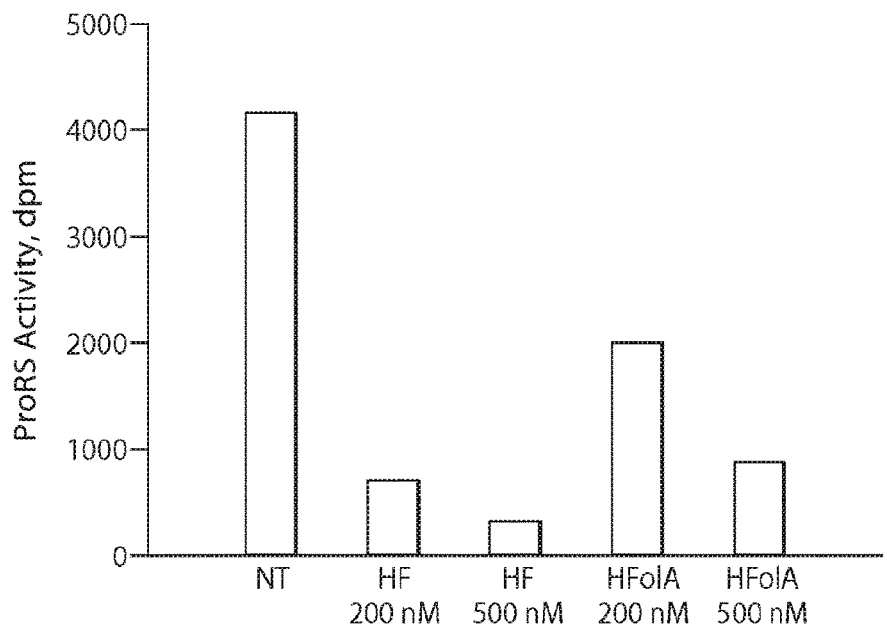
FIG. 24 shows inhibition of ProRS activity by HF and HFolA.
Figure 26:
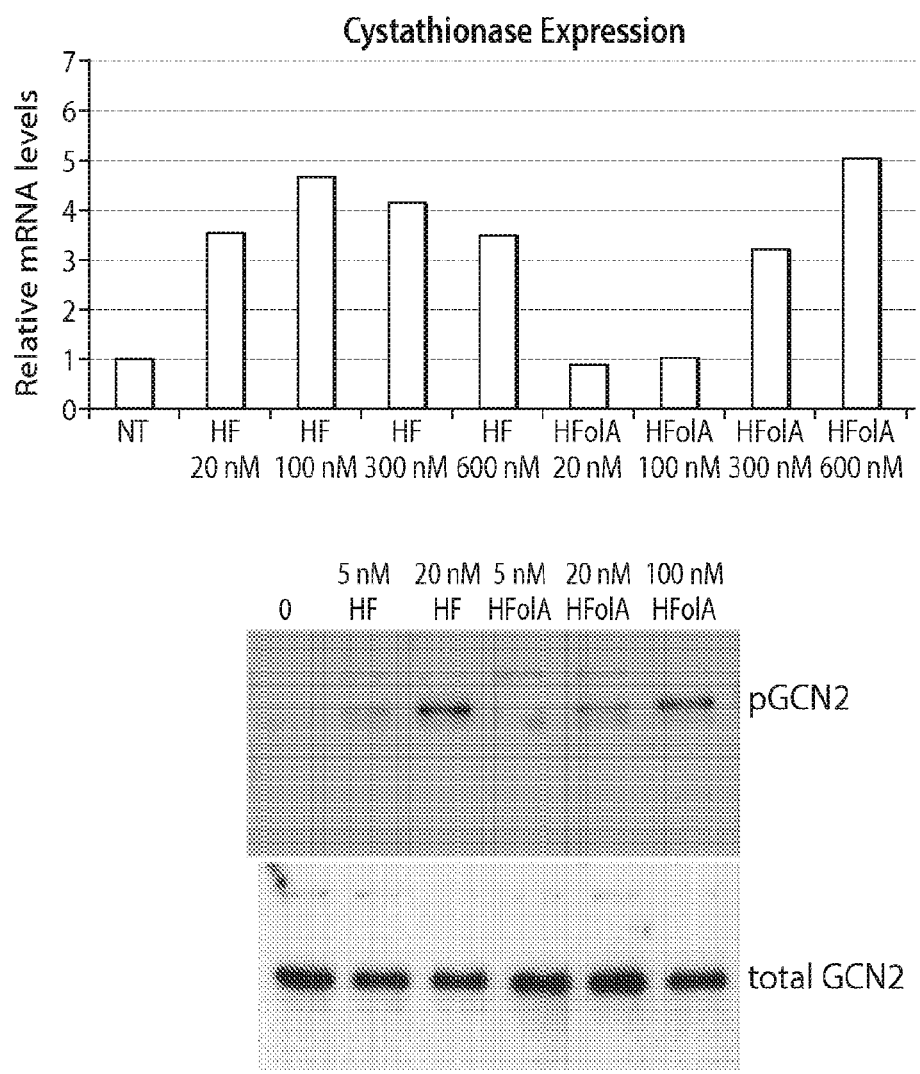
FIG. 26 shows activation of the amino acid response (AAR) by HF and HFolA in intact cells. Left Panel: AAR activation in primary human fibroblasts by HFolA and HF was measured as an induction of the AAR response gene cystathionase relative to a housekeeping gene control (GAPDH). Cells were treated with the indicated concentrations of HF or HFolA, and 4 hours later harvested for analysis of gene expression by Q-RT-PCR. Right panel: treated cells were analyzed by Western blot for induction of phosphorylation of the AAR kinase GCN2. HFolA activated the AAR by these criteria with approximately 5 fold reduced potency relative to HF.

In some embodiments, inventive compounds are as potent as halofuginone. In some embodiments, inventive compounds are more potent than halofuginone. In some embodiments, inventive compounds are less potent than halofuginone. In certain embodiments, inventive compounds have similar biological activity to halofuginone (e.g., within about 2-fold). In certain embodiments, inventive compounds are at least 10-fold, 5-fold, 2-fold more active than halofuginone against a tRNA synthetase (e.g., ProRS, EPRS). In certain embodiments, inventive compounds are less than 10-fold, 5-fold, 2-fold less active than halofuginone against a tRNA synthetase (e.g., ProRS, EPRS). For example, HFolA is about 2-fold less potent than halofuginone against prolyl tRNA synthetase (FIG. 24). In another example, HFolA about 5-10-fold less potent than halofuginone in activating the AAR (FIG. 26).

Figure 25:
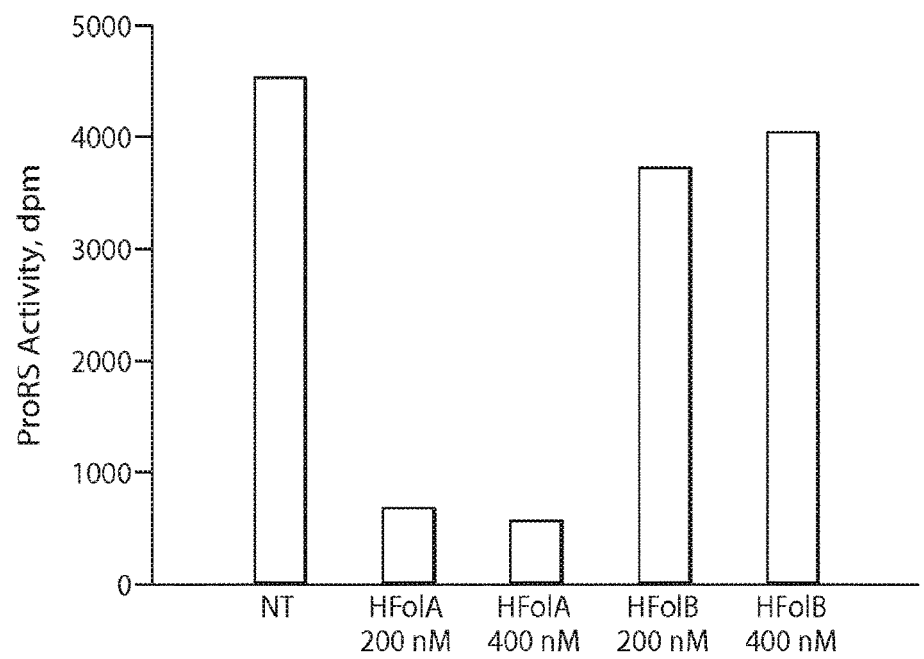
FIG. 25 shows measurement of inhibition of ProRS activity by two diastereomers of HFol. ProRS activity was measured as in FIG. 24. The active (HFolA) or inactive (HFolB) diastereomers of HFol were added to the reaction at the indicated concentrations.

In some embodiments, inventive compounds are more active than a diastereomer. In certain embodiments, inventive compounds are 2-fold, 5-fold, 10-fold, 20-fold, 50-fold, 100-fold, 1000-fold more potent than a diastereomer. In some embodiments, inventive compounds are more active than an epimer. In certain embodiments, inventive compounds are 2-fold, 5-fold, 10-fold, 20-fold, 50-fold, 100-fold, 1000-fold more potent than an epimer. In some embodiments, an inventive compound is active and its epimer is inactive. For example, HFolA inhibits prolyl tRNA synthetase activity, and its epimer HFolB does not display measurable activity in a prolyl tRNA synthetase assay (FIG. 25).

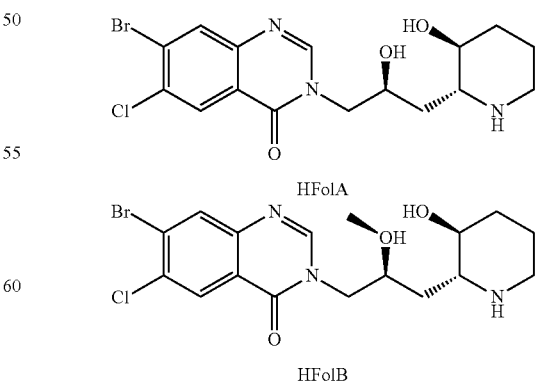

HFolA

HFolB

In some embodiments, compounds of the present invention are more stable than halofuginone. In some embodiments, compounds of the present invention are more stable than febrifugine. In some embodiments, provided compounds are more stable in solution than halofuginone. In other embodiments, provided compounds are more stable in solid form than halofuginone. Without wishing to be bound by theory, it is believed that the stability of provided compounds as compared with halofuginone is due to epimerization of halofuginone at the 2-position. The postulated mechanism is a retro-Michael reaction generating an α,β-unsaturated ketone and primary amine, which will re-attack from the opposite side (see, e.g., Zhu et al., *Eur. J. Med. Chem.* 45:3864-3869 (2010)); this mechanism should not be possible with compounds of the present invention.

Synthesis of Inventive Compounds

The compounds provided by the present invention may be prepared via any synthetic route known to one of skill in the art. For example, the compounds may be prepared from simple, commercially available starting materials, of the compounds may be prepared semi-synthetically using more complex starting materials such as halofuginone or febrifugine. The inventive compounds may be prepared using procedures in the literature. U.S. Pat. No. 4,762,838; U.S. Patent Application Publication 2008/0188498; Emmanuvel et al., "A concise enantioselective synthesis of (+)-febrifugine" *Tetrahedron: Asymmetry* 20(1):84-88, 2009; Ooi et al., "A Concise Enantioselective Synthesis of Antimalarial Febrifugine Alkaloids" *Organic Letters* 3(6):953-955, 2001; Ashoorzadeh et al., "Synthetic evaluation of an enantiopure tetrahydropyridine N-oxide. Synthesis of (+)-febrifugine" *Tetrahedron* 65(24):4671-4680, 2009; Sukemoto et al., "Concise asymmetric synthesis of (+)-febrifugine utilizing trans-selective intramolecular conjugate addition" *Synthesis* (19):3081-3087, 2008; Kikuchi et al., "Exploration of a New Type of Antimalarial Compounds Based on Febrifugine" *Journal of Medicinal Chemistry* 49(15):4698-4706, 2006; Takaya et al., "New Type of Febrifugine Analogues, Bearing a Quinolizidine Moiety, Show Potent Antimalarial Activity against Plasmodium Malaria Parasite" *Journal of Medicinal Chemistry* 42(16):3163-3166, 1999; U.S. Patent Application Publication 2011/0263532. The inventive compounds may also be prepared from commercially available starting materials using the following synthetic schemes. The following schemes are only meant to exemplify the routes available to a synthetic organic chemist for preparing the inventive compounds. As would be readily apparent to one of skill in this art, these exemplary schemes may be modified to use different starting materials, reagents, and/or reaction conditions.

In some embodiments, the present invention provides a diastereoselective synthesis of certain inventive compounds. Surprisingly, it has been found that protection of the piperidine nitrogen of halofuginone with a bulky group such as tert-butyloxycarbonyl blocks the undesired face from hydride attack to give the desired diastereomer of halofuginol (see Scheme 1). In certain embodiments, sodium hydride is employed in the reduction. Such methods can be used to provide other compounds of the present invention as well (Scheme 2). Alternatively, products obtained from Scheme 1 can be further derivatized to give other compounds of Formula (I).

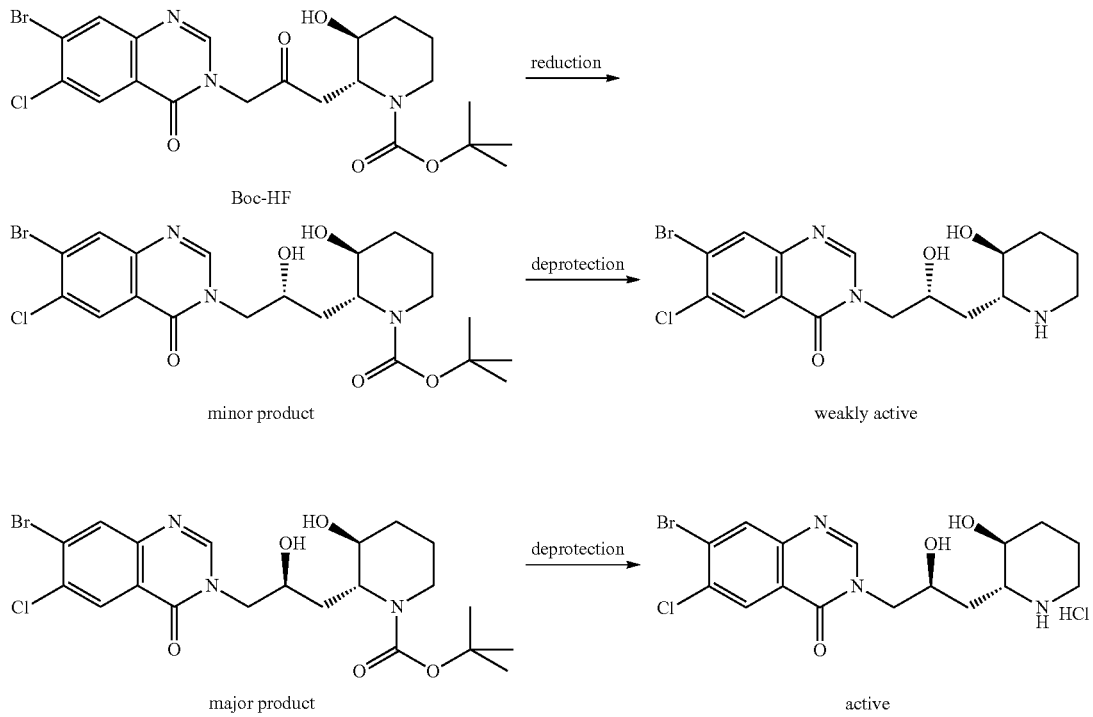

Scheme 1

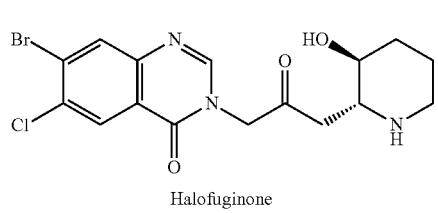

Halofuginone

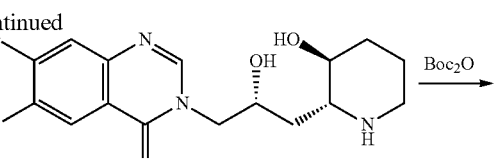

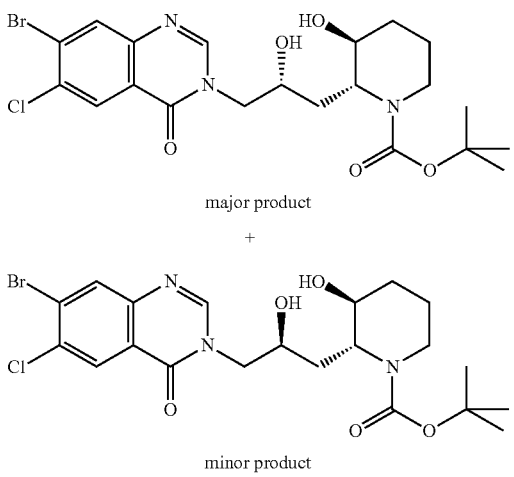

major product

+ minor product

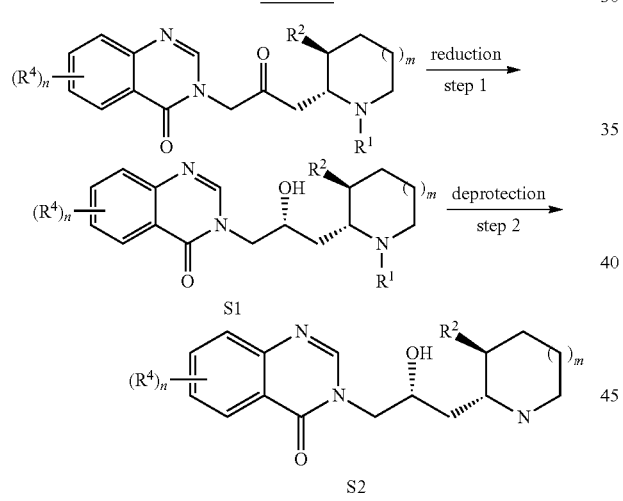

Scheme 2

In some embodiments, the reduction to give S1 takes place in the presence of a hydride reagent, such as sodium borohydride. In certain embodiments, the reaction takes place in a polar protic solvent (e.g., methanol, ethanol). In certain embodiments, the reaction takes place in a polar aprotic solvent (e.g., tetrahydrofuran). Product S2 is deprotected using appropriate conditions given the identity of $R^1$ (see *Greene's Protective Groups in Organic Synthesis*, P. G. M. Wuts and T. W. Greene, 4$^{th}$ edition, Wiley-Interscience, 2006). S2 can then be further derivatized if desired. In certain embodiments, the hydroxyl group is acylated or alkylated to give an ester or ether, respectively.

Compounds of the present invention containing an $R^2$ or $R^3$ amino group can be synthesized, for example, from the hydroxyl (e.g., Mitsunobu or other displacement reaction) or from the ketone (e.g., reductive amination). In some embodiments, an amino group of the desired stereochemistry can be installed as shown in Scheme 3 for example (where P is a protecting group). In other embodiments, an amino group can be installed as shown in Scheme 4 for example. In some embodiments, a reductive amination may proceed stereoselectively as shown in Scheme 5.

Scheme 3

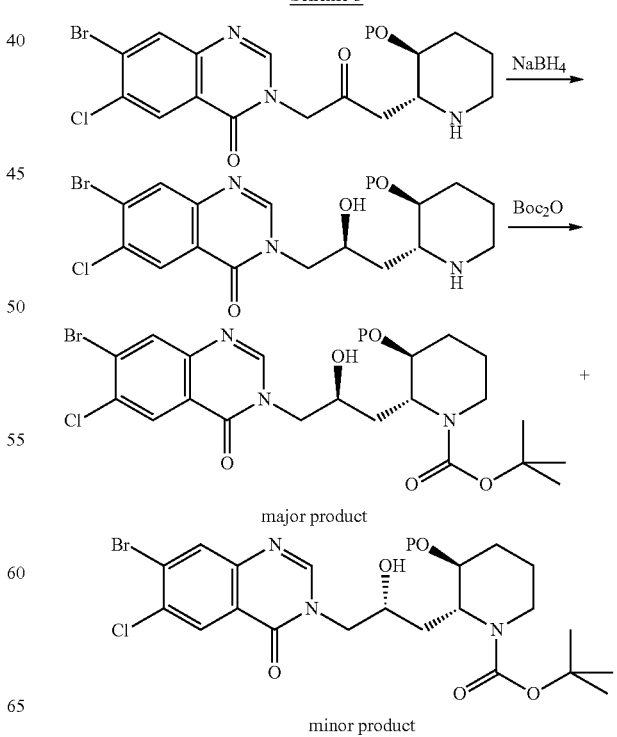

major product minor product

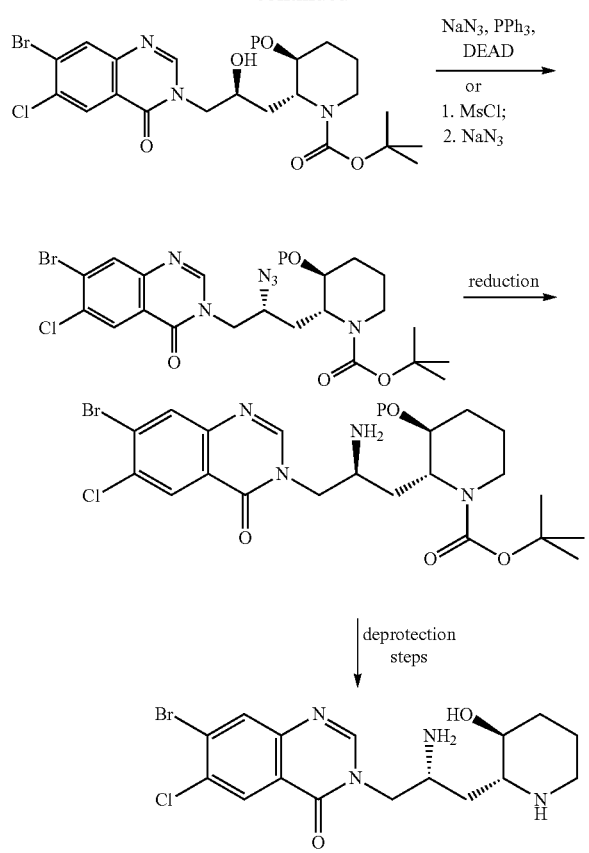
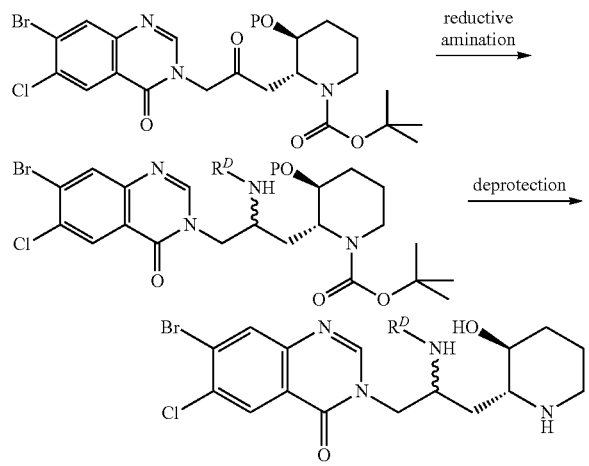

Scheme 4

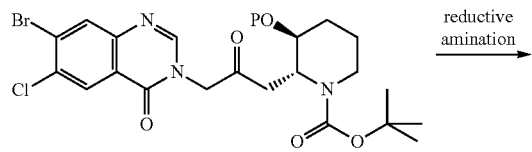

Scheme 5

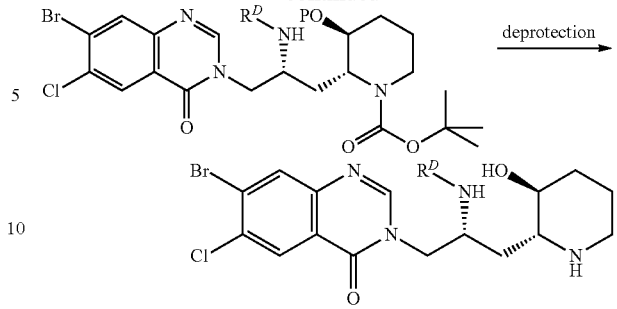

Inhibition of Glutamyl-Prolyl tRNA Synthetase (EPRS)

Certain compounds described herein act as inhibitors of metazoan glutamyl-prolyl tRNA synthetase (EPRS) or non-metazoan prolyl tRNA synthetase. In certain embodiments, the EPRS is a eukaryotic EPRS. In certain embodiments, the EPRS is a human EPRS. In certain embodiments, the prolyl tRNA synthetase is a protozoan prolyl tRNA synthetase. A structural feature of these inhibitors is a piperidine or pyrrolidine ring, or an analog thereof. Without wishing to be bound by a particular theory, it is believed that the piperidine ring or pyrrolidine ring of compounds of the present invention acts by binding in the active site of the tRNA synthetase like the pyrrolidine ring of proline, thus preventing the charging of the amino acid proline to the tRNA synthetase.

Inhibition of EPRS or other tRNA synthetases leads to the accumulation of uncharged prolyl tRNAs, which in turn activates the amino acid starvation response (AAR). Activation of the AAR in T-cells suppresses the differentiation of a subset of effector T-cells (Th17 cells) that promote autoimmunity. AAR also suppresses pro-fibrotic gene expression and viral gene expression, replication, and maturation. AAR may contribute to the protection of organs from stress (e.g., ER stress in the pancreas during the development of diabetes).

Inhibition of EPRS suppresses the synthesis and accumulation of proteins such as polyglutamine-containing proteins that cause neurodegenerative diseases such as Huntington's disease. This class of EPRS inhibitors also promotes autophagy, a process that clears protein aggregates in diseases such as Huntington's disease, Alzheimer's disease, Parkinson's disease, and amyotrophic lateral sclerosis (ALS). Halofuginol and similarly active compounds are therefore useful as promoters of autophagy.

The specific inhibition of EPRS (as opposed to other tRNA synthetases) also inhibits the synthesis of proline-rich proteins such as collagen, which may be useful for the inhibition of scarring and fibrosis due to excess collagen deposition. Inhibition of collagen synthesis may be useful for cosmetic and therapeutic applications. The role of collagen in fibrosis makes the inventive compounds useful in various cosmetic and therapeutic applications associated with the accumulation of collagen. Inventive compounds are also useful in treating stretch marks and cellulite.

The synthesis of collagen and the degradation and remodelling of the ECM are involved in a number of physiological and pathological conditions, including angiogenesis, systemic sclerosis, graft-versus-host disease (GVHD), pulmonary and hepatic fibrosis, and autoimmune diseases. These diseases are many times associated with the excessive production of connective tissue components, particularly collagen, which results in the destruction of normal tissue architecture and function. Therefore, the inventive compounds may be useful in treating or preventing diseases associated with collagen accumulation or the degradation and remodelling of the ECM.

In Vitro Methods

Provided compounds may be screened to identify compounds with a desired biological activity, e.g., the ability to modulate the development and/or expansion of Th17 cells by inhibiting EPRS, e.g., IL-17 secreting cells. An assay for screening selective inhibitors of IL-17 expressing cell development and/or expansion, such as IL-17 expressing effector T-cell development and/or expansion, e.g., Th17 development and/or expansion includes contacting a naïve T-cell population with a test compound under conditions sufficient to allow T-cell development and/or expansion, culturing the cell population, and detecting the level of IL-17 expression and/or the number of Th17 cells in the cell population, wherein no change or a decrease in the level of IL-17 expression in the cell population indicates that the test compound is a selective Th17 inhibitor and/or wherein no change or a decrease in the number of Th17 cells in the cell population indicates that the test compound is a selective Th17 inhibitor. Determining the level of IL-17 expression and/or the number of Th17 cells in the cell population can be accomplished for example by using a detection agent that binds to IL-17 or other marker for Th17 cells, for example, the Th17-specific transcription factor RORgammat (RORγt). In certain embodiments, the detection agent is an antibody. The detection agent can be coupled to a radioisotope or an enzymatic label such that binding of the detection agent to IL-17 or other Th17 marker can be determined by detecting the labeled compound. For example, the detection agent can be labeled with $^{125}I$, $^{35}S$, $^{14}C$, or $^3H$, either directly or indirectly, and the radioisotope detected by direct counting of radioemission or by scintillation counting. Alternatively, detection agents can be enzymatically labeled with, for example, horseradish peroxidase, alkaline phosphatase, or luciferase, and the enzymatic label detected by determination of conversion of an appropriate substrate to product.

Methods of Modulating Th17 Cell Differentiation and/or Proliferation and Other Cellular Functions Using Inventive Compounds and Compositions Thereof Halofuginone and analogs thereof have been found to specifically alter the development of T-cells away from the Th17 lineage, which is associated with cell-mediated damage, persistent inflammation, and autoimmunity. In certain embodiments, compounds of the present invention alter development of T-cells away from the Th17 lineage.

Th17 cells secrete several cytokines that may have a role in promoting inflammation and fibrosis, including IL-17, IL-6, IL-21, and GM-CSF. Of these cytokines, IL-17 is a specific product of Th17 cells, and not other T-cells. Whether Th17 cells are the only source of IL-17 during inflammatory response is not clear, but elevated IL-17 levels are in general thought to reflect the expansion of the Th17 cell population.

Diseases that have been associated with expansion of a Th17 cell population or increased IL-17 production include, but are not limited to, rheumatoid arthritis, multiple sclerosis, Crohn's disease, inflammatory bowel disease, dry eye syndrome, Lyme disease, airway inflammation, transplantation rejection, graft versus host disease, lupus, psoriasis, scleroderma, periodontitis, systemic sclerosis, coronary artery disease, myocarditis, atherosclerosis, diabetes, and inflammation associated with microbial infection (e.g., viral, protazoal, fungal, or bacterial infection).

Provided compounds can be useful for treatment of any of these diseases by suppressing the chronic inflammatory activity of IL-17 expressing cells, such as IL-17 expressing effector T-cells, e.g., Th17 cells. In some instances, this may address the root cause of the disease (e.g., self-sustaining inflammation in rheumatoid arthritis); in other cases (e.g., diabetes, periodontitis) it may not address the root cause but may ameliorate the symptoms associated with the disease.

IL-17 expressing effector T-cells, e.g., Th17 cells, and their associated cytokine IL-17 provide a broad framework for predicting or diagnosing diseases potentially treatable by halofuginol and analogs thereof. Specifically, pre-clinical fibrosis and/or transplant/graft rejection could be identified and treated with a provided compound, or with a provided compound in combination with other Th17 antagonists. Additionally, diseases that are not currently associated with Th17 cell damage and persistence of inflammation may be identified through the measurement of Th17 cell expansion, or of increased IL-17 levels (e.g., in serum or synovial fluid). Alternatively, or in addition, the use of gene profiling to characterize sets of genes activated subsequent to Th17 differentiation may allow detection of Th17-affected tissues, prior to histological/pathologic changes in tissues.

Provided compounds can be used in combination with other agents that act to suppress Th17 development to achieve synergistic therapeutic effects. Current examples of potential synergistic agents would include anti-IL-21 antibodies or antigen binding fragments thereof, retinoic acid, or anti-IL-6 antibodies or antigen binding fragments thereof, all of which can reduce Th17 differentiation.

Provided compounds can be used in combination with other agents that act to suppress inflammation and/or immunological reactions, such as steroids (e.g., cortisol (hydrocortisone), dexamethasone, methylprednisolone, prednisolone), non-steroidal anti-inflammatory drugs (NSAIDs; e.g., ibuprofen, acetominophin, aspirin, celecoxib, valdecoxib, etoricoxib, lumiracoxib, parecoxib, rofecoxib, nimesulide, naproxen), or immunosuppressants (e.g., cyclosporine, rapamycin, FK506). In certain embodiments, provided compounds are used in combination with agents that are immunomodulatory (e.g., modulators of the mTOR pathway; thalidomide and derivatives thereof such as lenalidomide and actimid; biguanides such as metformin, phenformin, buformin, and proguanil; and HDAC inhibitors such as trichostatin A, romidepsin, SAHA, PXD101, LAQ824, LBH589, MS275, CI994, MGCD0103, and valproic acid. In some embodiments, an agent that inhibits a tRNA synthetase is used in combination with an inhibitor of a proinflammatory cytokine. Proinflammatory cytokines that can be targeted (in addition to IL-6 and IL-21, discussed above) include TNFα, IFNγ, GM-CSF, MIP-2, IL-12, IL-1α, IL-1β, and IL-23, Examples of such inhibitors include antibodies that bind to the cytokine or that bind to a receptor of the cytokine and block its activity, agents that reduce expression of the cytokine (e.g., small interfering RNA (siRNA) or antisense agents), soluble cytokine receptors, and small molecule inhibitors (see, e.g., WO 2007/058990).

In some embodiments, provided compounds are used in combination with an inhibitor of TNFα. In some embodiments, an inhibitor of TNFα comprises an anti-TNFα antibody or antigen binding fragment thereof. In some embodiments, the anti-TNFα antibody is adalimumab (Humira™). In some embodiments, the anti-TNFα antibody is infliximab (Remicade™). In some embodiments, the anti-TNFα antibody is CDP571. In some embodiments, the inhibitor of TNFα is a TNFα receptor or a fragment thereof. For example, in some embodiments, the TNFα inhibitor is etanercept (Enbrel™), which is a recombinant fusion protein having two soluble TNF receptors joined by the Fc fragment of a human IgG1 molecule. In some embodiments, the inhibitor of TNFα is an agent that inhibits the expression of TNFα, e.g., such as nucleic acid molecules that mediate RNA interference (RNAi) (e.g., a TNFα selective siRNA or shRNA) or antisense oligonucleotides. For example, a TNFα inhibitor can include, e.g., a short interfering nucleic acid (siNA), a short interfering RNA (siRNA), a double-stranded RNA (dsRNA), or a short hairpin RNA (shRNA) (see, e.g., U.S. Patent Application No. 20050227935, incorporated herein by reference).

Provided compounds may be evaluated in animal models of a disease. To determine whether a particular inventive compound suppresses graft rejection, allogeneic or xenogeneic grafting (e.g., skin grafting, organ transplantation, or cell implantation) can be performed on an animal such as a rat, mouse, rabbit, guinea pig, dog, or non-human primate. Strains of mice such as C57B1-10, B10.BR, and B10.AKM (Jackson Laboratory, Bar Harbor, Me.), which have the same genetic background but are mismatched for the H-2 locus, are well suited for assessing various organ grafts.

In one particular example, heart transplantation is performed, e.g., by performing cardiac grafts by anastomosis of the donor heart to the great vessels in the abdomen of the host as described by Ono et al., *J. Thorac. Cardiovasc. Surg.* 57:225, 1969. See also Corry et al., *Transplantation* 16:343, 1973. Function of the transplanted heart can be assessed by palpation of ventricular contractions through the abdominal wall. Rejection is defined as the cessation of myocardial contractions. An inventive compound would be considered effective in reducing organ rejection if animals treated with the inhibitor experience a longer period of myocardial contractions of the donor heart than do untreated hosts.

In another example, effectiveness of an inventive compound in reducing skin graft rejection is assessed in an animal model. To perform skin grafts on a rodent, a donor animal is anesthetized and a full thickness of skin is removed from a part of the tail. The recipient animal is also anesthetized, and a graft bed is prepared by removing a patch of skin (e.g., 0.5×0.5 cm) from the shaved flank. Donor skin is shaped to fit the graft bed, positioned, covered with gauze, and bandaged. Grafts are inspected daily beginning on the sixth post-operative day and are considered rejected when more than half of the transplanted epithelium appears to be non-viable. An inventive compound that causes a host to experience a longer period of engraftment than seen in an untreated host would be considered effective in this type of experiment.

In another example, an inventive compound is evaluated in a pancreatic islet cell allograft model. DBA/2J islet cell allografts can be transplanted into rodents, such as 6-8 week-old B6 AF1 mice rendered diabetic by a single intraperitoneal injection of streptozotocin (225 mg/kg; Sigma Chemical Co., St. Louis, Mo.). As a control, syngeneic islet cell grafts can be transplanted into diabetic mice. Islet cell transplantation can be performed by following published protocols (for example, see Emamaullee et al., *Diabetes* 56(5):1289-98, 2007). Allograft function can be followed by serial blood glucose measurements (Accu-Check III™; Boehringer, Mannheim, Germany). A rise in blood glucose exceeding normal levels (on each of at least 2 successive days) following a period of primary graft function is indicative of graft rejection. The NOD (non-obese diabetic) mouse model is another model that can be used to evaluate ability of an inventive compound to treat or prevent type I diabetes.

In another example, an inventive compound is evaluated in a model of dry eye disease (DED). In one such model, DED is induced in mice in a controlled environment chamber by administering scopolamine hydrobromide into the skin four times daily. Chamber conditions include a relative humidity <30%, airflow of 15 L/min, and constant temperature (21-23° C.). Induction of dry eye can be confirmed by measuring changes in corneal integrity with corneal fluorescein staining (see, e.g., Chauhan et al., *J. Immunol.* 182:1247-1252, 2009; Barabino et al., *Invest. Ophthamol. Visual Sci.* 46:2766-2771, 2005; and Rashid et al., *Arch. Ophthamol.* 126: 219-225, 2008).

Numerous autoimmune diseases have been modeled in animals, including rheumatic diseases, such as rheumatoid arthritis and systemic lupus erythematosus (SLE), type I diabetes, dry eye syndrome, and autoimmune diseases of the thyroid, gut, and central nervous system. For example, animal models of SLE include MRL mice, BXSB mice, and NZB mice and their F1 hybrids. The general health of the animal as well as the histological appearance of renal tissue can be used to determine whether the administration of an inventive compound can effectively suppress the immune response in an animal model of one of these diseases.

Animal models of intestinal inflammation are described, for example, by Elliott et al. (Elliott et al., 1998, Inflammatory Bowel Disease and Celiac Disease. In: The Autoimmune Diseases, Third ed., N. R. Rose and I. R. MacKay, eds. Academic Press, San Diego, Calif.). Some mice with genetically engineered gene deletions develop chronic bowel inflammation similar to IBD. See, e.g., Elson et al., *Gastroenterology* 109:1344, 1995; Ludviksson et al., *J. Immunol.* 158:104, 1997; and Mombaerts et al., *Cell* 75:274, 1993). One of the MRL strains of mice that develops SLE, MRL-lpr/lpr, also develops a form of arthritis that resembles rheumatoid arthritis in humans (Theofilopoulos et al., *Adv. Immunol.* 37:269, 1985).

Models of autoimmune disease in the central nervous system (CNS), such as experimental allergic encephalomyelitis (EAE), can also be experimentally induced, e.g., by injection of brain or spinal cord tissue with adjuvant into the animal (see, e.g., Steinman and Zamvil, Ann Neurol. 60:12-21, 2006). In one EAE model, C57B/6 mice are injected with an immunodominant peptide of myelin basic protein in Complete Freund's Adjuvant. EAE disease correlates such as limp tail, weak/altered gait, hind limb paralysis, forelimb paralysis, and morbidity are monitored in animals treated with an inventive compound as compared to controls.

In addition to T cell differentiation processes, provided compounds can specifically alter processes such as fibrosis and angiogenesis. Fibrosis can be assayed in vitro by observing the effect of an inventive compound on fibroblast behavior. In one exemplary assay for use in evaluating compounds described herein, primary dermal fibroblasts are cultured in a matrix of Type I collagen, which mimics the interstitial matrix of the dermis and hypodermis, such that fibroblasts attach to the substratum and spread. Inhibition of fibroblast attachment and spreading in the presence of a compound described herein indicates that the compound has anti-fibrotic properties. Biological effects of provided on non-immune cell functions can also be evaluated in vivo. In some embodiments, a compound of the present invention reduces extracellular matrix deposition (e.g., in an animal model of wound healing; see, e.g., Pines et al., *Biol. Bone Marrow Transplant* 9:417-425, 2003). In some embodiments, a compound of the present invention reduces extracellular matrix deposition at a concentration lower than the concentration at which it inhibits another cellular function, such as cell proliferation or protein synthesis.

The invention further provides methods of treating a disease using a compound of the present invention. The inventive method involves the administration of a therapeutically effective amount of an inventive compound to a subject (including, but not limited to a human or other animal).

Compounds and compositions described herein are useful for the inhibition of glutamyl-prolyl tRNA synthetase (EPRS). Inhibition of EPRS leads to the accumulation of uncharged tRNAs, which in turn activate the amino acid starvation response (AAR). Activation of this response suppresses 1) pro-fibrotic gene expression; 2) the differentiation of naïve T-cells into Th17 cells that promote autoimmunity; 3) viral gene expression, replication, and maturation; and/or 4) stress to organs (e.g., during transplantation).

In some embodiments, a compound of the present invention that inhibits EPRS has anti-fibrotic properties in vivo. For example, halofuginone, which is an EPRS inhibitor, potently reduces dermal extracellular matrix (ECM) deposition (Pines et al., *Biol. Blood Marrow Transplant* 9: 417-425, 2003). Halofuginone inhibits the transcription of a number of components and modulators of ECM function, including Type I collagen, fibronectin, the matrix metallopeptidases MMP-2 and MMP-9, and the metalloprotease inhibitor TIMP-2 (Li et al., *World J. Gastroenterol.* 11: 3046-3050, 2005; Pines et al., *Biol. Blood Marrow Transplant* 9: 417-425, 2003). The major cell types responsible for altered ECM deposition, tissue thickening, and contracting during fibrosis are fibroblasts and myofibroblasts. Myofibroblasts mature/differentiate from their precursor fibroblasts in response to cytokine release, often following tissue damage and mechanical stress, and can be distinguished from fibroblasts in a wide range of organs and pathological conditions (Border et al., *New Eng. J. Med.* 331: 1286-1292, 1994; Branton et al., *Microbes Infect.* 1: 1349-1365, 1999; Flanders, *Int. J. Exp. Pathol.* 85: 47-64, 2004). Halofuginone has been studied extensively as a potential anti-fibrotic therapeutic and has progressed to phase 2 clinical trials for applications stemming from these properties.

In animal models of wound healing and fibrotic disease, halofuginone reduces excess dermal ECM deposition when introduced intraperitoneally, added to food, or applied locally (Pines et al., *Biol. Blood Marrow Transplant* 9: 417-425, 2003). Halofuginone is currently in phase 2 clinical trials as a treatment for scleroderma (Pines et al., *Biol. Blood Marrow Transplant* 9: 417-425, 2003), bladder cancer (Elkin et al., *Cancer Res.* 59: 4111-4118, 1999), and angiogenesis during Kaposi's sarcoma, as well as in earlier stages of clinical investigation for a wide range of other fibrosis-associated disorders (Nagler et al., *Am. J. Respir. Crit. Care Med.* 154: 1082-1086, 1996; Nagler et al., *Arterioscler. Thromb. Vasc. Biol.* 17: 194-202, 1997; Nagler et al., *Eur. J. Cancer* 40: 1397-1403, 2004; Ozcelik et al., *Am. J. Surg.* 187: 257-260, 2004). The results presented herein indicate that the inhibition of fibrosis may be due at least in part to the inhibition of glutamyl-prolyl tRNA synthetase (EPRS).

Figure 27:
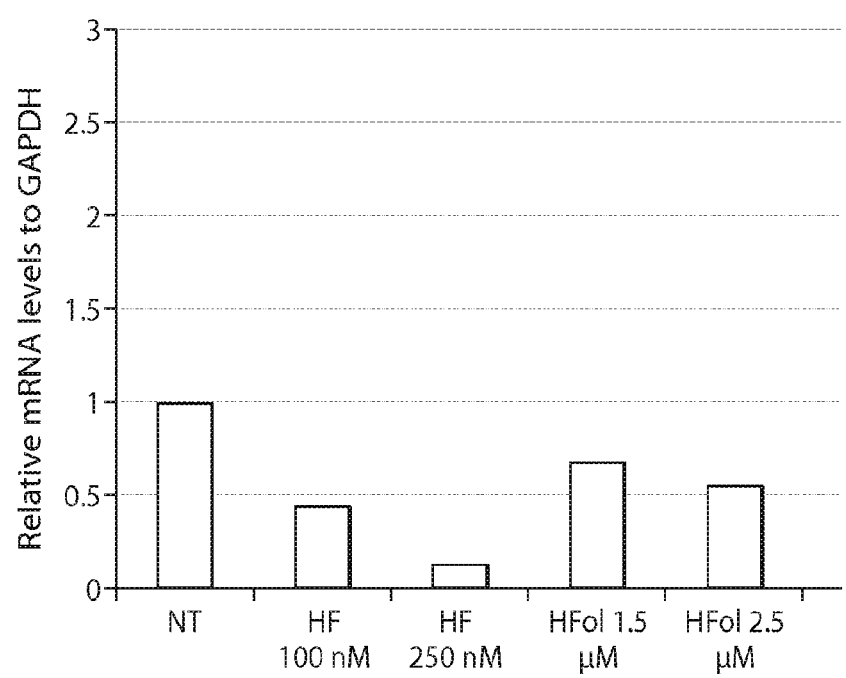
FIG. 27 shows that HFol and HF inhibit type 1 collagen expression in fibroblasts in culture.
Figure 28:
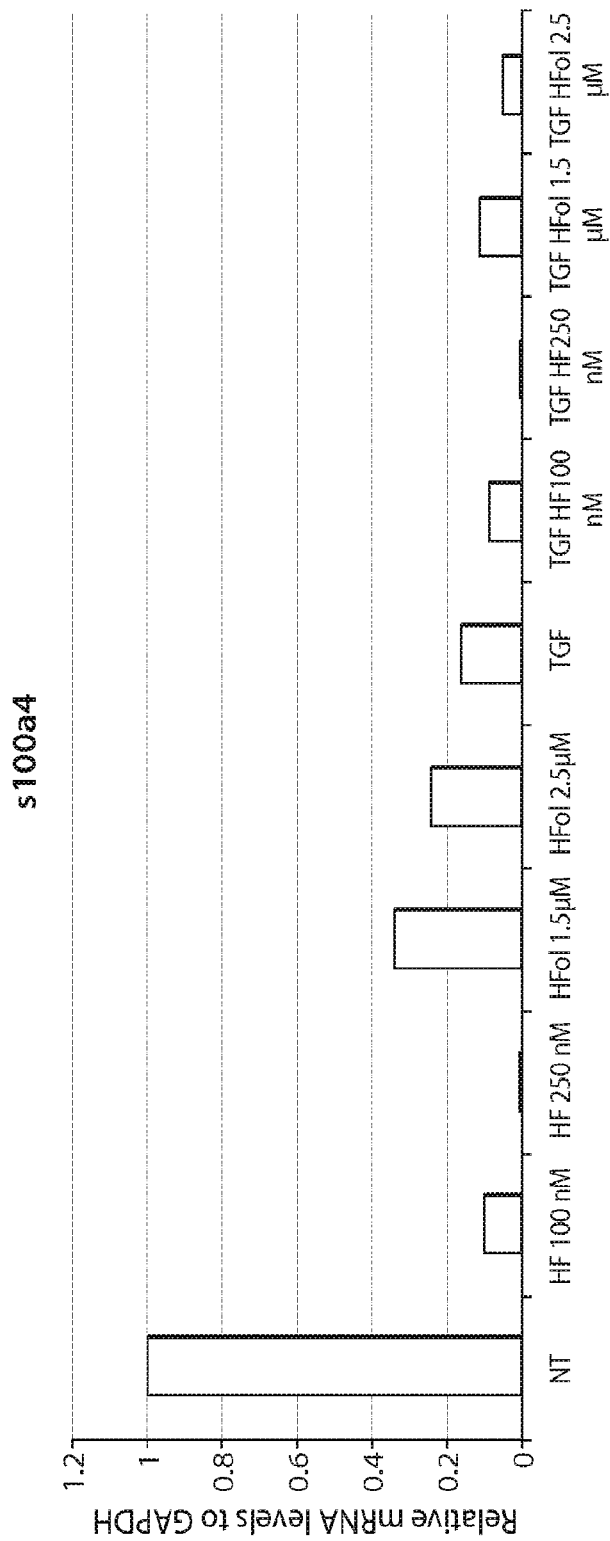
FIG. 28 shows that HFol and HF inhibit expression of the activated fibroblast marker S100A4.

Halofuginol and halofuginone inhibit Type 1 collagen expression in fibroblasts in culture, and inhibit expression of the activated fibroblast marker S100A4 (FIGS. 27 and 28).

In some embodiments, an inventive compound inhibits pro-fibrotic activities of fibroblasts. Thus, in certain embodiments, the present invention provides a method for treating a fibroblast-associated disorder comprising the step of administering to a patient in need thereof a compound of the present invention or pharmaceutically acceptable composition thereof.

As used herein, the term "fibroblast-associated" disorders means any disease or other deleterious condition in which fibroblasts are known to play a role. Accordingly, another embodiment of the present invention relates to treating or lessening the severity of one or more diseases in which fibroblasts are known to play a role including, but not limited to, fibrosis, cellulite, and stretch marks. In certain embodiments, a compound of the present invention decreases the appearance of cellulite in a subject by inhibiting maturation of myofibroblasts. In some embodiments, a compound of the present invention decreases the appearance of cellulite in a subject by modulating extracellular matrix remodeling.

While halofuginone at high concentrations (between 20-40 nM) does generally inhibit $CD4^+$ T cell, $CD8^+$ T cell, and $B220^+$ B cell activation, halofuginone also specifically inhibits the development of Th17 cells, i.e., the T helper subset that exclusively expresses high levels of the pro-inflammatory cytokine interleukin IL-17, at low concentrations (PCT/US08/09774, filed Aug. 15, 2008, which claims priority to U.S. Provisional Application U.S. Ser. No. 60/964,936, filed Aug. 15, 2007, the entirety of each of which is incorporated herein by reference). Th17 cells, as a function of their IL-17 secretion, play causal roles in the pathogenesis of two important autoimmune diseases in the mouse, experimental autoimmune encephalomyelitis (EAE) and type II collagen-induced arthritis (CIA). EAE and CIA are murine models of the human autoimmune pathologies, multiple sclerosis (MS) and rheumatoid arthritis (RA). Halofuginone has been shown to be active in these models. Halofuginone-mediated specific inhibition of IL-17 expressing cell development, such as IL-17 expressing effector T cell development, e.g., Th17 cell development, takes place at remarkably low concentrations, with 50% inhibition being achieved around 3 nM. Therefore, halofuginone treatment specifically inhibits the development of Th17-mediated and/or IL-17 related diseases, including autoimmune diseases, persistent inflammatory diseases, and infectious diseases, while not leading to profound T-cell dysfunction, either in the context of delayed-type hypersensitivity or infection. Inventive compounds can also be used to inhibit the development of Th17-mediated and/or IL-17 related diseases.

Halofuginone and analogs thereof interfere with the differentiation of naïve T-cells into IL-17-expressing Th17 cells. Thus, in certain embodiments, the present invention provides a method for treating a Th17-mediated or IL-17-mediated disorder comprising the step of administering to a patient in need thereof a compound of the present invention or a pharmaceutically acceptable composition thereof.

As used herein, the terms "Th17-mediated" disorder and "IL-17-mediated" disorder means any disease or other deleterious condition in which Th17 or IL-17 is known to play a role. Accordingly, another embodiment of the present invention relates to treating or lessening the severity of one or more diseases in which Th17 or IL-17 is known to play a role including, but not limited to, autoimmune diseases, inflammatory diseases, infectious diseases, angiogenesis, and organ protection during transplantation.

The compounds and pharmaceutical compositions of the present invention may be used in treating or preventing diseases or conditions including, but not limited to, asthma, arthritis, inflammatory diseases (e.g., Crohn's disease, rheumatoid arthritis, psoriasis, dry eye syndrome), proliferative diseases (e.g., cancer, benign neoplasms, diabetic retinopathy), cardiovascular diseases, malaria, autoimmune diseases (e.g., rheumatoid arthritis, lupus, multiple sclerosis, psoriasis, scleroderma, or dry eye syndrome), and T-cell neoplasms (e.g., mature T-cell leukemias, nodal peripheral T-cell lymphomas, extranodal PTCL, and cutaneous T-cell lymphoma). Inventive compounds and pharmaceutical compositions thereof may be administered to animals, preferably mammals (e.g., domesticated animals, cats, dogs, mice, rats), and more preferably humans. Any method of administration may be used to deliver a provided compound or pharmaceutical composition to the animal. In certain embodiments, a provided compound or pharmaceutical composition is administered orally. In other embodiments, a provided compound or pharmaceutical composition is administered parenterally.

In certain embodiments, the present invention provides methods for treating or lessening the severity of autoimmune diseases including, but not limited to, acute disseminated encephalomyelitis, alopecia universalis, alopecia areata, Addison's disease, ankylosing spondylosis, antiphospholipid antibody syndrome, aplastic anemia, arthritis, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, celiac disease, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, dry eye syndrome, endometriosis, dysautonomia, essential mixed cryoglobulinemia, fibromyalgia, fibromyositis, glomerulonephritis, idiopathic pulmonary fibrosis, Goodpasture's syndrome, Graves' disease, Guillain-Barre syndrome, Hashimoto's thyroiditis, IgA neuropathy, inflammatory bowel disease, interstitial cystitis, juvenile arthritis, lichen planus, Meniere's disease, mixed connective tissue disease, type 1 or immune-mediated diabetes mellitus, juvenile arthritis, multiple sclerosis, myasthenia gravis, neuromyotonia, opsoclonus-myoclonus syndrome, optic neuritis, Ord's thyroiditis, osteoarthritis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, rheumatoid arthritis, sarcoidosis, scleroderma, Sjogren's syndrome, stiff-man syndrome, Still's disease, systemic lupus erythematosus, takayasu arteritis, temporal arteristis/giant cell arteritis, idiopathic thrombocytopenic purpura, ulcerative colitis, uveitis, vasculitides such as dermatitis herpetiformis vasculitis, vitiligo, vulvodynia, warm autoimmune hemolytic anemia, and Wegener's granulomatosis.

In some embodiments, the present invention provides a method for treating or lessening the severity of one or more diseases and conditions, wherein the disease or condition is selected from immunological conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, the present invention provides a method for treating or lessening the severity of an inflammatory disease including, but not limited to, asthma, appendicitis, Blau syndrome, blepharitis, bronchiolitis, bronchitis, bursitis, cervicitis, cholangitis, cholecystitis, chronic obstructive pulmonary disease (COPD), chronic recurrent multifocal osteomyelitis (CRMO), colitis, conjunctivitis, cryopyrin associated periodic syndrome (CAPS), cystitis, dacryoadenitis, dermatitis, dermatomyositis, dry eye syndrome, encephalitis, endocarditis, endometritis, enteritis, enterocolitis, epicondylitis, epididymitis, familial cold-induced autoinflammatory syndrome, familial Mediterranean fever (FMF), fasciitis, fibrositis, gastritis, gastroenteritis, hepatitis, hidradenitis suppurativa, laryngitis, mastitis, meningitis, mevalonate kinase deficiency (MKD), Muckle-Well syndrome, myelitis myocarditis, myositis, nephritis, oophoritis, orchitis, osteitis, inflammatory osteolysis, otitis, pancreatitis, parotitis, pericarditis, peritonitis, pharyngitis, pleuritis, phlebitis, pneumonitis, pneumonia, proctitis, prostatitis, pulmonary fibrosis, pyelonephritis, pyoderma gangrenosum and acne syndrome (PAPA), pyogenic sterile arthritis, rhinitis, salpingitis, sinusitis, stomatitis, synovitis, systemic juvenile rheumatoid arthritis, tendonitis, TNF receptor associated periodic syndrome (TRAPS), tonsillitis, undifferentiated spondyloarthropathy, undifferentiated arthropathy, uveitis, vaginitis, vasculitis, vulvitis, chronic inflammation resulting from chronic viral or bacteria infections, orpsoriasis (e.g., plaque psoriasis, pustular psoriasis, erythrodermic psoriasis, guttate psoriasis or inverse psoriasis).

In certain embodiments, the present invention provides methods for treating or lessening the severity of arthropathies and osteopathological diseases including, but not limited to, rheumatoid arthritis, osteoarthrtis, gout, polyarthritis, and psoriatic arthritis.

In certain embodiments, the present invention provides methods for treating or lessening the severity of hyperproliferative diseases including, but not limited to, psoriasis or smooth muscle cell proliferation including vascular proliferative disorders, atherosclerosis, and restenosis. In certain embodiments, the present invention provides methods for treating or lessening the severity of endometriosis, uterine fibroids, endometrial hyperplasia, and benign prostate hyperplasia.

In certain embodiments, the present invention provides methods for treating or lessening the severity of T-cell neoplasms including, but not limited to, mature T-cell leukemias (e.g., T-cell prolymphocytic leukemia (T-PLL), T-cell large granular lymphocytic leukemia (T-LGL), chronic lymphoproliferative disorders of NK-cells, aggressive NK-cell leukemia, adult T-cell leukemia/lymphoma (ATLL)), nodal peripheral T-cell lymphomas (PTCL) (e.g., peripheral T-cell lymphoma, not otherwise specified (PTCL-NOS), angioimmunoblastic T-cell lymphoma (AITL), anaplastic large-cell lymphoma (ALCL, either anaplastic lymphoma kinase (ALK) positive or ALK negative)), extranodal PTCL (e.g., extranodal NK-/T-cell lymphoma, nasal type, enteropathy-associated T-cell lymphoma (EATL), hepatosplenic T-cell lymphoma (HSTL), subcutaneous panniculitis-like T-cell lymphoma (e.g., $\alpha\beta$ only) (SPTCL)), and cutaneous T-cell lymphoma (CTCL) (e.g., mycosis fungoides (MF), Sézary syndrome (SS), primary cutaneous CD30$^+$ T-cell lymphoproliferative disease (e.g., primary cutaneous ALCL (C-ALCL), lymphomatoid papulosis (LYP)), primary cutaneous PTCLs (e.g., $\gamma\delta$ T-cell lymphoma, CD8$^+$ aggressive epidermotropic cytotoxic, CD4$^+$ small/medium).

In certain embodiments, the present invention provides methods for treating or lessening the severity of acute and chronic inflammatory diseases including, but not limited to, ulcerative colitis, inflammatory bowel disease, Crohn's disease, dry eye syndrome, allergic rhinitis, allergic dermatitis, cystic fibrosis, chronic obstructive bronchitis, and asthma.

In some embodiments, the present invention provides a method for treating or lessening the severity of a cardiovascular disorder including, but not limited to, myocardial infarction, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis, ischemic stroke, cardiac hypertrophy, and heart failure.

The present invention further includes a method for the treatment of mammals, including humans, which are suffering from one of the above-mentioned conditions or diseases. The method comprises that a pharmacologically active and therapeutically effective amount of one or more of the compounds of the present invention is administered to the subject in need of such treatment.

Pharmaceutical Compositions

The invention further relates to the use of provided compounds for the production of pharmaceutical compositions which are employed for the treatment and/or prophylaxis, and/or amelioration of the diseases and/or conditions as mentioned herein.

The invention further relates to the use of provided compounds for the production of pharmaceutical compositions.

The invention further relates to the use of provided compounds for the production of pharmaceutical compositions for inhibiting or treating fibrosis.

The invention further relates to the use of provided compounds for the production of pharmaceutical compositions which can be used for treating, preventing, or ameliorating of diseases responsive to inhibiting IL-17 production, such as autoimmune or inflammatory diseases, such as any of those diseases mentioned herein.

The exact amount required will vary from subject to subject, depending on the species, age, and general condition of the subject, the particular agent, its mode of administration, its mode of activity, and the like. The compounds of the invention are preferably formulated in dosage unit form for ease of administration and uniformity of dosage. It will be understood, however, that the total daily usage of the agents of the present invention will be decided by the attending physician within the scope of sound medical judgment. The specific therapeutically effective dose level for any particular patient or organism will depend upon a variety of factors including the disorder being treated and the severity of the disorder; the specific agent employed; the age, body weight, general health, sex, and diet of the patient; the time of administration, route of administration, and rate of excretion of the specific agent employed; the duration of the treatment; drugs used in combination or coincidental with the specific agent employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, an agent of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, an inventive compound is administered at a dose that is below the dose at which the agent causes non-specific effects. In certain embodiments, an inventive compound is administered at a dose that does not cause generalized immunosuppression in a subject.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents such CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as poly(lactide-co-glycolide). Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active agent.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this invention. Additionally, the present invention contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., quids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

It will also be appreciated that the agents and pharmaceutical compositions of the present invention can be employed in combination therapies, that is, the agents and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent), or they may achieve different effects (e.g., control of any adverse effects).

In still another aspect, the present invention also provides a pharmaceutical pack or kit comprising one or more containers filled with one or more of the ingredients of the pharmaceutical compositions of the present invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

Methods of Identifying Subjects in Need of Th17 Modulation

In various embodiments of the invention, suitable in vitro or in vivo studies are performed to determine whether administration of a specific therapeutic that modulates the development of IL-17 expressing cells, such as IL-17 expressing effector T-cells, e.g., Th17 cells, is indicated for treatment of a given subject or population of subjects. For example, subjects in need of treatment using a compound that modulates IL-17 expressing cell development, such as IL-17 expressing effector T-cell development, e.g., Th17 cell development, are identified by obtaining a sample of IL-17 expressing cells, such as IL-17 expressing effector T-cells, e.g., Th17 cells from a given test subject and expanding the sample of cells. If the concentration of any of a variety of inflammatory cytokine markers, including IL-17, IL-17F, IL-6, IL-21, IL-2, and TNFα, also increases as the cell population expands, then the test subject is a candidate for treatment using any of the compounds, compositions, and methods described herein.

Subjects in need of treatment are also identified by detecting an elevated level of IL-17 expressing cells, such as IL-17 expressing effector T-cells, e.g., Th17 cells, or an elevated level of a Th17 cell-associated cytokine or a cytokine that is secreted by a Th17 cell. Cytokine levels to be evaluated include IL-17, IL-17F, IL-6, IL-21, TNFα, and GM-CSF. The cytokine IL-17, as well as other cytokines such as IL-6, IL-21, IL-2, TNFα, and GM-CSF, are typically induced during inflammation and/or infection. Thus, any elevated level of expression of these cytokines in a subject or biological sample as compared to the level of expression of these cytokines in a normal subject is useful as an indicator of a disease state or other condition where treatment with an inventive compound is desirable. Studies have shown that the levels of IL-17 in healthy patient serum is less than 2 pg/mL (i.e., below the detection limit of the assay used), while patients with liver injury had levels of IL-17 expression in the range of 2-18 pg/mL and patients with rheumatoid arthritis had levels greater than 100 pg/mL (see Yasumi et al., *Hepatol Res*. (2007) 37: 248-254, and Ziolkowska et al., *J. Immunol*. (2000) 164: 2832-2838, each of which is incorporated herein by reference). Thus, detection of an expression level of IL-17 greater than 2 pg/mL in a subject or biological sample is useful in identifying subjects in need of treatment with an inventive compound or composition thereof.

A subject suffering from or at risk of developing a Th17-related and/or IL-17-related disease such as an autoimmune disease, a persistent inflammatory disease, or an infectious disease is identified by methods known in the art. For example, subjects suffering from an autoimmune disease, persistent inflammatory disease, or an infectious disease may be diagnosed based on the presence of one or more signs or symptoms associated with a given autoimmune, persistent inflammatory, or infectious disease. Common symptoms include, for example, inflammation, fever, loss of appetite, weight loss, abdominal symptoms, such as, for example, abdominal pain, diarrhea, or constipation, joint pain or aches (arthralgia), fatigue, rash, anemia, extreme sensitivity to cold (Raynaud's phenomenon), muscle weakness, muscle fatigue, change in skin or tissue tone, shortness of breath or other abnormal breathing patterns, chest pain or constriction of the chest muscles, abnormal heart rate (e.g., elevated or lowered), light sensitivity, blurry or otherwise abnormal vision, and reduced organ function.

Subjects suffering from an autoimmune disease such as, e.g., multiple sclerosis, rheumatoid arthritis, Crohn's disease, are identified using any of a variety of clinical and/or laboratory test such as, physical examination, radiological examination and blood, urine, and stool analysis to evaluate immune status. For example, subjects suffering from an infectious disease such as Lyme disease are identified based on symptoms, objective physical findings (such as erythema migrans, facial palsy, or arthritis), and a history of possible exposure to infected ticks. Blood test results are generally used to confirm a diagnosis of Lyme disease.

Determination of the Biological Effect of Th17 Modulation

In various embodiments of the invention, suitable in vitro or in vivo studies are performed to determine the effect of a specific therapeutic that modulates the development of IL-17 expressing cells, such as IL-17 expressing effector T-cells, e.g., Th17 cells, and whether its administration is indicated for treatment of a given subject or population of subjects. For example, the biological effect of a selective Th17 inhibitor, such as a compound of the present invention, is monitored by measuring the level of IL-17 production and/or the number of IL-17 expressing cells, such as IL-17 expressing effector T-cells, e.g., Th17 cells in a patient-derived sample. The biological effect of an inventive compound is also measured by physical and/or clinical observation of a patient suffering from, or at risk of developing, a Th17-related and/or IL-17-related disease such as an autoimmune disease, persistent inflammatory disease, or an infectious disease. For example, administration of a specific Th17 inhibitor to a patient suffering from a Th17-related disease and/or an IL-17-related disease is considered successful if one or more of the signs or symptoms associated with the disorder is alleviated, reduced, inhibited, or does not progress to a further, i.e., worse, state.

These and other aspects of the present invention will be further appreciated upon consideration of the following Examples, which are intended to illustrate certain particular embodiments of the invention but are not intended to limit its scope, as defined by the claims.

EXAMPLES

Boc-Protection of Halofuginone

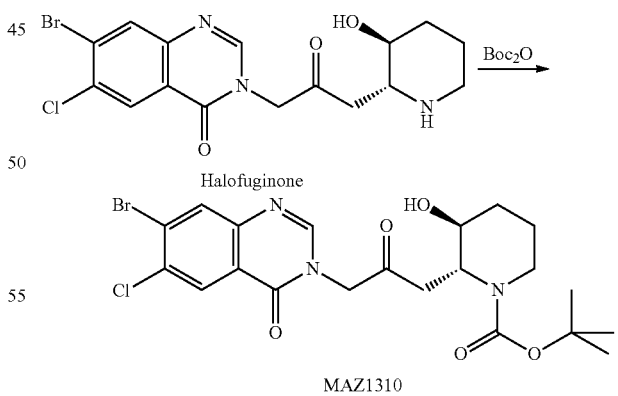

MAZ1310

982 mg di-tert-butyldicarbonate in 10 mL DMF were added to a solution of 1.5 g halofuginone hydrobromide (+/−) and 1.3 mL diisopropylethylamine in 100 mL. The reaction mixture was stirred for 16 h at room temperature. After the addition of water the aqueous layer was extracted three times with diethyl ether. The combined organic layers were dried over sodium sulfate and evaporated to dryness.

The crude product was purified on silica gel with dichloromethane/methanol to yield the desired Boc protected racemic product as white solid in quantitative yield. ¹H NMR (300 MHz, DMSO) δ 8.22 (s, 1H), 8.20 (s, 1H), 8.14 (s, 1H), 5.02 (s, 2H), 4.79 (d, J=2.8 Hz, 1H), 4.48 (t, J=6.8 Hz, 1H), 3.80 (d, J=12.4 Hz, 1H), 3.60 (s, 1H), 2.98 (dd, J=15.8, 7.5 Hz, 1H), 2.76 (d, J=19.5 Hz, 1H), 2.72-2.55 (m, 1H), 1.70 (q, J=13.4 Hz, 2H), 1.54 (d, J=9.7 Hz, 1H), 1.37 (m, 10H).

Reduction of Boc-HF with NaBH₄

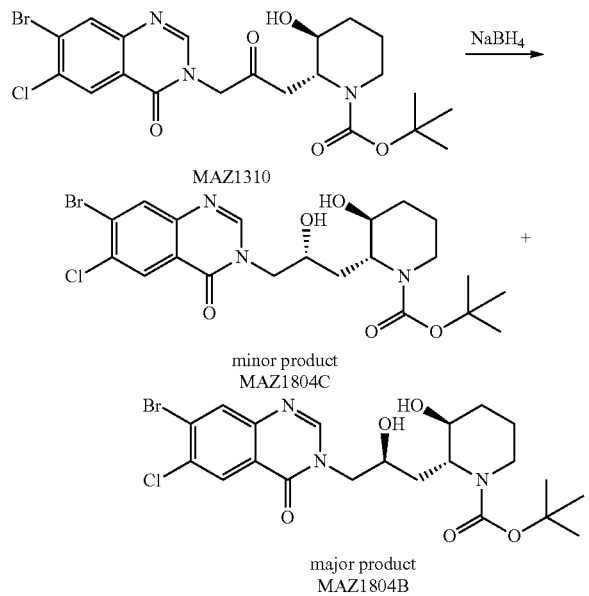

207 mg (0.5 mmol) MAZ1310 (+/−) were suspended in 10 mL methanol and 3 mL THF. Following cooling to 0° C., 10 mg (0.3 mmol) NaBH₄ were added and the clear reaction mixture was stirred for additional 60 min. Upon stirring at 0° C. the desired product precipitated from solution as white solid. The solid was isolated by filtration and recrystallized from methanol to afford pure product. The mother liquor was concentrated and purified by HPLC on an Atlantis column (Waters) using water/MeCN (with 0.1% FA) as mobile phase to yield additional MAZ1804B and the diastereomer MAZ1804C as minor product (the other product MAZ1804A-reduced quinazolone of MAZ1804B/C). ¹H NMR of MAZ1804B (racemic) (300 MHz, DMSO) δ 8.26 (s, 1H), 8.22 (s, 1H), 8.12 (s, 1H), 4.99 (s, 1H), 4.57 (s, 1H), 4.23 (s, 1H), 4.12 (d, J=11.9 Hz, 1H), 3.95-3.70 (m, 3H), 3.61 (s, 1H), 2.75 (s, 1H), 1.93-1.45 (m, 5H), 1.40 (s, 9H), 1.25 (d, J=11.9 Hz, 1H). HRMS of MAZ1804B: calc.: 518.0884 found: 518.0885 [M+H].

Deprotection to Yield Halofuginol

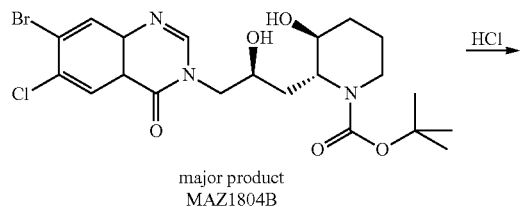

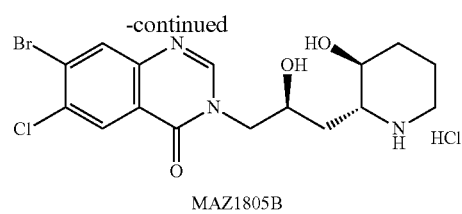

200 uL HCl (4M in dioxane) were added to a solution of 10 mg MAZ1804B (+/−) in 2 ml methanol/THF (1:1). The reaction mixture was stirred over night at room temperature. The desired product was obtained following removal of the solvent under reduced pressure in quantitative yield without the need for further purification as white powder as the hydrochloride salt (racemic). ¹H NMR (300 MHz, DMSO) δ 8.80-8.45 (m, 1H), 8.32 (s, 1H), 8.25 (s, 1H), 8.15 (s, 1H), 4.09 (d, J=10.8 Hz, 1H), 3.85 (dd, J=14.0, 8.4 Hz, 1H), 3.44 (td, J=9.0, 3.6 Hz, 1H), 3.15 (d, J=12.7 Hz, 1H), 2.98 (d, J=7.3 Hz, 1H), 2.83 (d, J=11.0 Hz, 1H), 2.14 (dt, J=14.5, 3.5 Hz, 1H), 1.98-1.72 (m, 2H), 1.68-1.31 (m, 2H). HRMS: calc.: 418.0357 found: 518.0360 [M+H].

Alternative Synthesis Yields Epimer as Major Product

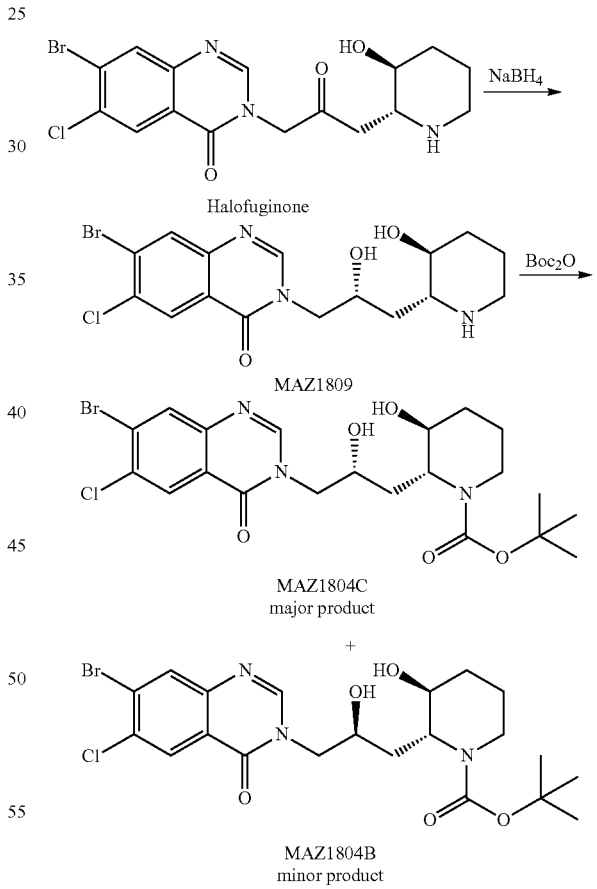

12 mg halofuginone hydrochloride (+/−) and 30 μL diisopropylethyl amine were dissolved in 2 mL methanol and cooled to 0° C. 5 mg NaBH₄ were added and the reaction was stirred for 1 hour at 0° C. and warmed to room temperature. LC/MS analysis indicated full consumption of the starting material. The solvent was removed under reduced pressure and the product was used without further purification. 1 mg of crude MAZ1809 were dissolved in DMF, followed by the addition of 1 mg Boc$_2$O. The reaction was stirred at room temperature and analyzed by LC/MS. Comparison to reference standards of MAZ1804B and MAZ1804C show that MAZ1804C is formed as major product.

Inhibition of ProRS Activity by HF and HFolA

Activity of the Prolyl tRNA synthetase domain of EPRS (ProRS) was measured as $^3$H Pro incorporation into the charged tRNA pool. Halofuginone (HF) or the active diastereomer of HFol (HFolA) were added to the reaction at the indicated concentrations. HFolA is a potent inhibitor of ProRS, approximately 2-fold less potent than HF (FIG. 24). The prolyl tRNA synthetase domain of human EPRS (ProRS) was expressed in *E. coli* with a 6-His tag and purified as described (Heacock et al. *Bioorganic Chemistry* 24 (1996)). Purified enzyme was visualized as a single band by Laemmli gel electrophoresis/Coomassie staining. Enzymatic activity was assayed using incorporation of $^3$H Pro into the tRNA fraction essentially as described (Ting et al., *J. Biol. Chem.* 267:17701-9 (1992)), except that the charged tRNA fraction was isolated by rapid batchwise binding to Mono Q sepharose (Jahn et al. *Nucleic Acids Res.* 19:2786 (1991)) (GE Healthcare) and quantitated by liquid scintillation counting. HFolB was tested similarly and shown to be inactive in the assay (FIG. 25).

Activation of the Amino Acid Response (AAR) by HF and HFolA in Intact Cells

AAR activation in primary human fibroblasts was measured as an induction of the AAR response gene cystathionase relative to a housekeeping gene control (GAPDH). Cells were treated with the indicated concentrations of HF or HFolA, and 4 hours later harvested for analysis of gene expression by Q-RT-PCR using the Roche LightCycle UPR system as described below. HFolA induced cystathionase with a potency within 5-10 fold relative to HF.

HF Limits Proline-Utilization During Translation In Vitro

Figure 2A:
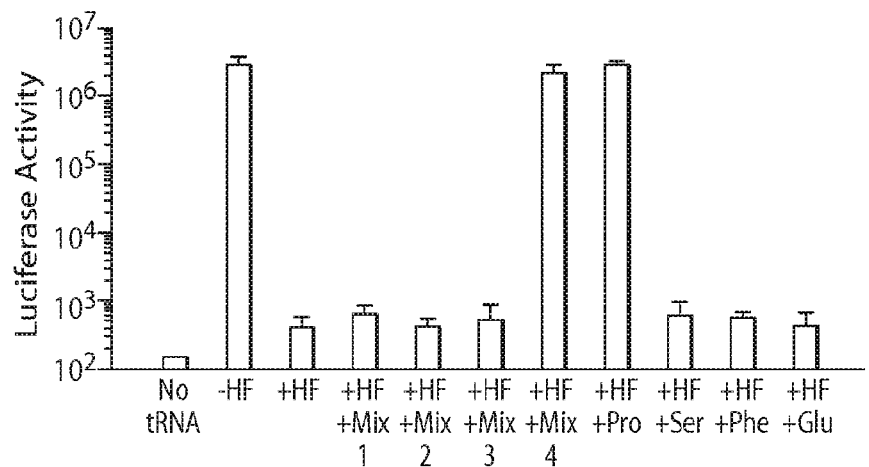
FIG. 2 shows that halofuginone and febrifugine inhibit prolyl tRNA synthetase activity in vivo. A) Rabbit reticulocyte lysate (RRL) was incubated with luciferase mRNA and translation quantitated in a luminescence assay. A solution of a mixture of amino acids or individual amino acids was added to yield 1 mM of each in the reaction to rescue translational inhibition. Mix1: Asn, Arg, Val, Glu, Gly; Mix2: Lys, Ile, Tyr, Asp, Trp; Mix 3: His, Met, Leu, Ala, Thr; Mix 4: Ser, Phe, Pro, Gln. Note log scale of y-axis. B) Effect of halofuginone (HF) and its derivatives in the presence or absence of proline supplementation on translation were assayed as in FIG. 2A. Error bars reflect standard deviation of triplicate determinations. C) Short myc-tagged polypeptides of identical sequence (see Examples) with the exception that NoPropep lacks proline, while Propep contains a proline dipeptide, were translated in RRL in the presence of indicated inhibitors (each at a concentration of 1 μM, proline added at 1 mM). Translation was examined by anti-myc Western blot. D) $^{14}C$ Pro or $^{35}S$ Met (Perkin-Elmer) were incubated with RRL (Promega) and 1 μg/μl total bovine tRNA (Sigma) in the presence or absence of HF or MAZ1310 for 10 min, tRNA was isolated using a MirVana tRNA isolation kit (Ambion), and radioactivity in tRNA was measured by liquid scintillation counting. Error bars reflect standard deviation of triplicate determinations.
Figure 2B:
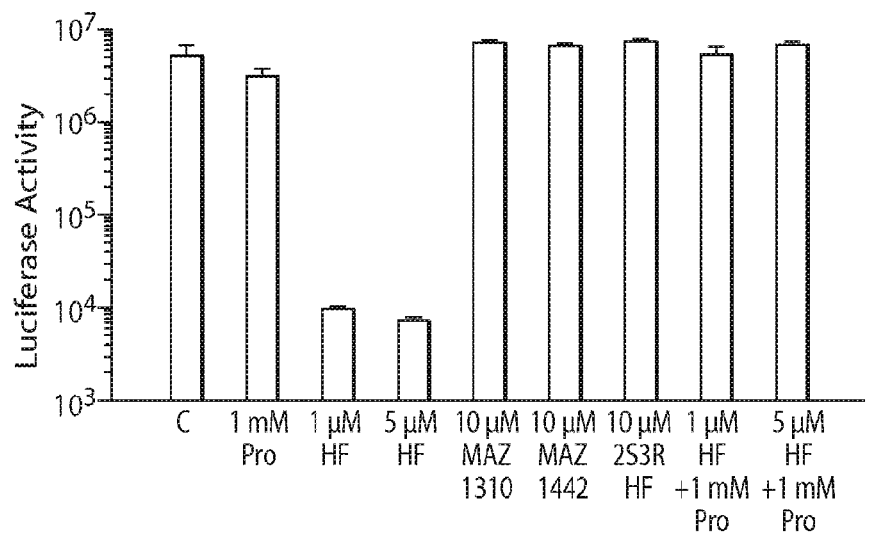

HF activates the AAR pathway in T-cells and fibroblasts, and AAR pathway activation selectively inhibits the development of pro-inflammatory Th17 cell (Sundrud et al. *Science* 324:1334-8 (2009)). In intact cells, amino acid incorporation into tRNA can be limited either by inhibiting the enzymes responsible for tRNA charging, or by decreasing the intracellular levels of amino acid through effects on transport, synthesis, or catabolism. To distinguish between these possibilities, we tested the effects of HF and febrifugine (FF) in a cell free in vitro translation system (rabbit reticulocyte lysate, RRL) where amino acid availability for translation can be controlled directly. Both HF and FF inhibited the translation of luciferase RNA in RRL; supplementation of RRL with excess amino acids established that only proline restores translation inhibited by HF (FIG. 2A). The activities of FF and of HF as antimalarials (Kobayashi et al. *J. Org. chem.* 64:6833-6841 (1999)) and of HF as an inhibitor of Th17 cell differentiation (Sundrud et al. *Science* 324:1334-8 (2009)) are enantiospecific. Only the 2R,3S isomer of HF (2), which matches the absolute configuration of FF, exhibits biological activity. Consistent with these observations, the 2S,3R isomer of HF also has no activity in the RRL assay (FIG. 2B). Additionally, HF-derivatives that lack activity in cell-based assays (MAZ1310 (3) and MAZ1442 (4)) have no activity in the RRL assay (FIG. 2B). These data suggest that the ability of FF and HF to inhibit proline utilization is functionally linked to the bioactivities of these compounds.

Figure 2C:
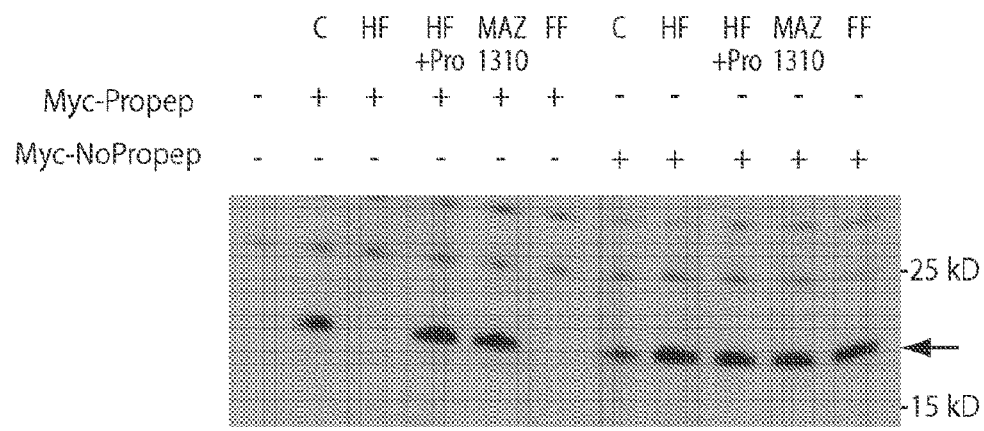

To confirm that HF/FF-inhibition specifically targets the utilization of proline in translation, we examined how these compounds affected the translation of a pair of glutamate-rich (24 of 118 amino acids), synthetic polypeptides that differ only with respect to the presence of prolyl residues. We synthesized cDNAs encoding two epitope-tagged polypeptides. The first cDNA, designated Propep, encodes a proline dipeptide, and the second cDNA, called Nopropep, encodes a proline-free peptide. HF and FF prevent translation of Propep, but have no effect on the translation of Nopropep (FIG. 2C), establishing that proline utilization is the sole target for the inhibitory effect of these compounds on translation in RRL. Since the synthetic peptides are rich in glutamate, the unimpaired translation of Nopropep in the presence of HF/FF argues strongly against the inhibition of the glutamyl-tRNA synthetase activity of EPRS under these conditions.

Figure 2D:
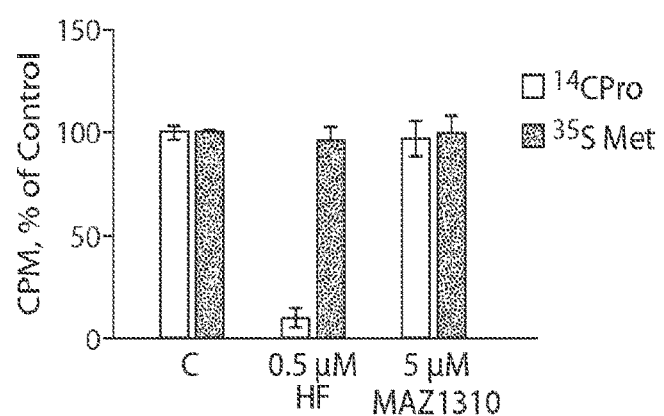
Figure 8:
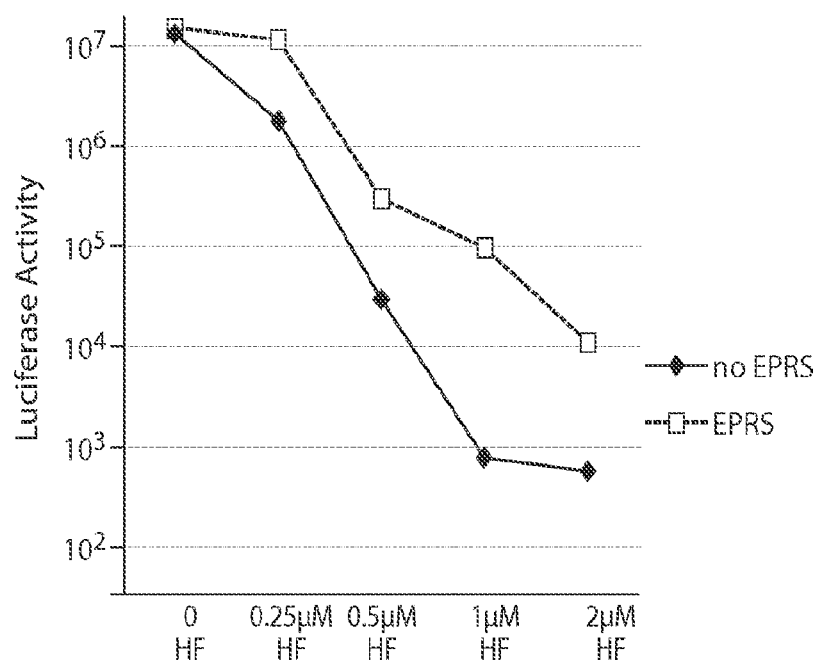
FIG. 8 shows that addition of purified EPRS rescues halofuginone inhibition of translation in vitro. Inhibition of translation in RRL was measured as in FIG. 2 in the absence or presence of low (80 ng) or high (0.5 µg) concentrations of add EPRS purified from rat liver. Note log scale.

Next, we directly examined the effects of HF on prolyl-tRNA charging in the RRL system. RRL were supplemented with $^{14}$C-Pro Or $^{35}$S-Met in the presence or absence of HF, and total tRNA was isolated (FIG. 2D). HF inhibited the incorporation of $^{14}$C-Pro, but not $^{35}$S-Met, into tRNA at doses comparable to those necessary to inhibit translation, indicating that inhibition of amino acid utilization by HF is specific for proline. Moreover, addition of EPRS purified from rat liver to RRL substantially reduces the sensitivity of in vitro translation by RRL to HF inhibition (FIG. 8), establishing that EPRS is the critical target for inhibition of translation by these compounds in RRL.

HF is a Competitive Inhibitor of Purified ProRS

Figure 9:
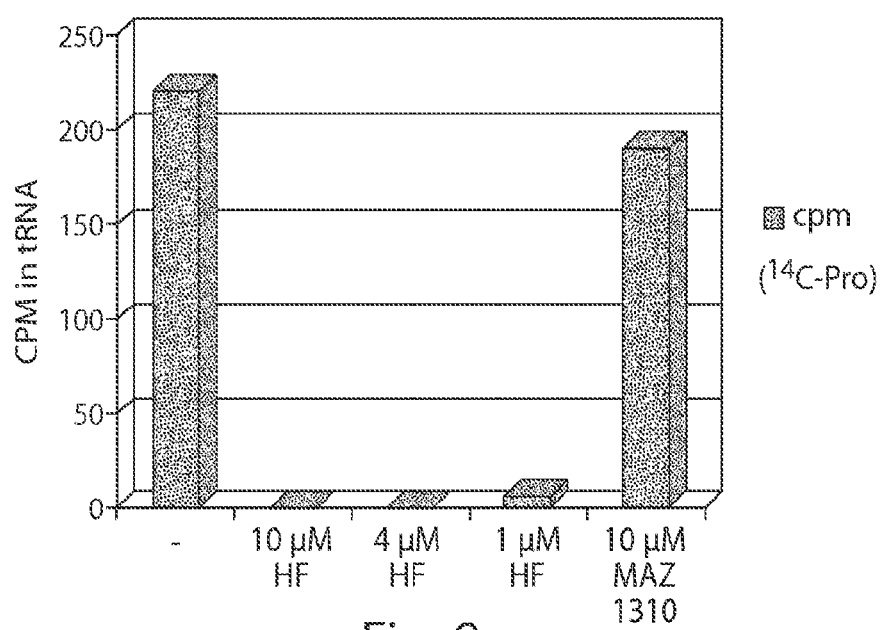
FIG. 9 shows that MAZ1310 does not block ProRS activity. ProRS activity was assayed as in FIGS. 10 and 11, except that $^{14}$C Proline was used as trace label rather than $^3$H Pro.
Figure 10:
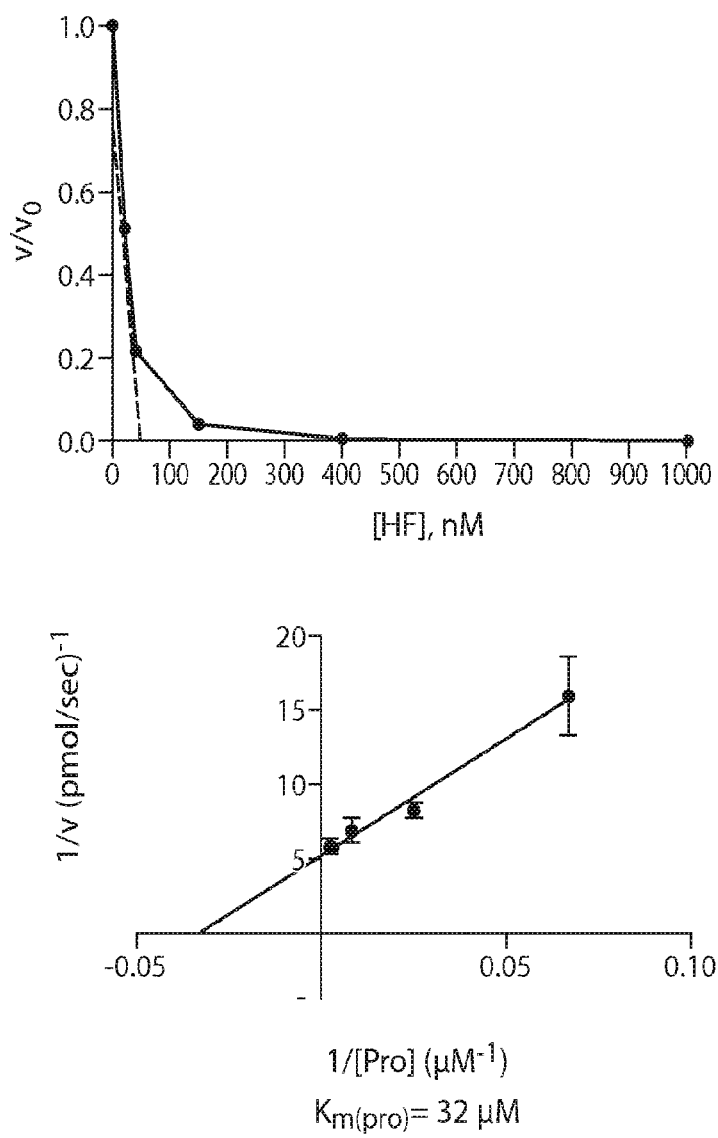
FIG. 10 depicts determination of [$E_t$] and $K_{m(pro)}$ for purified ProRS. Left Panel: The concentration of active ProRS [$E_t$] was determined by the method of Copeland (Copeland, *Methods Biochem Anal* 46:1-265 (2005)). Briefly, the fractional velocity is plotted as a function of inhibitor concentration, measured over a concentration range at which [$E_t$] is substantially higher than the $K_{i(app)}$. The point at which the linear portion of the concentration response line intersects the X-axis provides the concentration of active enzyme in the reaction. Right Panel: ProRS synthetase activity was measure as described in methods for FIG. 2A. Triplicate determinations at proline concentrations of 15, 40, 120, 240, and 480 µM were done and reaction velocity plotted versus proline concentration as a double reciprocal (Lineweaver-Burke) plot using linear regression with Graphpad software.
Figure 11:
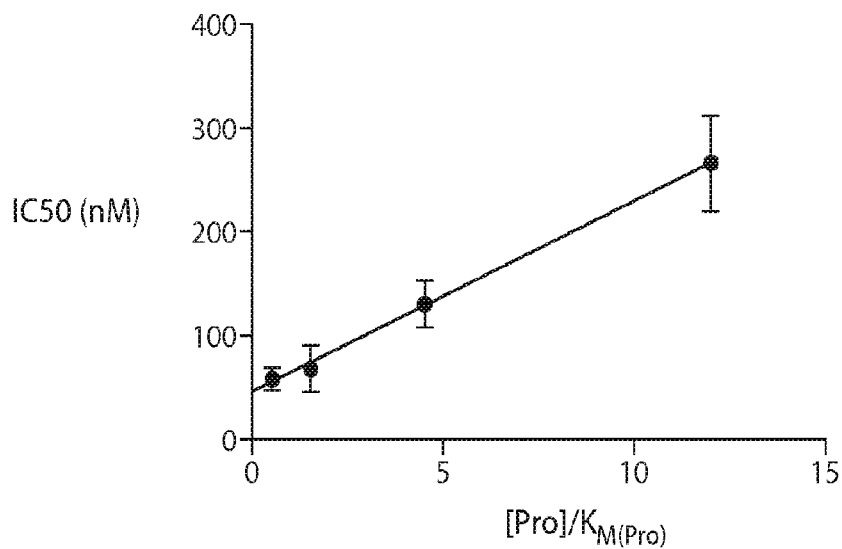
FIG. 11 shows that halofuginone inhibits the purified prolyl tRNA synthetase domain of EPRS competitively with proline. The prolyl tRNA synthetase domain of EPRS was expressed in *E. coli*, purified, and assayed as described, with modifications indicated in the Examples. IC$_{50}$ values for HF at proline concentrations of 20, 60, 180, and 480 µM were determined as shown in FIG. 12, $K_{m\ (Pro)}$ and $E_t$ values were determined as shown in FIG. 10. $K_i$ value for HF was determined from the slope of IC$_{50}$ vs. [Pro]/$K_{m\ (Pro)}$ by linear regression using Prism Graphpad software. Standard error is shown.
Figure 12:
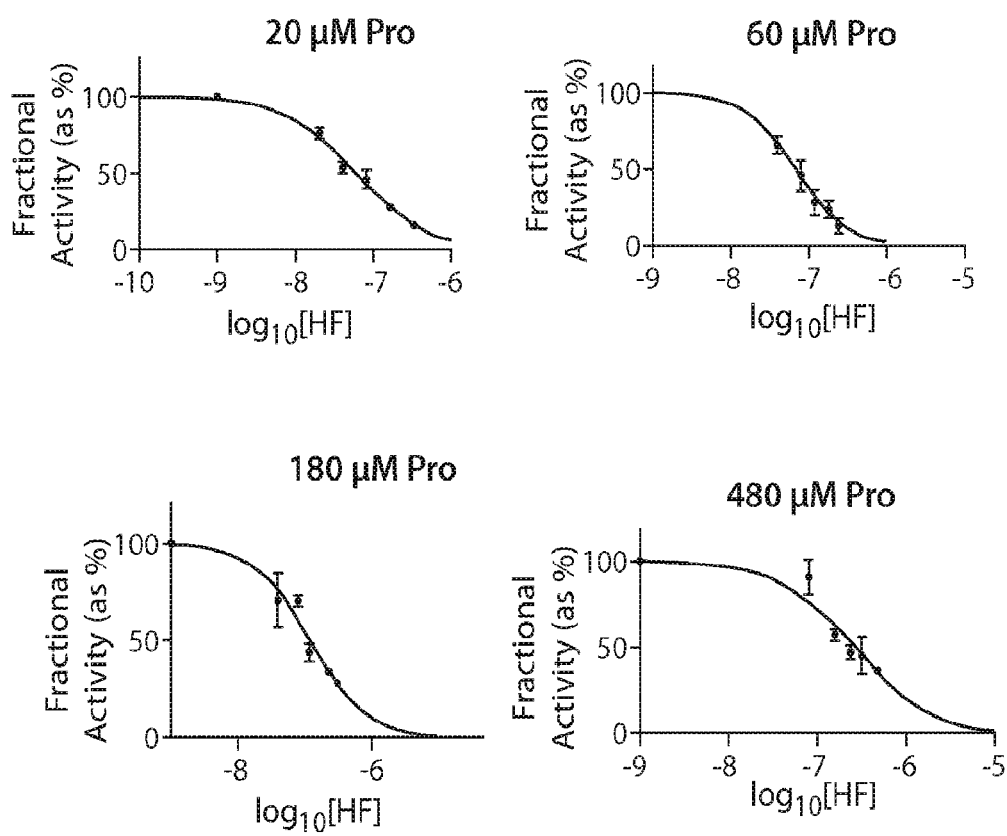
FIG. 12 shows IC$_{50}$ for HF inhibition of ProRS activity at different proline concentrations. Inhibition of prolyl tRNA synthetase activity was determined with triplicate determinations at the indicated concentrations of proline, and 1 nM (no inhibition compared to 0 nM, used for purposes of log plot), 40 nM, 80 nM, 160 nM, 240 nM, 320 nM, and 480 nM concentrations of HF. Curves were fit by nonlinear regression using the equation Y=100/(1+10^(([HF]−Log IC50))) where Y is reaction velocity normalized as percentage to the uninhibited reaction.

To directly examine the mechanism of HF-mediated inhibition of EPRS, we tested the effect of HF on tRNA$^{Pro}$ charging using the ectopically expressed and purified prolyl tRNA synthetase domain of EPRS (ProRS). Preliminary analysis of the inhibition kinetics indicated that the apparent $K_i$ of HF for ProRS was similar to the concentration of ProRS enzyme in the tRNA charging assay. In this circumstance, a substantial fraction of the total inhibitor is bound to the enzyme during the assay, and therefore Michaelis-Menten analysis is not applicable. Alternative analytic approaches for tight binding inhibitors have been described (Ruan et al. *J. Biol. Chem.* 280:571-7 (2005) and are summarized in Copeland (Copeland *Methods Biochem. Anal.* 46:1-265 (2005)). In this approach the modality of inhibition can be determined from the relationship between the IC$_{50}$ of the inhibitor and varying substrate concentrations. For a tight binding competitive inhibitor, this relationship is given by: IC$_{50}$=K$_i$ (1+[S]/K$_m$)+0.5*E$_t$, where E$_t$ is the concentration of active enzyme in the reaction (determined by the method described by Copeland (Copeland *Methods Biochem. Anal.* 46:1-265 (2005)), FIG. 10). Competitive inhibition is reflected in a linear relationship (with positive slope) between IC$_{50}$ and [S]; the K$_i$ can be derived from the slope of the plot of IC$_{50}$ vs. [S]/K$_m$. This relationship is plotted for HF as inhibitor, and proline as substrate in FIG. 2A, using IC$_{50}$ values determined at proline concentrations between 20 and 480 nM (FIG. 11), and K$_{m(Pro)}$ determined as shown in FIG. 10. These data fit the model predicted for a tight binding inhibitor, acting competitively with proline. The slope of the resulting line yields a K$_i$ for HF of 18.3 nM+/−0.5. The HF derivative MAZ1310, had no inhibitory effect on ProRS activity (FIG. 9), consistent with its lack of activity in RRL (FIG. 2B) and biological assays (Sundrud et al. *Science* 324:1334-8 (2009)).

Figure 3A:
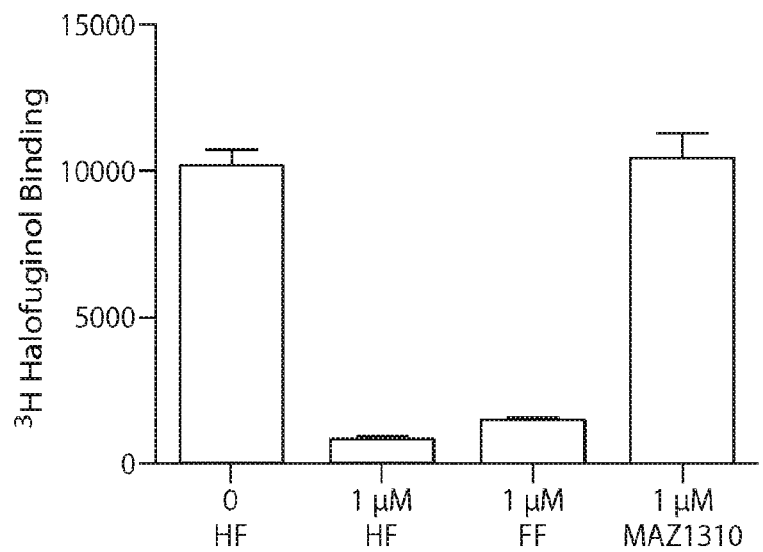
FIG. 3 shows that EPRS binds to halofuginol and determines sensitivity to halofuginol in cells. A) $[^3H]$-Halofuginol ($[^3H]$ HFol) binds specifically to ProRS. Purified 6-his tagged ProRS (amino acids 998-1513 of human EPRS) was immobilized on N-NTA beads and incubated for 10' at RT with 50 nM $[^3H]$-Halofuginol in the presence or absence of HF, febrifugine (FF), or the inactive HF derivative MAZ1310, 5 mM $MgCl_2$, and 2 mM ATP. Preliminary experiments established that binding was maximal by 10 min, and that inclusion of tRNA had no effect on $[^3H]$-HFol binding. B) $[^3H]$-HFol binding was assayed as described above in the presence of indicated concentrations of proline. C) EPRS depletion sensitizes cells to HF. IMR90 lung fibroblasts were treated with a siRNAs directed against EPRS (Dharmacon) or a control siRNA mixture for 48 hours, and then treated with HF for 2 hours (pGCN2) and examined for EPRS protein levels, GCN2 total protein and phospho-GCN2 by Western blot. D) EPRS depleted IMR90 cells were compared to control cells with respect to HF induction of the AAR marker CHOP by Q-PCR. Equal concentrations of total cellular protein were loaded in each Western blot lane. CHOP expression was standardized to expression of phosphoglycerate kinase 1 (PGK1) and glyceraldehyde-3-phosphate-dehydrogenase (GAPDH). Data shown are representative of three separate experiments.
Figure 3B:
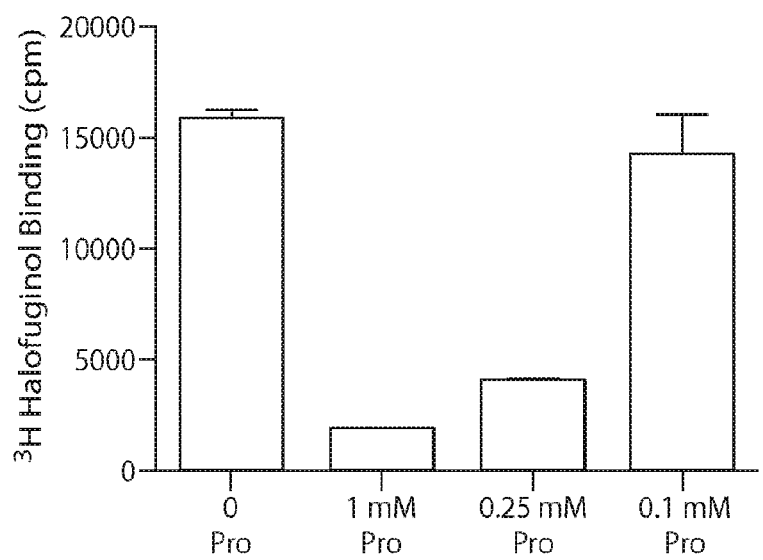
Figure 3C:
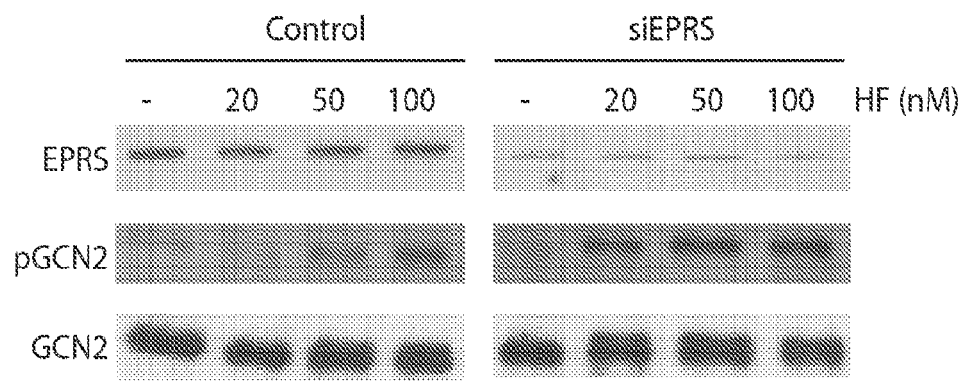
Figure 3D:
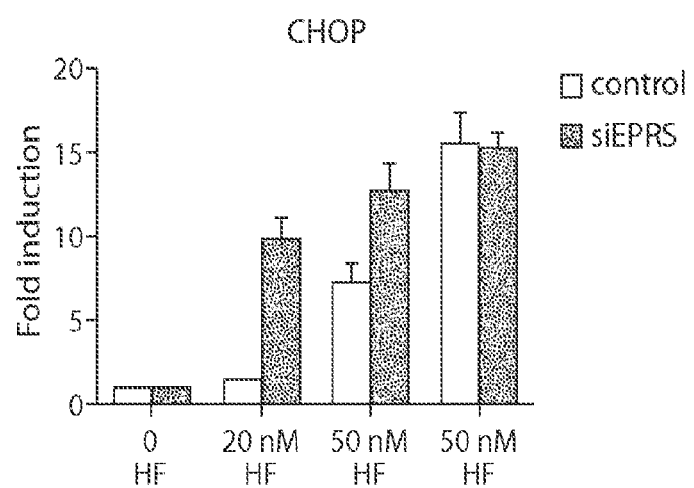
Figure 13:
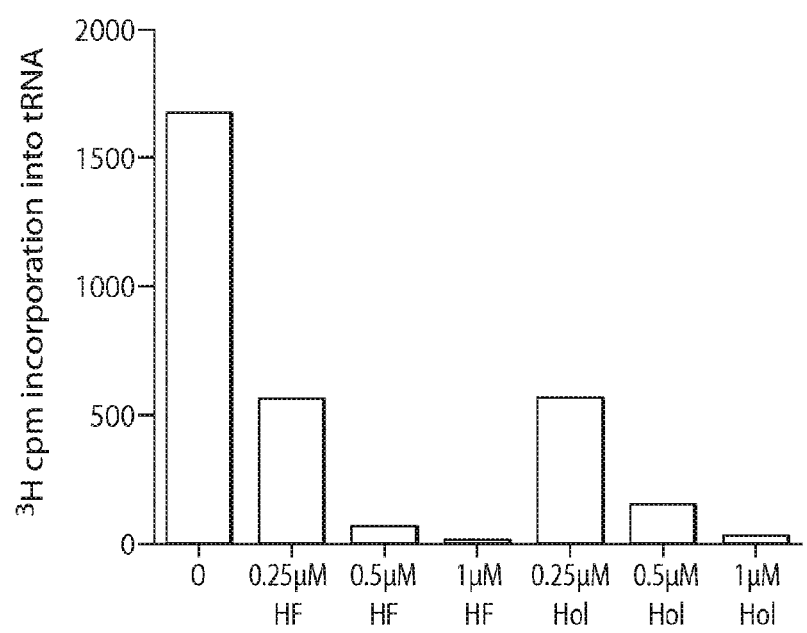
FIG. 13 shows that HFol inhibits ProRS activity. ProRS activity was measured as in FIGS. 10 and 11 at a concentration of 100 µM Pro.
Figure 14:
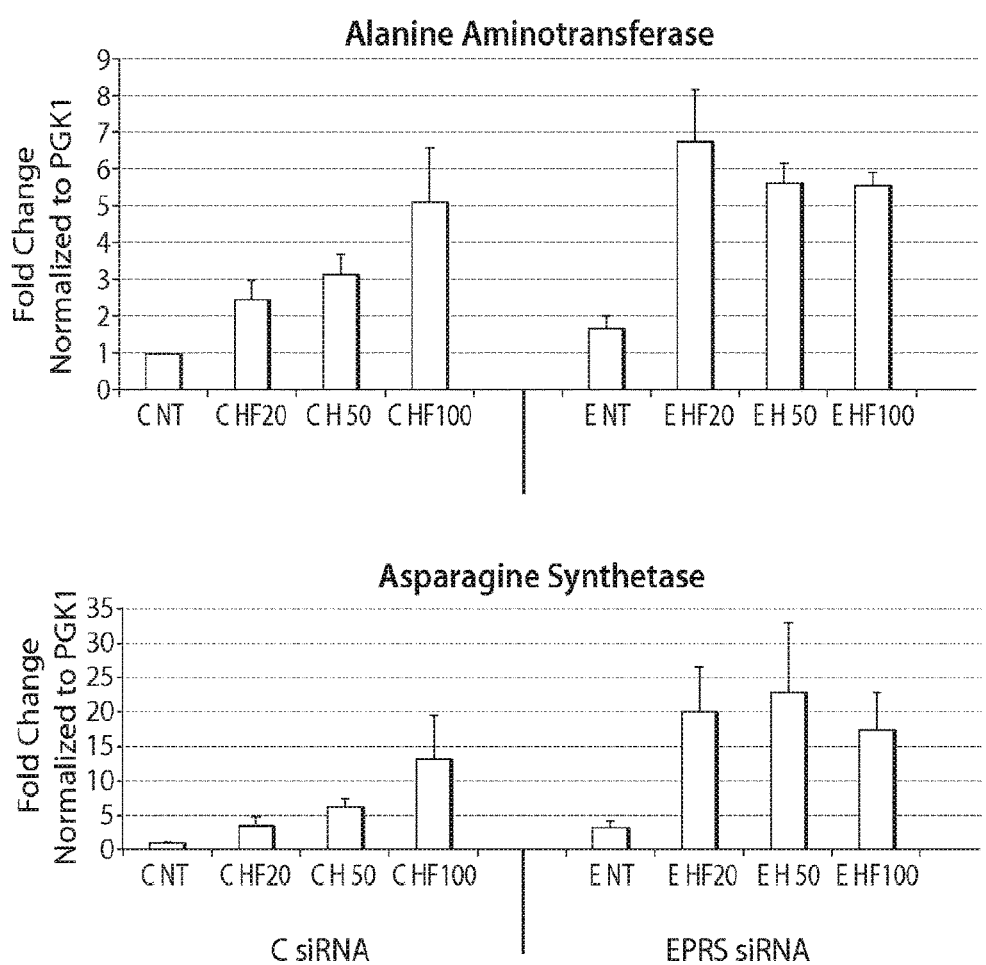
FIG. 14 shows that reduction of EPRS levels sensitizes cells for induction of AAR genes by halofuginone. siRNA depletion, HF treatment, and gene expression analysis were done as described for FIG. 2C.

To demonstrate direct binding of HF to ProRS, we used a [$^3$H]-labeled derivative of HF ([$^3$H]-HFol, [$^3$H]-5) that has been developed in our laboratory and which we named halofuginol (HFol) (5). HFol, in contrast to the previously reported diastereomer derived from febrifugine (6) (Kikuchi et al. *J. Med. Chem.* 45:2563-70 (2002)), retains potency similar to the parent compound for the inhibition of EPRS (FIG. 13). [$^3$H]-HFol bound directly to immobilized ProRS, and this binding was competed by HF and FF, but not by MAZ1310 (FIG. 3A). If HF indeed acts in cells by inhibition of EPRS activity, we reasoned that reducing EPRS levels would sensitize cells to the action of HF. We therefore used siRNA-mediated knockdown to reduce EPRS levels in lung fibroblasts, which have high endogenous levels of EPRS and are relatively resistant to the effects of HF (in comparison to MEFs). Reduction of EPRS levels significantly sensitized these cells to AAR activation following HF treatment, as indicated by induction of GCN2 autophosphorylation (FIG. 3C) and induction of the AAR-response genes CHOP (FIG. 3D). Similar sensitization of induction was seen for additional AAR-response genes asparagine synthetase and alanine aminotransferase (FIG. 14). These data establish that EPRS is the critical target through which HF activates the AAR pathway.

HF Binds to ProRS in an ATP-Dependent Manner

Figure 4A:
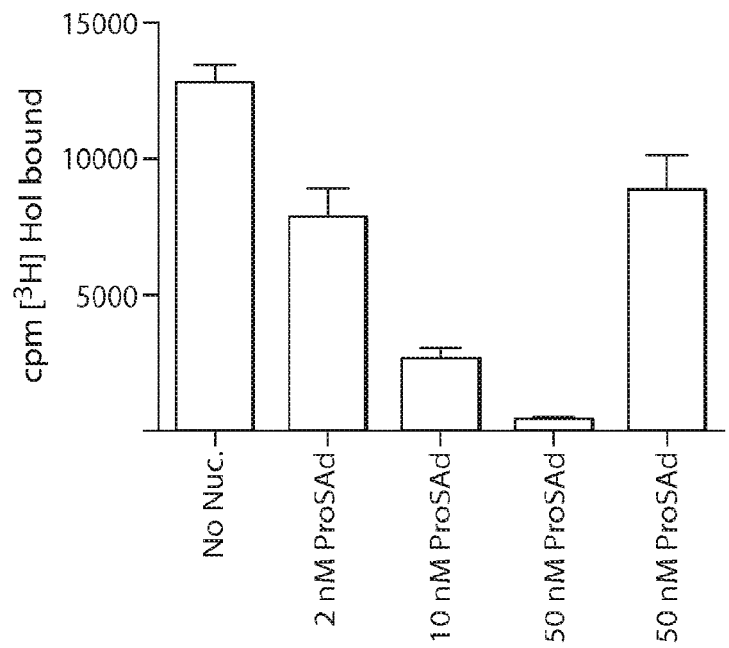
FIG. 4 shows that HFol binds to the active site of EPRS in an ATP dependent manner. A) A prolyl adenylate analog potently inhibits HFol binding. Prolyl sulfamoyl adenosine (ProSAd) or alanyl sulfamoyl adenosine (AlaSAd), analogs of the corresponding aminoacyl adenylate, were coincubated with $[^3H]$-HFol as in FIG. 2. B) HFol binding to EPRS requires ATP but not ATP hydrolysis. Binding of $[^3H]$-HFol was assayed as in FIG. 3, except that the nucleotide type and concentration was varied as indicated.

The competition kinetics between HF and proline for ProRS binding strongly predict that HFol binds directly to the enzyme active site of ProRS. Consistent with this hypothesis, high concentrations of proline inhibited the binding of [$^3$H]-HFol to the immobilized ProRS domain of EPRS (FIG. 3b). 5-O—[N-(L-prolyl)-sulfamoyl]adenosine (ProSAd, 7), a sulfamoyl analog of the charging reaction intermediate prolyl adenylate (Heacock et al. *Bioorganic Chemistry* 24 (1996)), very potently (10 nM) inhibited the binding of [$^3$H]-HFol to ProRS, supporting the interpretation that HF binds within the catalytic pocket (FIG. 4A). A higher concentration (50 nM) of an alanyl adenlylate analog, Ala-SAd, partially inhibited [$^3$H]-HFol binding to ProRS, possibly reflecting the ability of ProRS to accommodate non-cognate aminoacyl adenylates such as alanine in the enzyme active site (Splan et al. *J. Biol. Chem.* 283:7128-34 (2008)).

Figure 4B:
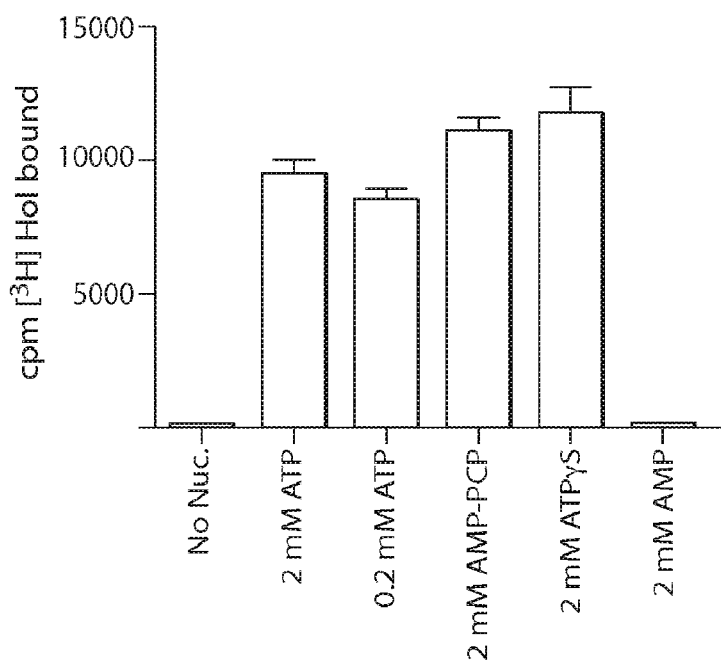

We next examined the effect of ATP on [$^3$H]-HFol binding to ProRS. ATP was essential for [$^3$H]-HFol binding (FIG. 4B), indicating that the mode of HF binding to the catalytic pocket is distinct from that of the reaction intermediate prolyl adenylate, since ATP and prolyl adenylate are expected to be mutually exclusive in the catalytic pocket (Yaremchuk et al. *J. Mol. Biol.* 309:989-1002 (2001)). The adenylylation reaction catalyzed by tRNA synthetases occurs through hydrolysis of the high-energy phosphate bond between the alpha and beta phosphates (Ibba et al. *Annu. Rev. Biochem.* 69:617-50 (2000)). AMP-CPP, an ATP analog that is non-hydrolyzable at the alpha-beta phosphate linkage, supports [$^3$H]-HFol binding in place of ATP, indicating that hydrolysis of the alpha-beta phosphate does not have a role in ATP-stimulated [$^3$H]-HFol binding (FIG. 4B). Similar results with ATPgS suggest that utilization of the g phosphate of ATP is also unlikely to be important for [$^3$H]-HFol binding to ProRS (FIG. 4B). AMP at 2 mM does not detectably facilitate [$^3$H]-HFol binding, however, indicating that the triphosphate component of ATP is important for HF interaction with ProRS. These data indicate that HF/HFol inhibits ProRS by binding to a portion of the catalytic site that includes, at least in part, the proline-binding pocket. The ATP requirement for HF binding suggests that HF is not acting as simply to mimic prolyl adenylate in the catalytic site, but rather requires an ATP-induced conformational change in the enzyme that enables inhibitor binding. Although we have not ruled out the possibility that ATP binds allosterically to ProRS somewhere outside the catalytic pocket, structural analyses of *T. thermophilus* ProRS and other tRNA synthetases provide no support or precedent for this notion (Yaremchuk et al. *J. Mol. Biol.* 309:989-1002 (2001)).

Proline Addition Reverses the Biological Effects of HF

Figure 5A:
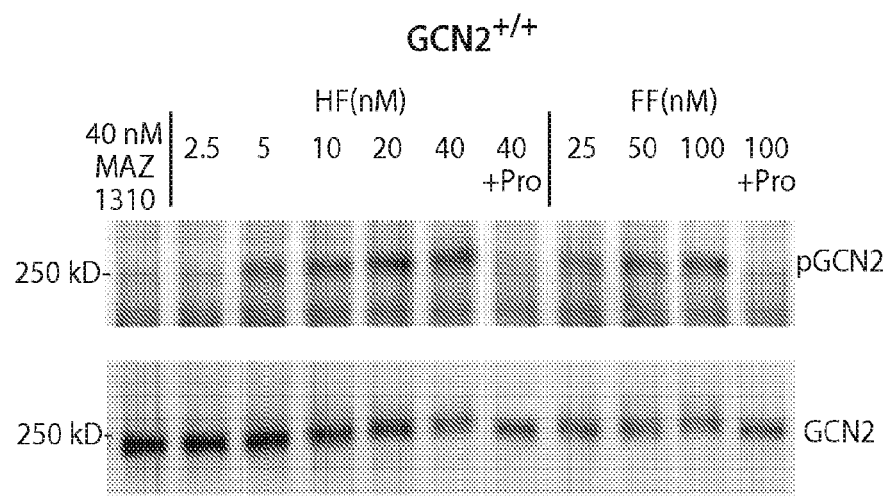
FIG. 5 shows that proline supplementation prevents activation of the amino acid response (AAR) by halofuginone. A) MEFs were treated with the indicated concentration of inhibitor in the presence or absence of 2 mM proline for 2 hours and assayed by Western blot for total GCN2 and GCN2 phosphorylated at Thr898 using a phospho-specific antibody (Cell Signaling). Data are representative of three separate experiments. B) MEFs were treated with 50 nM HF with or without 2 mM proline, lysed 6 hours later and analyzed by Western blot for expression of the AAR response marker CHOP. Cytoplasmic actin (cActin) is shown as a loading control.
Figure 5B:
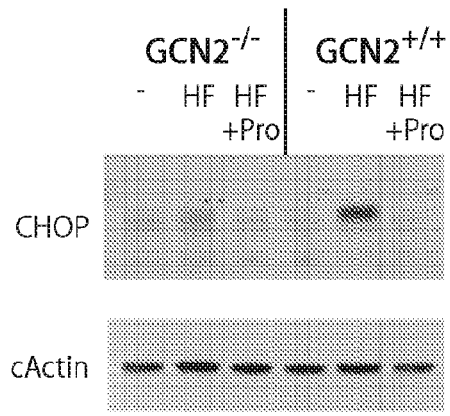
Figure 15:
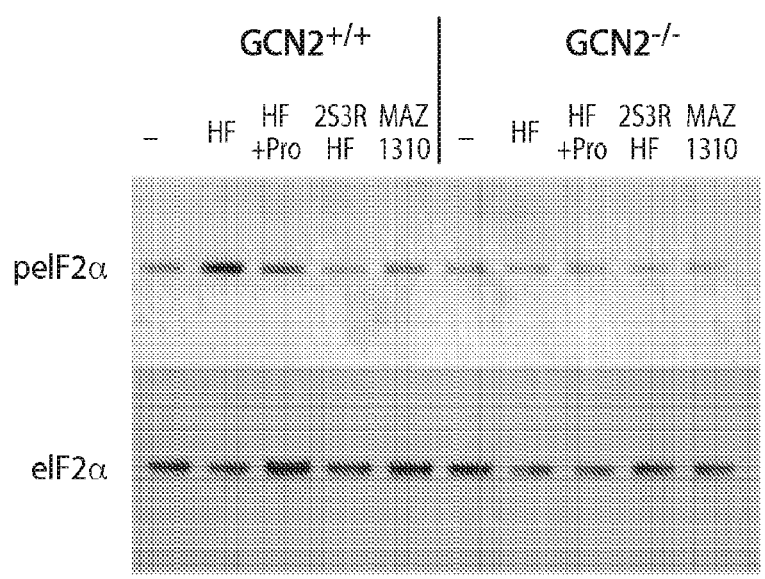
FIG. 15 shows that proline rescues GCN2 dependent induction of eIF2a phosphorylation by halofuginone. eIF2a phosphorylation was stimulated as in FIG. 5A.
Figure 16:
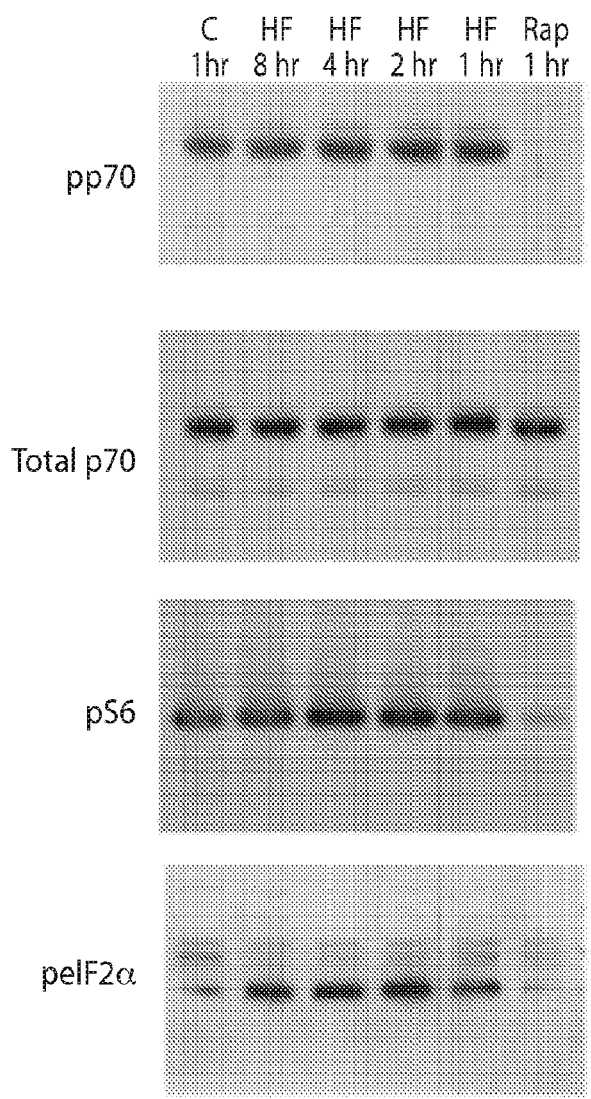
FIG. 16 shows that halofuginone does not directly inhibit downstream targets of the mTORC1 pathway in fibroblasts. MEFs growing in DME/10% FCS were treated with 100 nM HF or 0.5 µM rapamycin and analyzed by Western blot for phosphorylation of component of the mTor signaling pathway.

The ability of proline to rescue the effects of HF on translation in vitro (FIG. 2), and the fact that HF inhibits competitively with respect to proline in the purified enzyme assay (FIG. 3) suggested that proline supplementation in intact cells might specifically reverse the effects of HF. We therefore examined whether proline supplementation antagonized HF-activation of the AAR pathway in intact cells. Consistent with this idea, stimulation of GCN2 phosphorylation by HF/FF in fibroblasts was abrogated by the addition of 2 mM proline (FIG. 5A). Addition of proline also prevented HF-dependent activation of AAR pathway components downstream of GCN2 phosphorylation, including CHOP induction (FIG. 5B) and eIF2a phosphorylation (FIG. 15), indicating that proline utilization is the principal target for HF action in intact cells as it is in rabbit reticulocyte lysates (RRL). As expected, these downstream AAR responses to HF were dramatically reduced in GCN2$^{-/-}$ fibroblasts (FIG. 5B). The mTOR pathway, like the AAR, acts as a cellular sensor for amino acid availability, but, unlike the AAR, mTOR signaling is not blocked by inhibition of tRNA synthetase activity. HF-treatment of T-cells and fibroblasts activates the AAR pathway without concomitant inhibition of mTORC1 signaling (FIG. 16). We conclude that HF is not exerting a direct effect on mTORC1 signaling, consistent with a model in which HF acts to limit tRNA charging rather than altering amino acid levels in intact cells. To exclude the possibility that proline blocks the action of HF by preventing its uptake or accumulation in intact cells, we used an anti-HF antibody in an ELISA assay to directly measure intracellular HF levels in the presence or absence of excess proline. The intracellular accumulation of HF was not affected by proline addition (FIG. 17), supporting our interpretation that proline reverses the effect of HF on AAR activation by enhancing intracellular proline utilization.

Figure 6A:
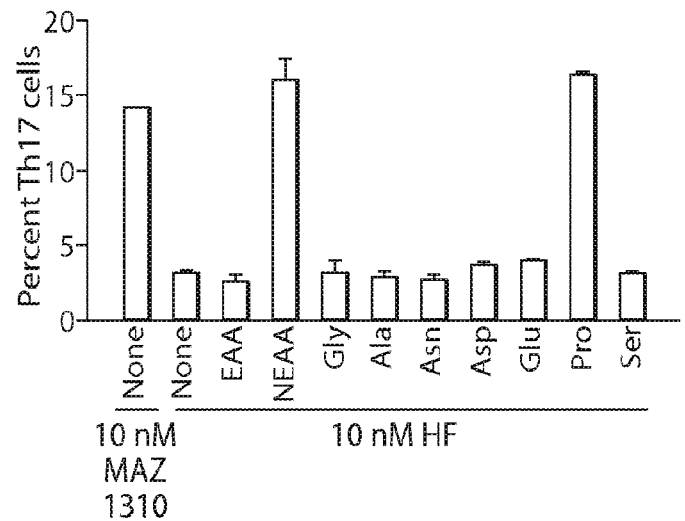
FIG. 6 shows that proline supplementation prevents the biological effects of halofuginone. A) Primary murine $CD4^+$ $CD25^-$ T cells were activated through the T-cell receptor in Th17 polarizing conditions (Sundrud et al. *Science* 324: 1334-8 (2009)) in the presence of either 10 nM MAZ1310 or HF and the following amino acid supplements: 10× concentration of essential (EAA) or non-essential (NEAA) amino acids mixtures (Biowhittaker or Invitrogen, respectively), or 10× concentrations (1 mM) of indicated individual amino acids. Data are presented as mean percentage of Th17 (IL-17+ IFNg−) cells +/−SD from triplicate wells. B) Th17 differentiation was assayed as described above, in the absence or presence of HF or borrelidin, with or without 1 mM threonine or proline supplementation. C) MEFs were treated with or without HF (50 nM) and/or proline (2 mM) for 4 hours (CHOP, S100A4) or 24 hours (ColIA1, ColIA2). mRNA expression was normalized to expression of TBP and is shown relative to untreated control. Error bars reflect standard deviation of triplicate determinations from triplicate plates of cells. Confidence intervals (p-value) for the effect of HF alone versus HF+Pro were determined using a two-tailed Student's t test. Data are representative of two separate experiments. D) Cells were pre-incubated for 24 hours with HF and proline as indicated, and secretion of Type I procollagen was measured after 24 hours in conditioned medium of cells plated by Western blot and quantitated using Image J software (top panel). Total protein synthesis was measured as TCA-precipitable $^{35}$S in a scintillation counter (bottom panel). Error bars reflect standard deviation of triplicate determinations.
Figure 6B:
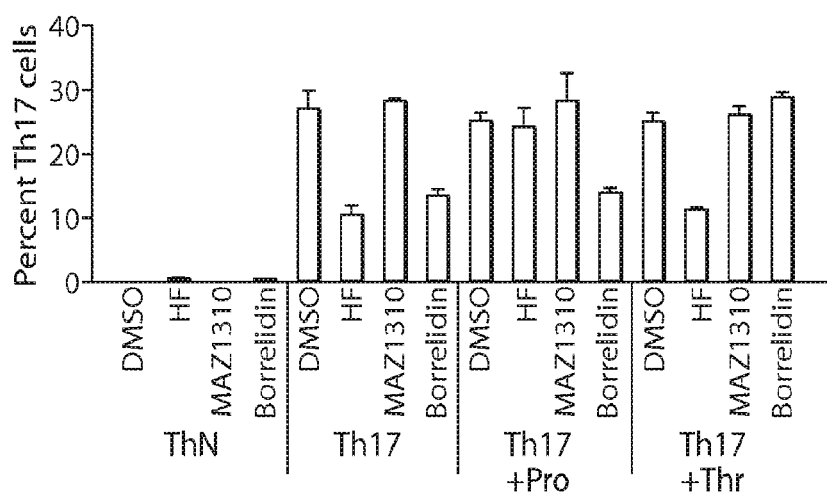
Figure 18:
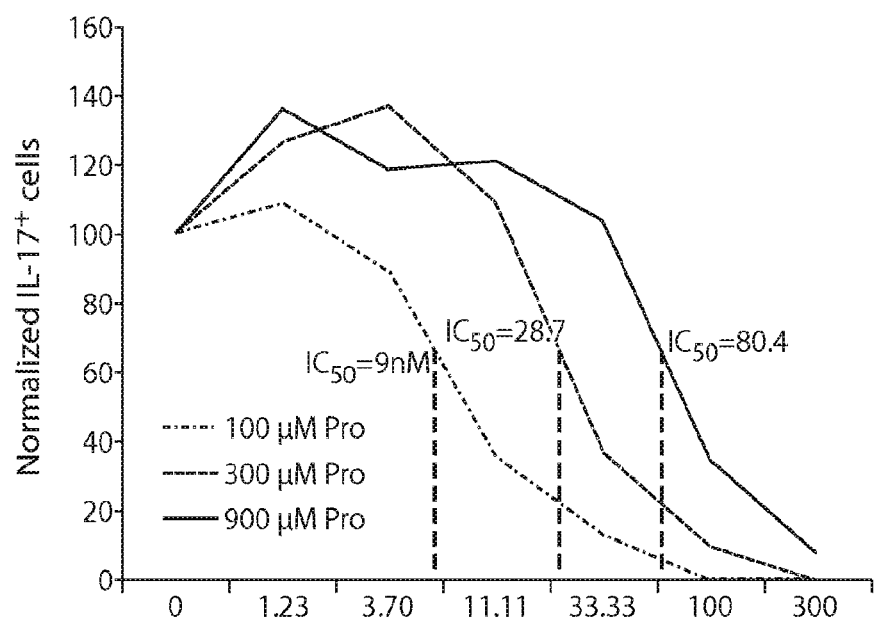
FIG. 18 shows that supplemental proline acts competitively with halofuginone to prevent inhibition of Th17 differentiation. Differentiation of Th17 cells was measured as described for FIG. 6A, with proline supplementation at the doses indicated.
Figure 19:
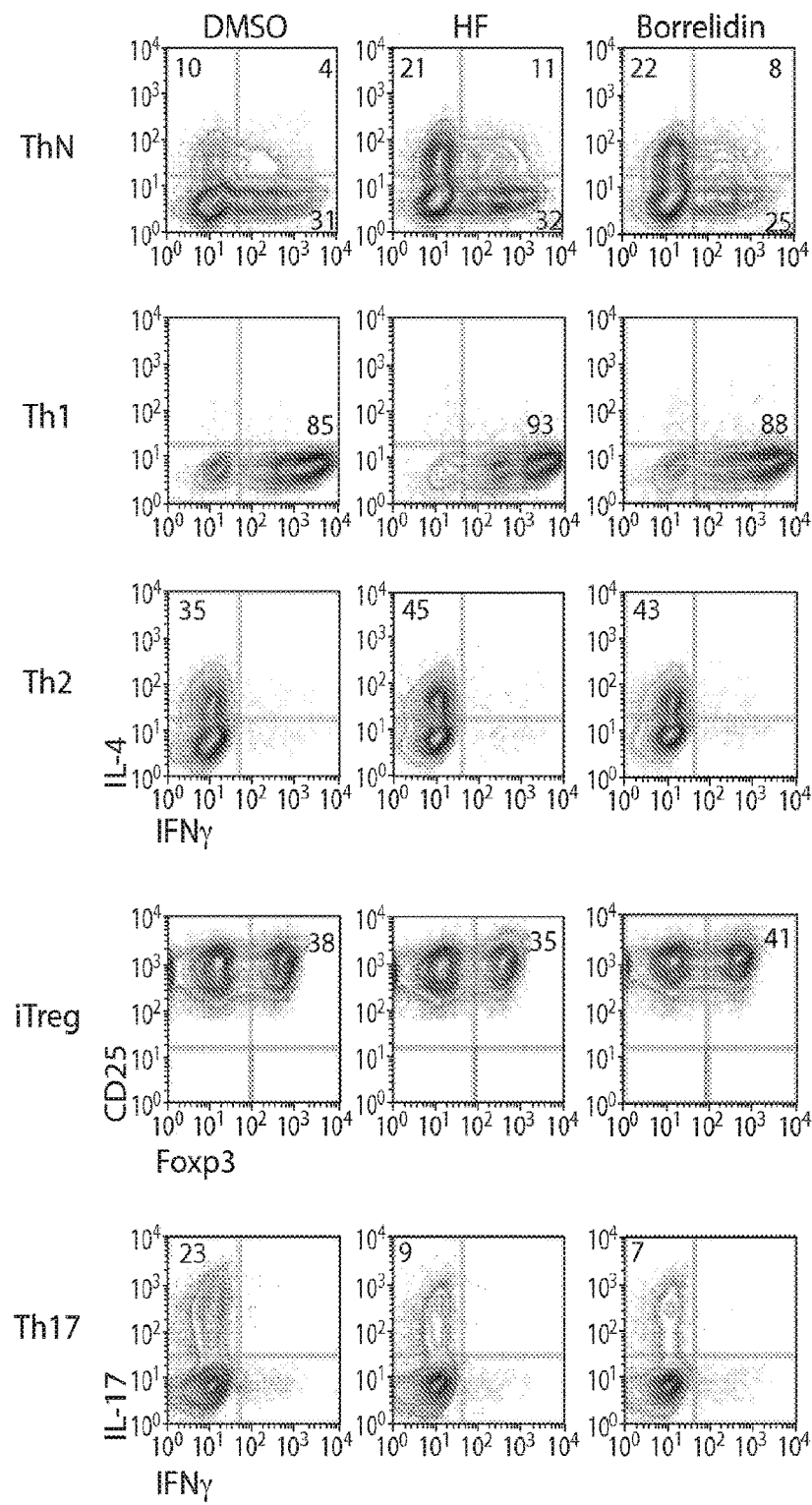
FIG. 19 shows that the threonyl tRNA synthetase inhibitor borrelidin selectively inhibits Th17 differentiation. Primary murine CD4+ CD25− T cells were activated through the TCR in non-polarizing (ThN), or Th17 polarizing conditions and treated with DMSO, 10 nM MAZ1310, 10 nM HF, or 6 nM (3 ng/mL) borrelidin in the presence or absence proline or threonine (0.5 mM). Th17 differentiation was determined as above. Data are presented as mean percentage of Th17 (IL-17+ IFNg−) cells +/−SD from triplicate wells. All data represent 2-3 independent experiments.
Figure 20:
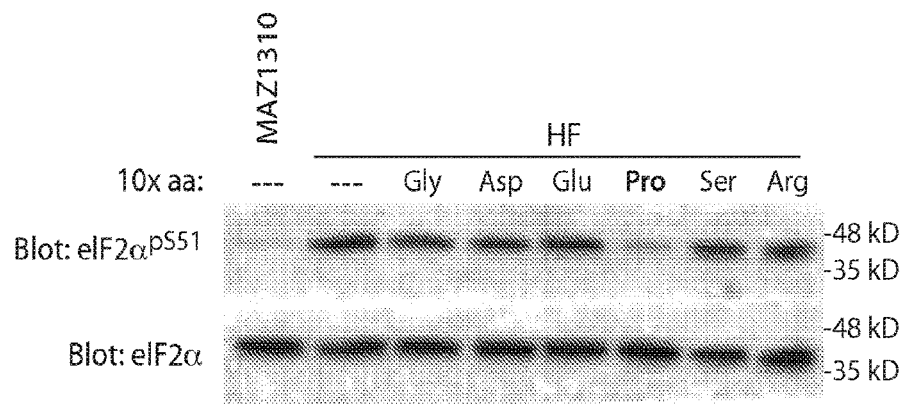
FIG. 20 shows that proline supplementation prevents halofuginone induction of eif2aSer51 phosphorylation in T cells. Primary murine T cells treated as described in FIG. 6 were harvested for Western blot detection of eif2aSer51 phosphorylation.

We previously have shown that HF selectively inhibits Th17 cell differentiation, and that media-supplementation with mixtures of amino acids reverses these effects (Sundrud et al. *Science* 324:1334-8 (2009)). Comparison of the effects of non-essential versus essential amino acid pools established that only non-essential amino acids restore Th17 cell differentiation, or prevent eIF2a phosphorylation in the presence of 10 nM HF (FIG. 6a, FIG. 20). Testing of individual non-essential amino acids established that only proline rescued Th17 differentiation in HF-treated T cells (FIG. 6A). Consistent with the competitive inhibition of proline utilization by HF seen with purified enzyme (FIG. 3), increasing concentration of proline increased the IC$_{50}$ for HF inhibition of TH17 differentiation (FIG. 18) We also tested whether a structurally unrelated tRNA synthetase inhibitor, the threonyl tRNA synthetase inhibitor borrelidin (Ruan et al. *J. Biol. Chem.* 280:571-7 (2005)), could recapitulate the effects of HF on Th17 differentiation. Borrelidin inhibited Th17 cell differentiation with a selectivity identical to that which we have previously reported for HF (Sundrud et al. *Science* 324:1334-8 (2009)) (FIG. 19). Like HF, the effects of borrelidin on Th17 differentiation were reversed by addition of an excess of the cognate amino acid, in this case threonine (FIG. 6B). These results demonstrate that either of two structurally unrelated tRNA synthetase inhibitors exerts a highly selective effect on effector T cell differentiation.

The ability of HF to inhibit tissue remodeling in vivo is evidenced by its potent suppression of tissue fibrosis (Pines et al. Gen. Pharmacol. 30:445-50 (1998); McGaha et al.

Figure 6C:
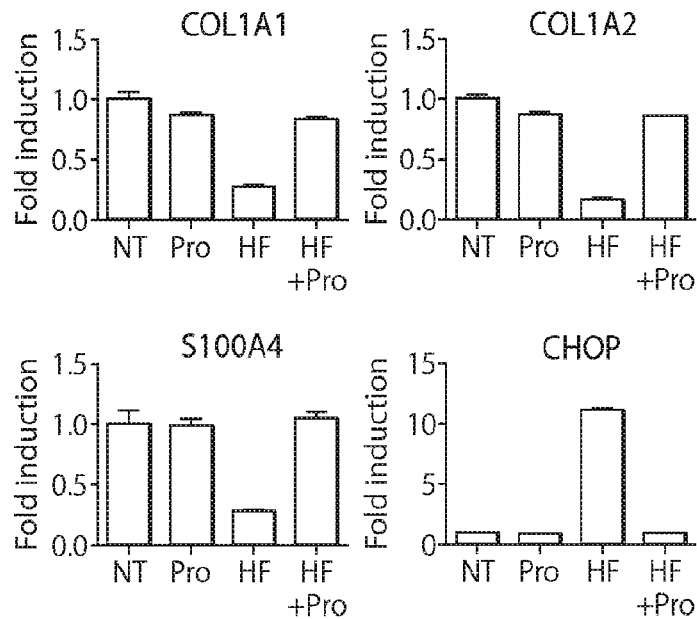
Figure 6D:
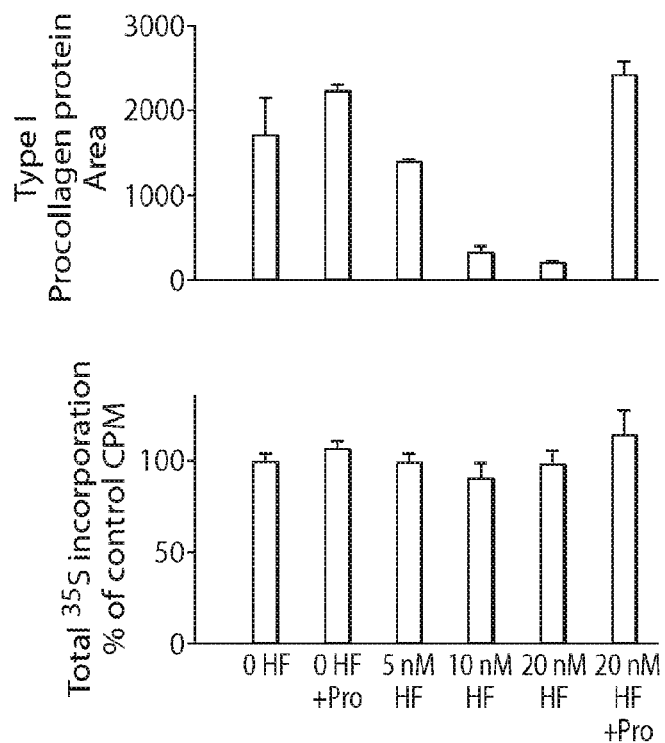
Figure 21:
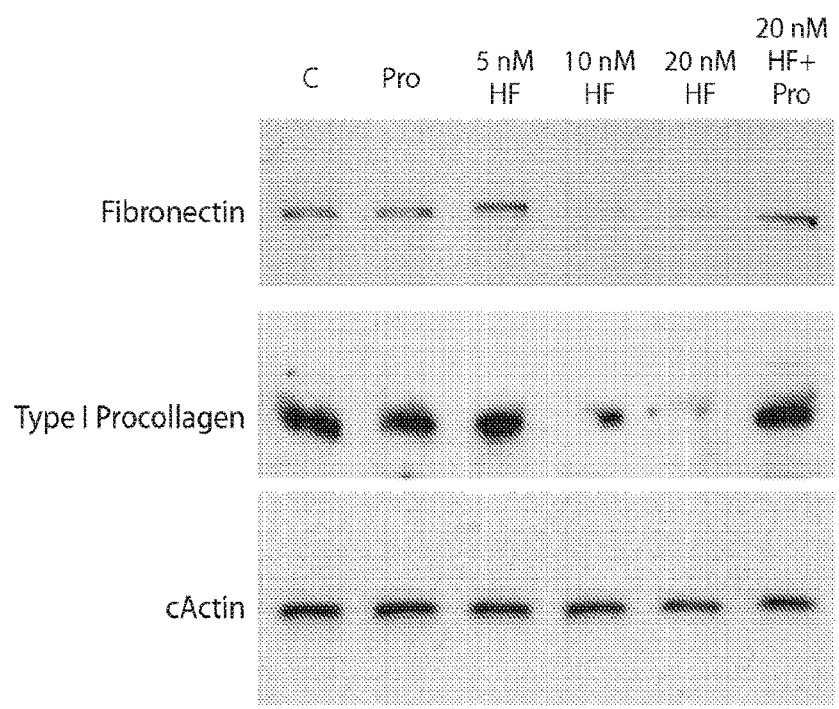
FIG. 21 shows that halofuginone inhibition of Type I procollagen production is reversed by proline. Cells were plated and treated in triplicate with or without HF and proline, and conditioned medium analyzed for Type I procollagen as described in FIG. 6d.

*Autoimmunity* 35:277-82 (2002)) and tumor progression (Elkin et al. *Cancer Res.* 59:4111-8 (1999)). As an antifibrotic agent, HF inhibits the overproduction and deposition of extracellular matrix (ECM) components, such as Type I collagen and fibronectin, both in vivo and in cultured fibroblasts. We found that HF inhibits, and proline supplementation restores, mRNA levels of Col1A1, Col1A2, and S100A4 in mouse embryo fibroblasts (MEFs) (FIG. 6C). S100A4, which is produced and secreted from tumor-activated stromal cells, is implicated in fibrosis and tumor metastasis, as well as in tissue invasion by synoviocytes during rheumatoid arthritis (Boye et al. *Am. J. Pathol.* 176:528-35 (2009); Oslejskova et al. *Rheumatology (Oxford)* 48:1590-4 (2009)). Expression of mRNA encoding the AAR-responsive factor CHOP was stimulated by HF, concomitant with inhibition of the expression of ECM genes. Consistent with prior reports (Pines et al. *Gen. Pharmacol.* 30:445-50 (1998); McGaha et al. *Autoimmunity* 35:277-82 (2002)), HF-treatment of cells for 24 hours dramatically inhibited the production of secreted Type I procollagen and the production of fibronectin, at doses that did not significantly change $^{35}$S-methionine incorporation into total protein, (FIG. 6D). HF-mediated inhibition of these ECM proteins, like the HF-induced modulation of gene transcription, was reversed by the addition of 2 mM proline to the media (FIG. 21).

Figures 22, 23:
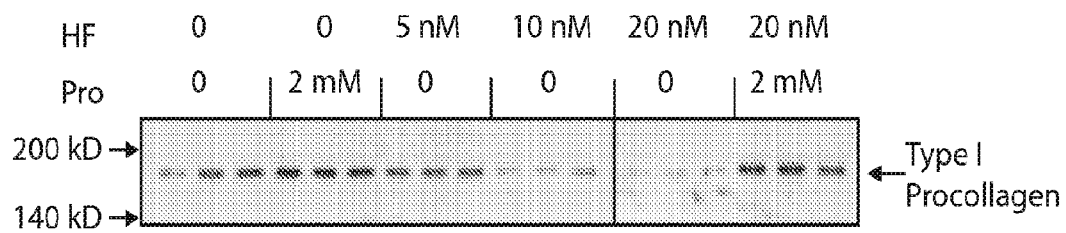
FIG. 22 shows that proline rescues HF-suppression of ECM protein production. Shown is the blot used for the quantitation presented in FIG. 6D. MEFs were incubated for 4 hours in HF with or without 2 mM proline, to measure new collagen production in conditioned medium. Cells were washed into fresh DMEM/0.2% FBS, and proline or HF re-added, and either conditioned medium (for Type I procollagen) or total cell lysate (for fibronectin, c-actin) and were harvested after 24 hours. Triplicate plates of cells for each condition were treated, harvested, and blotted in parallel. Protein levels were assayed by Western blot, detected using chemiluminescence, and film exposure was quantitated using Image J software.
FIG. 23 shows that proline reverses anti-malarial effects of HF but not of the structurally unrelated anti-malarial amodiaquine. The activity of halofuginone and amodiaquine as inhibitors of *P. falciparum* growth was tested in erythrocytes in RPMI with or without excess amino acids as indicated, and IC$_{50}$ values were normalized to IC$_{50}$ values obtained under standard conditions using unmodified RPMI (numbers in bold). The absolute IC$_{50}$ values for halofuginone and amodiaquine for RPMI are reported in parentheses. Fold amino acid indicated (e.g., "5×") is relative to the concentration of the respective amino acid in RPMI. Fold concentration of D-Pro and L-Orn are relative to L-Pro.

In addition to the proline rescue of HF-mediated effects on AAR pathway activation, HF-mediated inhibition of Th17 cell differentiation, and HF-mediated antifibrotic effects, HF-inhibition of *P. falciparum* growth in red blood cells is reversed by the addition of proline. The addition of 5× proline to the amino acid containing media of red blood cells that are infected with the Dd2 strain of *P. falciparum* increased the effective $IC_{50}$ of HF and febrifugine by roughly 7 and 5-fold, respectively, but did not affect the $IC_{50}$ of an unrelated antimalarial amodiaquine (FIG. 23). Whereas further work is necessary to establish whether HF acts by targeting *P. falciparum* prolyl-tRNA synthetase activity, these data indicate that HF does act specifically on the utilization of proline during *P. falciparum* growth and indicates that this activity accounts for the antimalarial effects of HF.

Halofuginol and Halofuginone Inhibit Type I Collagen Expression in Fibroblasts in Culture Primary human prostate stromal (hPrSc) cells were left in low-serum media (0.2%) for 24 hours, and treated consecutively twice for 48 hours, halofuginone (HF) or halofuginol (HFol) at the concentrations indicated. Relative mRNA levels of the myofibroblastic markeralpha 1 collagen type 1 (col1a1) was measured by quantitative real-time PCR using glyceraldehyde-3-phosphate dehydrogenase (GAPDH) as internal control.

Halofuginol and Halofuginone Inhibit Expression of the Activated Fibroblast Marker S100A4

Primary human prostate stromal (hPrSc) cells were left in low-serum media (0.2%) for 24 hours, and treated consecutively twice for 48 hours with or without tumor-growth factor beta (TGF; 10 ng/ml), halofuginone (HF) or halofuginol (HFol) at the concentrations indicated. Relative mRNA levels of the fibrosis/tissue invasion marker s100a4 was measured by quantitative real-time PCR using glyceraldehyde-3-phosphate dehydrogenase (GAPDH) as internal control.

We have shown that febrifugine-family compounds act competitively with proline as potent inhibitors of the tRNA charging activity of EPRS, and we propose that this constitutes a single primary mechanism for their reported biological activities. Although EPRS is an essential component of the protein synthetic-machinery, HF-inhibition of prolyl-tRNA charging evokes a highly specific cluster of biological effects, at doses that do not have a global effect on protein synthesis. These observations are consistent with HF-activation of a metabolic sensor, in this case AAR pathway activation, rather than with an HF-mediated blockade of proline incorporation into cellular protein. In fibroblasts, for example, HF enhances expression of the AAR protein CHOP, while selectively inhibiting production of ECM proteins—fibronectin, which is not rich in proline, as well as proline-rich collagen. Systematic analysis of mRNA-specific translational regulation during cytoprotective responses to different stresses will be essential to understand how stress pathway activation yields specific biological responses. It is significant to note that even though GCN2 phosphorylation is a hallmark of AAR signaling and constitutes the known signal transducer of the canonical AAR pathway, cells lacking GCN2 nonetheless respond to amino acid limitation by making specific changes in gene expression and mRNA splicing (FIG. 7) (Pleiss et al. *Mol. Cell.* 27:928-37 (2007); Deval et al. *FEBS J.* 276:707-18 (2009)). These observations clearly indicate that cellular amino acid restriction or the chemical inhibition of tRNA charging can activate a metabolic sensor pathway, which includes primary components that have yet to be described.

A component of halofuginone's therapeutic impact stems from activation of the AAR pathway, but whether or not any of the observed effects of HF can be attributed to EPRS-induced changes that are unique to proline metabolism, or to non-canonical activities of EPRS are interesting open questions. In particular, EPRS has been shown to participate in the interferon-γ-activated inhibitor of translation (GAIT) complex, in myeloid cells, to suppress expression of a posttranscriptional regulon of proinflammatory genes (Mukhopadhyay et al. *Trends Biochem. Sci.* 34:324-31 (2009)).

HF and its family members act as proline restriction mimetics, by binding to EPRS and blocking prolyl-tRNA charging. In doing so, they act as molecular probes that highlight the AAR pathway's contribution to the potent, but unexplained, cellular and organismal benefits of caloric and nutrient restriction. Dietary restriction (DR) with adequate nutrition is the most robust intervention known for the systemic prevention of age-related diseases in animals and extension of lifespan across species (Fontana et al. *Science* 328:321-6 (2010); Anderson et al. *Trends Endocrinol. Metab.* 21:134-41 (2009); Haigis et al. *Mol. Cell* 40:333-44 (2010)). Amino acid restriction is a subset of DR, but many of the cellular changes that correlate with tissue and organism longevity can be reproduced by amino acid limitation alone (Caro et al. *Biogerontology* 10:579-92 (2009); Xiao et al. *Diabetes* (2011)). DR has numerous benefits for the aging organism, which include a reduction of inflammation and oxidative stress. Inflammation is a common denominator in age-associated pathologies, such as metabolic syndrome, cardiovascular disease, cancer, and insulin resistant diabetes (Fontana et al. *Science* 328:321-6 (2010)). Dietary restriction of amino acids alone has been shown to increase insulin sensitivity in mice (Xiao et al. *Diabetes* (2011)). The molecular basis for DR's healthspan-increasing benefits is poorly understood, but metabolic sensor pathways that trigger organismal adaptation to diminished nutrient supply are central to this process (Anderson et al. *Trends Endocrinol. Metab.* 21:134-41 (2009); Haigis et al. *Mol. Cell* 40:333-44 (2010)). We show here that, in the absence of true nutritional deficit, febrifugine-derived compounds block EPRS activity to send intracellular signals indicative of proline limitation, activating the AAR pathway and thereby reproducing a key component of the beneficial effects of caloric restriction.

Changes in the level of intracellular amino acids and the signaling pathways that detect these changes have an emergent role in the maintenance of immune and tissue homeostasis (Powell et al. *Immunity* 33:301-11 (2010); Cobbold et al. *Proc. Natl. Acad. Sci. USA* 106:12055-60 (2009)). Amino acid levels have been shown to regulate the inflammatory vs. tolerogenic state of cellular populations that are key to this process, in cell types such as plasmacytoid dendritic cells (pDC's), polymorphonuclear leukocytes (PMN) (Zelante et al. *Eur. J. Immunol.* 37:2695-706 (2007)), and macrophages (Huang et al. *Int. Rev. Immunol.* 29:133-55 (2010); von Bubnoff et al. *J. Am. Acad. Dermatol.* (2011)). Amino acid-degrading enzymes such as arginase and indoleamine 2,3 dioxygenase (IDO) that catabolize L-arginine and L-tryptophan, respectively, exemplify metabolic sensor pathway adaptation for cellular regulation of the inflammatory/tolerogenic phenotype (Bronte et al. *Nat. Rev. Immunol.* 5:641-54 (2005)). Amino acid-degradation has two functional outputs—the production or destruction of immunologically active amino acid metabolites, and the detectable nutrient limitation produced by amino acid-catabolism accompanied by a metabolic stress pathway response. In the case of L-arginine, which is itself a substrate for nitric oxide synthase (NOS), arginine degradation both depletes the substrate pool for pro-inflammatory nitric oxide (NO) and activates the AAR pathway (Hotamisligil et al. *Nat. Rev. Immunol.* 8:923-34 (2008)). It is now recognized that microorganisms can exploit this pathway to enhance their survival. Pathogens upregulate their arginases to deplete host arginine pools, suppressing the host innate immune response and inhibiting T cell proliferation (Grohmann et al. *Immunol Rev.* 236:243-64 (2010)). The immunosuppressive enzyme IDO plays a complex regulatory role in a number of physiological and pathophysiological settings that include maternal-fetal tolerance, infection, allergy, autoimmune disease, and transplantation by mediating tryptophan catabolism. Several immunoregulatory cells populations utilize the induction of IDO expression to activate anti-inflammatory or tolerogenic programs (Grohmann et al. *Immunol Rev.* 236: 243-64 (2010)). IDO-expressing pDCs inhibit effector T cell responses, activate Tregs, and can attenuate pro-inflammatory responses that manifest in chronic disease syndromes (Hotamisligil et al. *Nat. Rev. Immunol.* 8:923-34 (2008)). Critical mediators of peripheral tolerance, Tregs have been shown to induce the expression of enzymes that degrade at least five different amino acids in skin grafts and in DCs. Inhibition of the mTOR pathway consequent to amino acid limitation reinforced the tolerogenic signaling loop by induction of the Treg-specific transcription factor forkhead box P3 (FoxP3) (Cobbold et al. *Proc. Natl. Acad. Sci. USA* 106:12055-60 (2009)). To the emerging story of the adaptation of intracellular amino acid regulation for immune homeostasis, we recently added the observation that differentiation of pro-inflammatory Th17 cells is potently inhibited by activation of the AAR pathway (Sundrud et al. *Science* 324:1334-8 (2009)). We now show that HF suppresses pathologic inflammation by its action as a primary inhibitor of EPRS and an amino acid-restriction mimetic. These observations provide an additional example of a natural product therapeutic that acts by leveraging a metabolic stress response, in this case the amino acid response (AAR), for modulation of immune and inflammatory responses.

The therapeutic application of amino acid restriction-mimetics to a disease tissue environment provides a novel means of reprogramming key immunoregulatory cells to a tolerogenic/anti-inflammatory phenotype. Here we show that HF inhibits the prolyl-tRNA synthetase activity of EPRS and thereby activates the AAR to elicit antimicrobial and immunoregulatory responses in tissues. In light of the prominent role of inflammatory disease in age-related pathologies, amino acid-restriction mimetics may provide vital molecular probes for the study of health- and lifespan extension in humans. Our new understanding of the molecular mechanism of action of febrifugine and its derivatives, combined with the ability of these compounds to selectively inhibit Th17 cell differentiation in vivo, makes possible the design of a new family of therapeutic compounds with improved pharmacological properties for the treatment of a variety of serious illnesses, including multiple sclerosis, scleroderma, and rheumatoid arthritis.

In Vitro Translation Assays

Effects of HF, HF derivatives, and added amino acids on cell free protein translation were assayed in rabbit reticulocyte lysate (RRL) according to the manufacturer's instructions (Promega), with the exception that the standard amino acid mix provided was diluted 5-fold for assays. In some experiments RRL was preincubated at 30 degrees with another RNA (hALK4) to deplete endogenous charged tRNAs. Luciferase activity was measured using a luciferase assay kit (Promega). To assay tRNA charging in RRL, 25 μl RRL was incubated with 1 μCi $^{14}$C Pro or $^{35}$S Met, 1 μg added bovine tRNA, and 2 μM puromycin (to prevent utilization of charged tRNAs for protein translation). After 20 minutes, total tRNA was extracted using a miRVANA small RNA isolation kit (Ambion), and incorporated radioactivity measured in a scintillation counter.

siRNA Knockdowns

For knockdown of EPRS, human lung fibroblast cells (IMR90) were transfected with siRNAs against EPRS and control (ON-TARGETplus SMART pool L-008245-00-0005 for human EPRS and ON-TARGETplus non-targeting Pool D-001810-10-05 as control; Thermo Scientific) using Lipofectamine RNAiMAX according to the manufacturer's instructions (Invitrogen). For qPCR experiments, cells were left for 2 hours in serum-free media and then treated with HF for 6 hours in serum-free media, before harvesting RNA with Trizol gene expression quantitated by quantitative RT-PCR using the Roche UPR Light-Cycler system. For Western blot experiments, cells were left 2 hours in media without serum and treated with HF for another 2 hours (in serum-free media) before harvesting the protein lysates with RIPA buffer plus protease and phosphatase inhibitors.

Assay of ProRS Activity

The prolyl tRNA synthetase domain of human EPRS (ProRS) was expressed in *E. coli* with a 6-His tag and purified as described (Heacock et al. *Bioorganic Chemistry* 24 (1996)). Purified enzyme was visualized as a single band by Laemmli gel electrophoresis/Coomassie staining. Enzymatic activity was assayed using incorporation of $^3$H Pro into the tRNA fraction essentially as described (Ting et al. *J. Biol. Chem.* 267:17701-9 (1992)), except that the charged tRNA fraction was isolated by rapid batchwise binding to Mono Q sepharose (Jahn et al. *Nucleic Acids Res.* 19:2786 (1991)) (GE Healthcare) and quantitated by liquid scintillation counting. In preliminary experiments, the assay was established to be linear over the time (6 min) and conditions used (30 degrees, 2 mM ATP, 1 μg/μl total tRNA purified from rabbit liver). For all kinetic assays, the concentration of active enzyme in the reaction (determined by inhibitor titration as described in Copeland) was 40 nM. Similar inhibition by HF was seen using the human ProRS domain purified from bacteria and full length EPRS purified from rat liver (Ting et al. *J. Biol. Chem.* 267:17701-9 (1992)).

Assay of HF Binding to ProRS

To examine HF binding to ProRS, $^3$H HFol was synthesized by American Radiochemicals (St. Louis) by reduction of MAZ1310 (3) at the ketone with NaB$^3$H$_4$, followed by removal of the Boc protecting group with 10% trifluoroacetic acid in dichloromethane, and HPLC purification of the $^3$H HFol. 100 nM $^3$H HFol was incubated with ProRS immobilized on Ni-NTA beads (Pierce) in 50 mM Tris pH 7.5, 5 mM MgCl$_2$, 20 mM Imidazole, 1 mM DTT, 10% glycerol, and nucleotides, proline, or HF derivatives at room temperature for 10 minutes as indicated. After incubation, beads were washed twice with ice-cold wash buffer (50 mM Tris 7.5; 20 mM Imidazole; 1 mM DTT, 20% glycerol). $^3$H HFol bound after washing was measured by liquid scintillation counting. Ni-NTA beads incubated with *E. coli* extracts lacking tagged ProRS were used as a background reference in all experiments.

Proline Rescue of HF in T Cells

To study proline rescue of HF effects in T-cells, primary murine CD4+ CD25− T cells were isolated from spleens and peripheral lymph nodes of wild-type C57B/6 mice (Jackson laboratories), and T cell activation, differentiation, treatment with HF, and amino acid supplementation was performed as described (Sundrud et al. *Science* 324:1334-8 (2009)). In some experiments, T cell cultures were supplemented with excess individual amino acids as described above and previously (Sundrud et al. *Science* 324:1334-8 (2009)). All FACS data was acquired on a FACSCalibur flow cytometer (BD Pharmingen) and analyzed using FlowJo software (Treestar, Inc.). Protocols and antibodies used for FACS staining of T cells have been described previously (Sundrud et al. *Science* 324:1334-8 (2009)). Briefly, Th17 differentiation (percentage of IL-17+ IFNg− cells) was determined on day 4-cultured T cells following restimulation with phorbol myristate acetate (PMA; 10 nM) and ionomycin (1 mM), in the presence of brefeldin A (10 mg/ml) for 4-5 hours. Cytokine expression in restimulated cells was determined by intracellular cytokine staining as described (Sundrud et al. *Science* 324:1334-8 (2009)). In some experiments cytokine production by cells activated in non-polarizing conditions (ThN), Th1, or Th2 conditions was determined on day 5 following restimulation and intracellular cytokine staining as above. Inducible T regulatory (iTreg) differentiation was assessed by CD25 and Foxp3 upregulation on day 3-post activation using a commercially available Foxp3 intracellular staining kit (eBioscience).

Proline Rescue of HF in Primary Fibroblasts

For assays of HF and proline effects on fibroblasts, mouse embryo fibroblasts were grown in 10% FCS/DMEM. For studies of TGFβ signaling, $^{35}$S methionine incorporation into total protein, and collagen production, cells were shifted into 0.2% FCS/DMEM 24 hours before the addition of HF or proline. For examination of protein expression and phosphorylation, cells were lysed in RIPA with 5 mM EDTA, 1× PhosStop (Roche), and 1× Complete protease inhibitor mix (Roche), and assayed by Western blot as described above. For analysis of gene expression, cells were lysed in Trizol (Invitrogen) and gene expression quantitated by quantitative RT-PCR using the Roche UPR Light-Cycler system.

Protein Sequence of Propep and NoPropep Polypeptides:

```
Myc-Propep:
                                          (SEQ ID NO: 1)
MEQKLISEEDLNEMEQKLISEEDLNEMEQKLISEEDLNEMEQKLISEEDL
NEMEQKLISEEDLNEMESLGDLTMEQKLISEEDLNSSSQSLYRGAFVYDC
SPPKFKASRASRTIVSRIT Myc-NoPropep:
                                          (SEQ ID NO: 2)
MEQKLISEEDLNEMEQKLISEEDLNEMEQKLISEEDLNEMEQKLISEEDL
NEMEQKLISEEDLNEMESLGDLTMEQKLISEEDLNSSSQSLYRGAFVYDC
SKFKASRASRTIVSRIT ON-TARGETplus SMART pool L-008245-00-0005 for
human EPRS NM_004446, 5 nM:
ON-TARGETplus SMARTpool siRNA J-008245-05, EPRS
                                          (SEQ ID NO: 3)
Target sequence: GAAGUUGGGCCACGUGAUA ON-TARGETplus SMARTpool siRNA J-008245-06, EPRS
                                          (SEQ ID NO: 4)
Target sequence: GAAUAUAGUCGGCUAAAUC ON-TARGETplus SMARTpool siRNA J-008245-07, EPRS
                                          (SEQ ID NO: 5)
Target sequence: GGUGAGAUGGUUACAUUUA ON-TARGETplus SMART siRNA J-008245-08, EPRS
                                          (SEQ ID NO: 6)
Target sequence: UCAAGUAGAUAUAGCUGUU
```

Purification of Human ProRS Expressed in *E. coli*

6-His-tagged human ProRS (pKS509 from Dr. K. Musier-Forsyth) was expressed in BL21(DE3) strain and purified as previously described with modification (Heacock et al. *Bioorganic Chemistry* 24 (1996)). Extracts of cells expressing empty vector (pET-19b) were used as control. Briefly, cell pellets were resuspended (50 µl/1 ml bacterial culture) in an ice-cold lysis buffer (100 mM KH$_2$PO$_4$ (pH 7.8), 300 mM NaCl, 2 mM β-ME, 1 mM PMSF, 1× Complete protease inhibitor cocktail (EDTA) (Roche Applied Science)). Cells were lysed by sonication. After centrifugation, supernatants were incubated with ⅕ volume of lysis buffer-equilibrated, 50% HIsPur Ni-NTA resin slurry (Thermo Scientific) for 1-4 hrs. Beads were washed several times with an ice-cold wash buffer (100 mM KH$_2$PO$_4$ (pH 6.0), 300 mM NaCl, 2 mM β-ME, 10% glycerol) followed by several washes with the wash buffer supplemented with 200 mM imidazole. For purification of ProRS, proteins were eluted with the wash buffer supplemented with 500 mM imidazole. Eluates were supplemented with glycerol to 50% and stored at −20° C. For preparation of immobilized ProRS, beads were washed several times with an ice-cold equilibration buffer [HEPES (pH 7.5), 2 mM β-ME, 10% glycerol] followed by several washes with an ice-cold storage buffer [HEPES (pH 7.5), 2 mM β-ME, 50% glycerol]. Beads were stored as 50% slurry in the storage buffer at −20° C. Concentration of active enzyme was determined by inhibitor titration as described in Copeland (Copeland *Methods Biochem. Anal.* 46:1-265 (2005)), see FIG. 10.

siRNA Depletion of EPRS

For knockdown of EPRS, human lung fibroblast cells (IMR90) were transfected with siRNAs against EPRS and control (ON-TARGETplus SMART pool L-008245-00-0005 for human EPRS and ON-TARGETplus non-targeting Pool D-001810-10-05 as control; Thermo scientific) using Lipofectamine RNAiMAX according to the manufacturer's instructions (Invitrogen). Briefly, 6 pmol of siRNAs were diluted in 100 µl of Opti-MEM I Medium without serum in each well of a 24 well plate and mixed gently. Lipofectamine RNAiMAX (1 µl) was added to each well, mixed gently and incubated 15 minutes at room temperature. Cells (12500 cells/well of a 24 well plate) were diluted in 500 µl of growth medium without antibiotics to give a 30-50% confluency 24 hours after plating. 500 µl of the diluted cells were added to each well with the siRNA-Lipofectamine RNAiMAX complexes and mixed gently by rocking the plate back and forth. Media was changed 24 hours post-transfection and cells were left for 48 hours in media with antibiotics (with serum).

tRNA-Pro Isolation Using Mono Q Beads

For the rapid, quantitative isolation of aminoacylated tRNA$^{pro}$ from synthetase reaction mixtures, reactions were stopped with 100 µl of ice cold 20 mM MOPS pH6.2, 200 mM NaCl, 10 mM EDTA, 30% Glycerol and placed on ice. Samples were added to 15 µl of packed Mono Q HP beads (GE Healthcare) equilibrated in the same buffer. Samples were incubated with beads on ice for 10 min, beads were pelleted by 5 sec centrifugation in a tabletop microfuge and washed 3× 1 ml of wash buffer (20 mM MOPS pH6.2, 50 mM NaCl), and recovered pellets counted in a liquid scintillation counter. Background binding of $^3$H Pro to beads (using reaction mix with either no enzyme added or no tRNA added) was negligible (20-40 cpm).

Primers and Probes for Q-PCR

Q-PCR was performed using the Roche LightCycle UPR system, using the following primers and probes:

```
Col1A 1: probe 15
                              (SEQ ID NO: 7)
primer 1: catgttcagctttgtggacct
                              (SEQ ID NO: 8)
primer 2: gcagctgacttcagggatgt Col1A2: probe 46
                              (SEQ ID NO: 9)
primer 1: gcaggttcacctactctgtcct
                              (SEQ ID NO: 10)
primer 2: cttgcccattcatttgtct S100A4: probe 56
                              (SEQ ID NO: 11)
primer 1: ggagctgcctagcttcctg
                              (SEQ ID NO: 12)
primer 2: tcctggaagtcaacttcattgtc CHOP: probe 21
                              (SEQ ID NO: 13)
primer 1: gcgacagagccagaataaca
                              (SEQ ID NO: 14)
primer 2: gatgcacttccttctggaaca TBP: probe 107
                              (SEQ ID NO: 15)
primer 1: ggcggtttggctaggttt
                              (SEQ ID NO: 16)
primer 2: gggttatcttcacacaccatga Tubb5: probe 16
                              (SEQ ID NO: 17)
primer 1: ctgagtaccagcagtaccaggat
                              (SEQ ID NO: 18)
primer 2: ctctctgccttaggcctcct
```

Probe and primers were designed using the ProbeFinder software (https://www.roche-applied-science.com/sis/rtpcr/upl/index.jsp?id=uplct_030000).

Anti-HF ELISA

Figure 17:
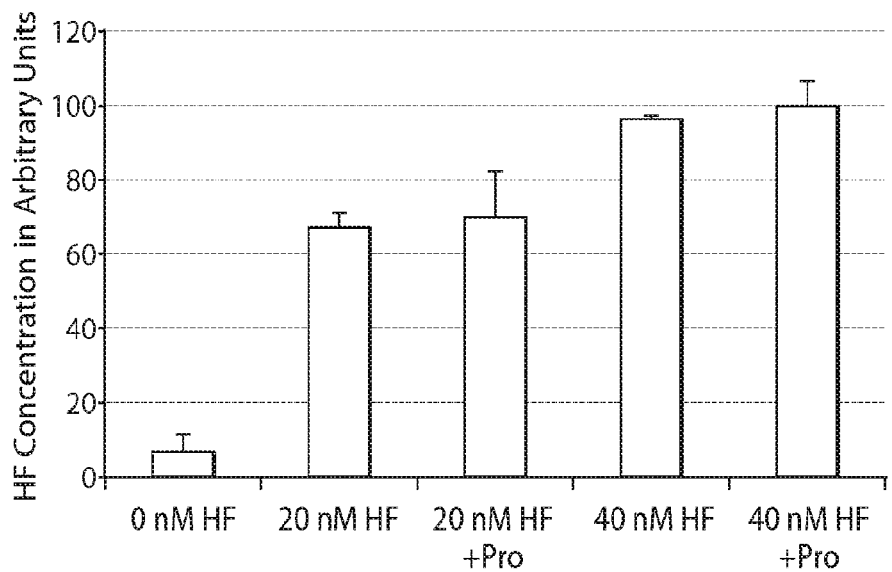
FIG. 17 shows that incubation with proline does not change intracellular accumulation of halofuginone. MEFs were incubated with the indicated concentration of HF in the presence or absence of 2 mM proline for 2 hours, washed twice in cold PBS, and lysed in 1% NP40. Lysates were then tested for HF levels in comparison to a standard curve using known concentrations of HF with an anti-HF antibody based ELISA assay (see Examples). Error bars reflect standard deviation of triplicate determinations. Similar results were obtained in three separate experiments.

Polyclonal anti-HF antibody was raised by immunizing rabbits with KLH coupled to an HF derivative (MAZ1356, FIG. 1) containing a linker attached to the quinazolinone and terminated by a primary amino group. Antibody was affinity purified using MAZ1356 linked to NHS-agarose. For the ELISA assay (FIG. 17), MAZ1356 was coupled to 96-well Reacti-bind Plates (Pierce). After binding, plates were blocked with 10% goat serum in PBS/0.2% Tween-20 (PBST). In preliminary experiments, a range of concentrations of MAZ1356 coupling and anti-HF antibody were tested to determine concentrations that yielded optimally sensitive and linear detection of HF in the 10-100 nM range. To establish a standard curve for HF concentration, MAZ1356-bound plates were incubated with affinity purified anti-HF antibody in 10% goat serum/PBST for 2 hours at room temperature in the presence of known concentrations of HF, then washed 5 times with PBST and incubated with Goat anti-rabbit HRP in 10% goat serum/PBST. Captured antibody was quantitated using TMB based colorimetric detection (Pierce), and a standard curve for HF concentration fitted from the colorimetric data. To assay HF concentration in cells, mouse embryo fibroblasts were incubated with indicated concentrations of HF for 2 hours, and lysed in 200 µl 1% NP40 buffer. Total protein was precipitated by incubation with 0.1 M acetic acid and centrifugation for 10 min. Cleared lysates were neutralized with Tris pH 7.5. To determine HF concentration in cells, 8 µl of cleared lysate (or control buffer) was incubated with anti-HF antibody in MAZ1356 bound wells, and captured antibody detected and quantitated as described above. HF concentration was then determined by fitting colorimetry results with cell samples to a standard curve of HF concentration. Data in FIG. 17 are plotted as "arbitrary units" because the precise intracellular volume of the cells lysed is not known, and therefore the absolute concentration of HF in cells can only be estimated. Estimating the total packed cell volume of $5\times10^5$ mouse embryo fibroblasts as 4 µl (Pierce NE-PER kit) yields an absolute value of ~800 nM HF inside cells that have been incubated with 20 nM HF. These data suggest that there is substantial concentration of HF from the medium, although since the sub-cellular distribution of HF is not known, the effective concentration in the cytosol cannot be reliably estimated.

In Vitro *P. falciparum* Viability Assay

In vitro potency against *P. falciparum* (DD2) was assessed using a modified version of the method of Plouffe and coworkers (Plouffe et al. *Proc. Natl. Acad. Sci. USA* 105: 9059-64 (2008)). Parasites were cultured in the presence of drug in RPMI (Sigma) containing 4.16 mg/ml Albumax in a total volume of 50 µl at a 2.5% hematocrit and an initial parasitemia of 0.3% in black Greiner GNF clear-bottom plates. Cultures were incubated 72 hr at 37° C. under 95% $N_2$, 4% $CO_2$ and 3% $O_2$. At the end of the incubation, SYBR green was added to a dilution of 1:10,000 and plates were stored overnight (or until ready to be read) at −80° C. Just before reading, plates were centrifuged at 700 rpm and fluorescence was read using 480 nm excitation and 530 nm emission frequencies. Compound concentrations that inhibit parasite replication reduce the fluorescence intensity of SYBR green bound to parasite DNA.

Inhibition of Cell Protein Synthesis

Figure 29:
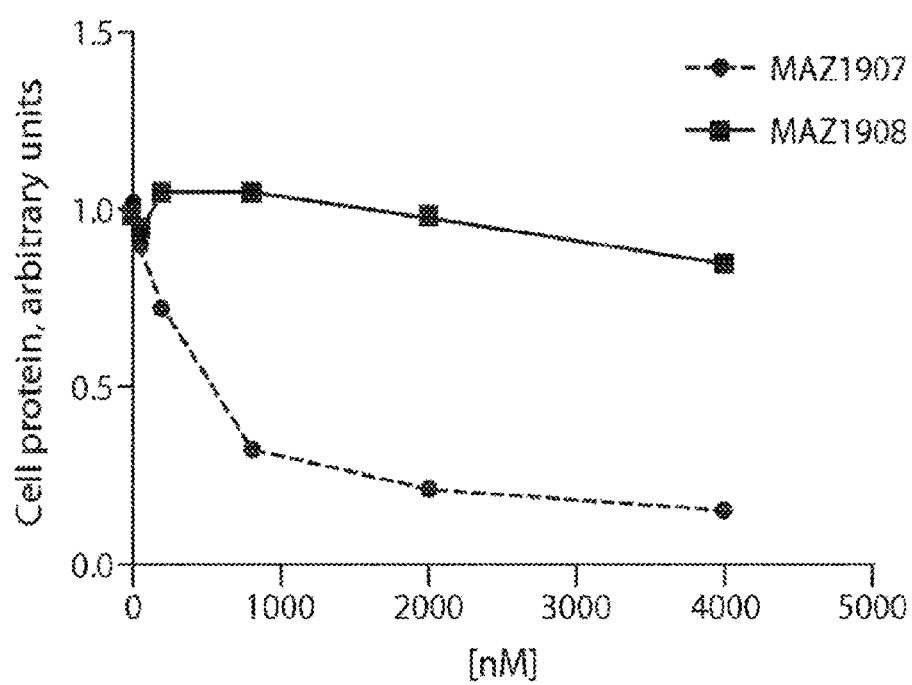
FIG. 29 shows enantiospecific activity of halofuginol in cells. Mouse embryo fibroblasts were treated with indicated concentrations of halofuginol enantiomers. Inhibition of EPRS activity was measured as a reduction in total cell protein content after 48 hour treatment. Results are shown as mean of two experiments.
Figure 29:
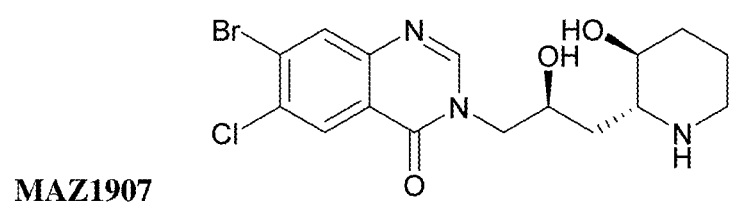
Figure 29:
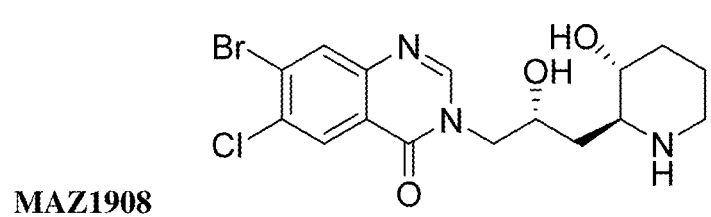

The ability of HF and related compounds to inhibit EPRS in intact cells is, at doses approximately 10 times higher than the dose required for activation of the amino acid response, reflected in their ability to limit cell protein synthesis. To test the relative activity of enantiomers MAZ1907 and MAZ1908 in cells, their ability to limit protein synthesis in growing populations of primary mouse embryo fibroblasts (MEFs) was measured. Enantiomers MAZ1907 and MAZ1908 were added at concentrations indicated to exponentially growing cultures of MEFs in DMEM/10% fetal bovine serum. Cells were washed 48 hours later, lysed in 1% NP40, and the lysates assayed for protein content. Reduction in protein content as a function of compound dose is shown in FIG. 29.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A compound of one of the following formulae:

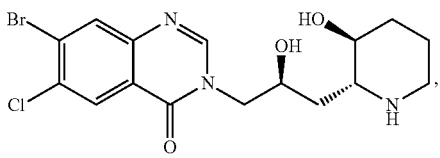

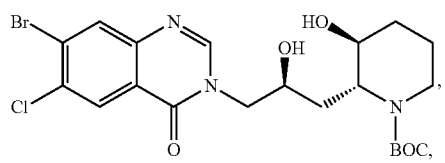

or a pharmaceutically acceptable salt thereof.

2. The compound of claim 1, wherein the compound is of the formula:

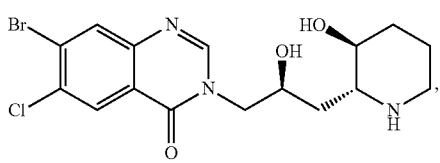 [SMILES: O=c1c2cc(Cl)c(Br)cc2ncn1C[C@@H](O)C[C@H]1NCCC[C@@H]1O]

or a pharmaceutically acceptable salt thereof.

3. The compound of claim 1, wherein the compound is of the formula:

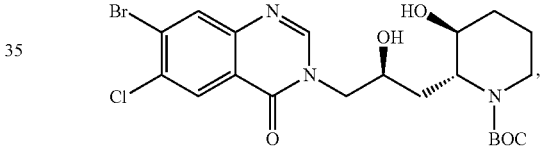

or a pharmaceutically acceptable salt thereof.

4. The compound of claim 2, wherein the compound is substantially free of other diastereomers.

5. A pharmaceutical composition comprising a compound of claim 2, or a pharmaceutically acceptable salt thereof, and optionally a pharmaceutically acceptable excipient.

6. The pharmaceutical composition of claim 5, further comprising a second anti-inflammatory agent.

7. The pharmaceutical composition of claim 6, wherein the second anti-inflammatory agent is a steroidal anti-inflammatory agent, a non-steroidal anti-inflammatory agent, or an HDAC inhibitor.

8. The pharmaceutical composition of claim 7, wherein the second anti-inflammatory agent is rapamycin, thalidomide, lenalidomide, metformin, or a derivative thereof.

9. A cosmetic composition comprising a compound of claim 2, or a pharmaceutically acceptable salt thereof, and optionally a cosmetically acceptable excipient.

10. The compound of claim 3, wherein the compound is substantially free of other diastereomers.

11. A pharmaceutical composition comprising a compound of claim 3, or a pharmaceutically acceptable salt thereof, and optionally a pharmaceutically acceptable excipient.

12. The pharmaceutical composition of claim 11, further comprising a second anti-inflammatory agent.

13. The pharmaceutical composition of claim 12, wherein the second anti-inflammatory agent is a steroidal anti-inflammatory agent, a non-steroidal anti-inflammatory agent, or an HDAC inhibitor.

14. The pharmaceutical composition of claim 13, wherein the second anti-inflammatory agent is rapamycin, thalidomide, lenalidomide, metformin, or a derivative thereof.

15. A cosmetic composition comprising a compound of claim 3, or a pharmaceutically acceptable salt thereof, and optionally a cosmetically acceptable excipient.

* * * * *

```
                         SEQUENCE LISTING

<160> NUMBER OF SEQ ID NOS: 18

<210> SEQ ID NO 1
<211> LENGTH: 119
<212> TYPE: PRT
<213> ORGANISM: Artificial Sequence
<220> FEATURE:
<223> OTHER INFORMATION: Myc-Propep

<400> SEQUENCE: 1

Met Glu Gln Lys Leu Ile Ser Glu Glu Asp Leu Asn Glu Met Glu Gln
1               5                   10                  15

Lys Leu Ile Ser Glu Glu Asp Leu Asn Glu Met Glu Gln Lys Leu Ile
            20                  25                  30

Ser Glu Glu Asp Leu Asn Glu Met Glu Gln Lys Leu Ile Ser Glu Glu
        35                  40                  45

Asp Leu Asn Glu Met Glu Gln Lys Leu Ile Ser Glu Glu Asp Leu Asn
    50                  55                  60

Glu Met Glu Ser Leu Gly Asp Leu Thr Met Glu Gln Lys Leu Ile Ser
65                  70                  75                  80

Glu Glu Asp Leu Asn Ser Ser Ser Gln Ser Leu Tyr Arg Gly Ala Phe
                85                  90                  95

Val Tyr Asp Cys Ser Pro Pro Lys Phe Lys Ala Ser Arg Ala Ser Arg
                100                 105                 110

Thr Ile Val Ser Arg Ile Thr
        115

<210> SEQ ID NO 2
<211> LENGTH: 117
<212> TYPE: PRT
<213> ORGANISM: Artificial Sequence
<220> FEATURE:
<223> OTHER INFORMATION: Myc-Nopropep

<400> SEQUENCE: 2

Met Glu Gln Lys Leu Ile Ser Glu Glu Asp Leu Asn Glu Met Glu Gln
1               5                   10                  15

Lys Leu Ile Ser Glu Glu Asp Leu Asn Glu Met Glu Gln Lys Leu Ile
            20                  25                  30

Ser Glu Glu Asp Leu Asn Glu Met Glu Gln Lys Leu Ile Ser Glu Glu
        35                  40                  45

Asp Leu Asn Glu Met Glu Gln Lys Leu Ile Ser Glu Glu Asp Leu Asn
    50                  55                  60

Glu Met Glu Ser Leu Gly Asp Leu Thr Met Glu Gln Lys Leu Ile Ser
65                  70                  75                  80

Glu Glu Asp Leu Asn Ser Ser Ser Gln Ser Leu Tyr Arg Gly Ala Phe
                85                  90                  95

Val Tyr Asp Cys Ser Lys Phe Lys Ala Ser Arg Ala Ser Arg Thr Ile
                100                 105                 110

Val Ser Arg Ile Thr
        115

<210> SEQ ID NO 3
<211> LENGTH: 19
```

```
<212> TYPE: RNA
<213> ORGANISM: Artificial Sequence
<220> FEATURE:
<223> OTHER INFORMATION: ON-TARGETplus SMARTpool siRNA J-008245-05,
      EPRS, target sequence

<400> SEQUENCE: 3
gaaguugggc cacgugaua                                                     19

<210> SEQ ID NO 4
<211> LENGTH: 19
<212> TYPE: RNA
<213> ORGANISM: Artificial Sequence
<220> FEATURE:
<223> OTHER INFORMATION: ON-TARGETplus SMARTpool siRNA J-008245-06,
      EPRS, target sequence

<400> SEQUENCE: 4
gaauauaguc ggcuaaauc                                                     19

<210> SEQ ID NO 5
<211> LENGTH: 19
<212> TYPE: RNA
<213> ORGANISM: Artificial Sequence
<220> FEATURE:
<223> OTHER INFORMATION: ON-TARGETplus SMARTpool siRNA J-008245-07,
      EPRS, target sequence

<400> SEQUENCE: 5
ggugagaugg uuacauuua                                                     19

<210> SEQ ID NO 6
<211> LENGTH: 19
<212> TYPE: RNA
<213> ORGANISM: Artificial Sequence
<220> FEATURE:
<223> OTHER INFORMATION: ON-TARGETplus SMARTpool siRNA J-008245-08,
      EPRS, target sequence

<400> SEQUENCE: 6
ucaaguagau auagcuguu                                                     19

<210> SEQ ID NO 7
<211> LENGTH: 21
<212> TYPE: DNA
<213> ORGANISM: Artificial Sequence
<220> FEATURE:
<223> OTHER INFORMATION: Col1A1, probe 15, primer 1

<400> SEQUENCE: 7
catgttcagc tttgtggacc t                                                  21

<210> SEQ ID NO 8
<211> LENGTH: 20
<212> TYPE: DNA
<213> ORGANISM: Artificial Sequence
<220> FEATURE:
<223> OTHER INFORMATION: Col1A1, probe 15, primer 2

<400> SEQUENCE: 8
gcagctgact tcagggatgt                                                    20

<210> SEQ ID NO 9
<211> LENGTH: 22
<212> TYPE: DNA
<213> ORGANISM: Artificial Sequence
<220> FEATURE:
```

```
<223> OTHER INFORMATION: Col1A2, probe 46, primer 1

<400> SEQUENCE: 9
gcaggttcac ctactctgtc ct                                          22

<210> SEQ ID NO 10
<211> LENGTH: 20
<212> TYPE: DNA
<213> ORGANISM: Artificial Sequence
<220> FEATURE:
<223> OTHER INFORMATION: Col1A2, probe 46, primer 2

<400> SEQUENCE: 10
cttgccccat tcatttgtct                                             20

<210> SEQ ID NO 11
<211> LENGTH: 19
<212> TYPE: DNA
<213> ORGANISM: Artificial Sequence
<220> FEATURE:
<223> OTHER INFORMATION: S100A4, probe 56, primer 1

<400> SEQUENCE: 11
ggagctgcct agcttcctg                                              19

<210> SEQ ID NO 12
<211> LENGTH: 23
<212> TYPE: DNA
<213> ORGANISM: Artificial Sequence
<220> FEATURE:
<223> OTHER INFORMATION: S100A4, probe 56, primer 2

<400> SEQUENCE: 12
tcctggaagt caacttcatt gtc                                         23

<210> SEQ ID NO 13
<211> LENGTH: 20
<212> TYPE: DNA
<213> ORGANISM: Artificial Sequence
<220> FEATURE:
<223> OTHER INFORMATION: CHOP, probe 21, primer 1

<400> SEQUENCE: 13
gcgacagagc cagaataaca                                             20

<210> SEQ ID NO 14
<211> LENGTH: 21
<212> TYPE: DNA
<213> ORGANISM: Artificial Sequence
<220> FEATURE:
<223> OTHER INFORMATION: CHOP, probe 21, primer 2

<400> SEQUENCE: 14
gatgcacttc cttctggaac a                                           21

<210> SEQ ID NO 15
<211> LENGTH: 18
<212> TYPE: DNA
<213> ORGANISM: Artificial Sequence
<220> FEATURE:
<223> OTHER INFORMATION: TBP, probe 107, primer 1

<400> SEQUENCE: 15
ggcggtttgg ctaggttt                                               18
```

```
<210> SEQ ID NO 16
<211> LENGTH: 22
<212> TYPE: DNA
<213> ORGANISM: Artificial Sequence
<220> FEATURE:
<223> OTHER INFORMATION: TBP, probe 107, primer 2

<400> SEQUENCE: 16
gggttatctt cacacaccat ga                                             22

<210> SEQ ID NO 17
<211> LENGTH: 23
<212> TYPE: DNA
<213> ORGANISM: Artificial Sequence
<220> FEATURE:
<223> OTHER INFORMATION: Tubb5, probe 16, primer 1

<400> SEQUENCE: 17
ctgagtacca gcagtaccag gat                                            23

<210> SEQ ID NO 18
<211> LENGTH: 20
<212> TYPE: DNA
<213> ORGANISM: Artificial Sequence
<220> FEATURE:
<223> OTHER INFORMATION: Tubb5, probe 16, primer 2

<400> SEQUENCE: 18
ctctctgcct taggcctcct                                                20
```